(12) United States Patent
Kim et al.

(10) Patent No.: US 10,818,846 B2
(45) Date of Patent: Oct. 27, 2020

(54) ELECTRON TRANSPORT MATERIAL AND ORGANIC ELECTROLUMINESCENT DEVICE COMPRISING THE SAME

(71) Applicant: Rohm and Haas Electronic Materials Korea Ltd., Cheonan (KR)

(72) Inventors: Chi-Sik Kim, Hwaseong (KR); Jeong-Eun Yang, Suwon (KR); Young-Jun Cho, Seongnam (KR); Kyung-Hoon Choi, Hwaseong (KR); Sang-Hee Cho, Suwon (KR); Jae-Hoon Shim, Seoul (KR); Hong-Yeop Na, Seoul (KR)

(73) Assignee: Rohm and Haas Electronic Materials Korea Ltd., Seoul (KR)

( * ) Notice: Subject to any disclaimer, the term of this patent is extended or adjusted under 35 U.S.C. 154(b) by 215 days.

(21) Appl. No.: 15/306,497

(22) PCT Filed: Apr. 28, 2015

(86) PCT No.: PCT/KR2015/004214
§ 371 (c)(1),
(2) Date: Oct. 25, 2016

(87) PCT Pub. No.: WO2015/167199
PCT Pub. Date: Nov. 5, 2015

(65) Prior Publication Data
US 2017/0047524 A1   Feb. 16, 2017

(30) Foreign Application Priority Data

Apr. 29, 2014 (KR) .......... 10-2014-0051726
Apr. 3, 2015 (KR) .......... 10-2015-0047543

(51) Int. Cl.
*H01L 51/00* (2006.01)
*C07D 403/10* (2006.01)
(Continued)

(52) U.S. Cl.
CPC ........ *H01L 51/0067* (2013.01); *C07B 59/002* (2013.01); *C07D 401/04* (2013.01);
(Continued)

(58) Field of Classification Search
CPC .. C07B 59/002; C07D 401/04; C07D 401/14; C07D 403/04; C07D 403/10;
(Continued)

(56) References Cited

U.S. PATENT DOCUMENTS 8,586,200 B2   11/2013   Jung et al.
8,815,418 B2   8/2014    Kim et al.
(Continued)

FOREIGN PATENT DOCUMENTS

CN    102977006 A    3/2013
KR    10-0948700 B1   3/2010
(Continued)

OTHER PUBLICATIONS

Machine translation for WO 2013/183851 A1 (publication date Dec. 2013) (Year: 2013).*

(Continued)

*Primary Examiner* — Dawn L Garrett
(74) *Attorney, Agent, or Firm* — S. Matthew Cairns

(57) ABSTRACT

The present invention relates to an electron transport material and an organic electroluminescent device comprising the material in an electron transport layer. The compounds according to the present invention as an organic electron transport material have faster electron transport property compared to a conventional electron transport material. Thus, a device comprising the compounds according to the present invention shows low driving voltage, high efficiency, and excellent lifespan property. Furthermore, the electron transport compounds have excellent color coordinate, and thus are effective in blue light-emitting.

5 Claims, 2 Drawing Sheets

(51) Int. Cl.
| | |
|---|---|
| *C09K 11/06* | (2006.01) |
| *C07D 403/04* | (2006.01) |
| *C07D 495/04* | (2006.01) |
| *C07D 403/14* | (2006.01) |
| *C07D 417/14* | (2006.01) |
| *C07B 59/00* | (2006.01) |
| *C07D 401/14* | (2006.01) |
| *C07D 487/04* | (2006.01) |
| *C07D 405/14* | (2006.01) |
| *C07D 409/14* | (2006.01) |
| *C07D 491/048* | (2006.01) |
| *C07D 401/04* | (2006.01) |
| *C09K 11/02* | (2006.01) |
| *H01L 51/50* | (2006.01) |

(52) U.S. Cl.
CPC ......... *C07D 401/14* (2013.01); *C07D 403/04* (2013.01); *C07D 403/10* (2013.01); *C07D 403/14* (2013.01); *C07D 405/14* (2013.01); *C07D 409/14* (2013.01); *C07D 417/14* (2013.01); *C07D 487/04* (2013.01); *C07D 491/048* (2013.01); *C07D 495/04* (2013.01); *C09K 11/025* (2013.01); *C09K 11/06* (2013.01); *H01L 51/0072* (2013.01); *C09K 2211/1011* (2013.01); *C09K 2211/1014* (2013.01); *H01L 51/006* (2013.01); *H01L 51/0054* (2013.01); *H01L 51/0077* (2013.01); *H01L 51/5072* (2013.01); *H01L 51/5076* (2013.01)

(58) Field of Classification Search
CPC .. C07D 403/14; C07D 405/14; C07D 409/14; C07D 417/14; C07D 487/04; C07D 491/048; C07D 495/04; C09K 11/025; C09K 11/06; C09K 2211/1011; C09K 2211/1014; H01L 51/0054; H01L 51/006; H01L 51/0067; H01L 51/0072; H01L 51/0077; H01L 51/5072; H01L 51/5076
See application file for complete search history.

(56) References Cited

U.S. PATENT DOCUMENTS

| | | | |
|---|---|---|---|
| 2011/0042654 A1* | 2/2011 | Jung | C07D 209/86 257/40 |
| 2017/0005276 A1* | 1/2017 | Kim | C07D 491/048 |
| 2017/0062730 A1* | 3/2017 | Ahn | H01L 51/0071 |

FOREIGN PATENT DOCUMENTS

| | | |
|---|---|---|
| KR | 10-0957288 B1 | 5/2010 |
| KR | 20140130297 A | 11/2014 |
| KR | 20140130397 A1 | 11/2014 |
| WO | 2013183851 A1 | 12/2013 |
| WO | 2015084021 A1 | 6/2015 |

OTHER PUBLICATIONS

Zhao, et al., "One-pot synthesis of 2-bromo-4,5-diazafluoren-9-one via a tandem oxidation-bromination-rearrangement of phenanthroline and its hammer-shaped donor-accept ororganic semiconductors", Tetrahedron, vol. 67, pp. 1977-1982 (2011).

Zhao, et al., "A bulky pyridinylfluorene-fuctionalizing approach to synthesize diarylfluorene-based bipolar host materials for efficient red, green, blue and white electrophosphorescent devices", J. Materials Chemistry, vol. 1, pp. 3482-3490 (2013).

Notification of Reason for Refusal for Japanese application No. 2016-563093; dated Apr. 28, 2015.

* cited by examiner

ELECTRON TRANSPORT MATERIAL AND ORGANIC ELECTROLUMINESCENT DEVICE COMPRISING THE SAME

TECHNICAL FIELD

The present invention relates to an electron transport material and an organic electroluminescent device comprising the same.

BACKGROUND ART

An electroluminescent (EL) device is a self-light-emitting device with the advantages of providing a wider viewing angle, a greater contrast ratio, and a faster response time. The first organic EL device was developed by Eastman Kodak, by using small aromatic diamine molecules and aluminum complexes as materials for forming a light-emitting layer (see Appl. Phys. Lett. 51, 913, 1987).

An organic EL device changes electric energy into light by the injection of a charge into an organic light-emitting material, and commonly comprises an anode, a cathode, and an organic layer formed between the two electrodes. The organic layer of the organic EL device may be composed of a hole injection layer (HIL), a hole transport layer (HTL), an electron blocking layer (EBL), a light-emitting layer (EML) (containing host and dopant materials), an electron buffer layer, a hole blocking layer (HBL), an electron transport layer (ETL), an electron injection layer (EIL), etc.; the materials used in the organic layer can be classified into a hole injection material, a hole transport material, an electron blocking material, a light-emitting material, an electron buffer material, a hole blocking material, an electron transport material, an electron injection material, etc., depending on functions. In the organic EL device, holes from an anode and electrons from a cathode are injected into a light-emitting layer by electric voltage, and an exciton having high energy is produced by the recombination of holes and electrons. The organic light-emitting compound moves into an excited state by the energy and emits light from energy when the organic light-emitting compound returns to the ground state from the excited state.

The most important factor determining luminous efficiency in an organic EL device is light-emitting materials. The light-emitting materials are required to have the following features: high quantum efficiency, high movement degree of an electron and a hole, and formability of a uniform and stable layer. The light-emitting material is classified into blue light-emitting materials, green light-emitting materials, and red light-emitting materials according to the light-emitting color, and further includes yellow light-emitting materials or orange light-emitting materials. Furthermore, the light-emitting material is classified into a host material and a dopant material in a functional aspect. Recently, an urgent task is the development of an organic EL device having high efficacy and long operating lifespan. In particular, the development of highly excellent light-emitting material over conventional light-emitting materials is urgently required, considering the EL properties necessary for medium- and large-sized OLED panels. For this, preferably, as a solvent in a solid state and an energy transmitter, a host material should have high purity, and a suitable molecular weight in order to be deposited under vacuum. Furthermore, a host material is required to have high glass transition temperature and pyrolysis temperature for guaranteeing thermal stability, high electrochemical stability for long lifespan, easy formability of an amorphous thin film, good adhesion with adjacent layers, and no movement between layers.

Meanwhile, in an organic EL device, an electron transport material actively transports electrons from a cathode to a light-emitting layer and inhibits transport of holes which are not recombined in the light-emitting layer to increase recombination opportunity of holes and electrons in the light-emitting layer. Thus, electron-affinitive materials are used as an electron transport material. Organic metal complexes having light-emitting function such as $Alq_3$ are excellent in transporting electrons, and thus have been conventionally used as an electron transport material. However, $Alq_3$ has problems in that it moves to other layers and shows reduction of color purity when used in blue light-emitting devices. Therefore, new electron transport materials have been required, which do not have the above problems, are highly electron-affinitive, and quickly transport electrons in organic EL devices to provide organic EL devices having high luminous efficiency.

Korean Patent Nos. 10-0957288 and 10-0948700 disclose compounds in which a nitrogen-containing heterocyclic group is bonded to a carbazolyl group, and compounds in which a nitrogen-containing heterocyclic group is bonded to an arylcarbazolyl group or a carbazolylalkylene group, respectively. However, the above patents disclose the above compounds as materials used in a light-emitting layer, and merely recite conventional metal complex compounds, and oxazole, thiazole, oxadiazole, or thiadiazole derivatives as electron transport materials.

The present inventors have found that an organic EL device comprising compounds having a carbazole-fluorene skeleton, wherein a nitrogen-containing heterocyclic group is bonded to a nitrogen atom of the carbazole, which were conventionally used in a light-emitting layer, as an electron transport material in an electron transport layer has high efficiency and improved lifespan.

DISCLOSURE OF THE INVENTION

Problems to be Solved

The object of the present invention is to provide an organic EL device having high efficiency and long lifespan.

Solution to Problems

The above objective can be achieved by an electron transport material comprising the compound represented by the following formula 1:

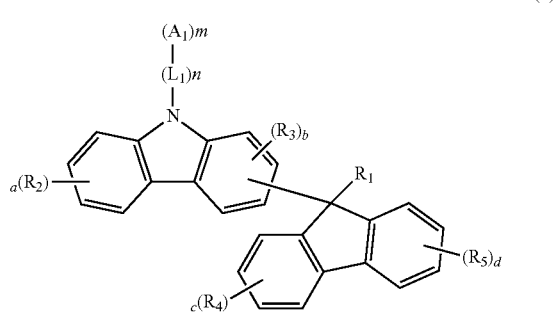

(1)

wherein $A_1$ represents a substituted or unsubstituted, nitrogen-containing 5- to 30-membered heteroaryl group;

$L_1$ represents a single bond, a substituted or unsubstituted (C6-C30)arylene group, or a substituted or unsubstituted 5- to 30-membered heteroarylene group;

$R_1$ represents a substituted or unsubstituted (C1-C30)alkyl group, a substituted or unsubstituted (C6-C30)aryl group, a substituted or unsubstituted 5- to 30-membered heteroaryl group, a substituted or unsubstituted (C3-C30)cycloalkyl group, a substituted or unsubstituted (C1-C30)alkylamino group, a substituted or unsubstituted (C6-C30)arylamino group, or a substituted or unsubstituted (C1-C30)alkyl(C6-C30)arylamino group;

$R_2$ represents hydrogen, deuterium, a halogen, a cyano group, a substituted or unsubstituted (C1-C30)alkyl group, a substituted or unsubstituted (C6-C30)aryl group, a substituted or unsubstituted 5- to 30-membered heteroaryl group, a substituted or unsubstituted (C3-C30)cycloalkyl group, a substituted or unsubstituted (C1-C30)alkoxy group, a substituted or unsubstituted (C1-C30)alkylsilyl group, a substituted or unsubstituted (C6-C30)arylsilyl group, a substituted or unsubstituted (C6-C30)aryl(C1-C30)alkylsilyl group, a substituted or unsubstituted (C1-C30)alkylamino group, a substituted or unsubstituted (C6-C30)arylamino group, a substituted or unsubstituted (C1-C30)alkyl(C6-C30)arylamino group, or a structure of formula 2:

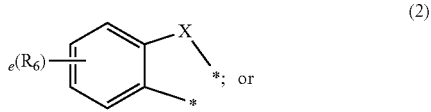

(2)

$R_2$, fused to the carbazole structure, forms a benzocarbazole ring;

$R_3$ represents hydrogen, deuterium, a halogen, a cyano group, a substituted or unsubstituted (C1-C30)alkyl group, a substituted or unsubstituted (C6-C30)aryl group, a substituted or unsubstituted 5- to 30-membered heteroaryl group, a substituted or unsubstituted (C3-C30)cycloalkyl group, a substituted or unsubstituted (C1-C30)alkoxy group, a substituted or unsubstituted (C1-C30)alkylsilyl group, a substituted or unsubstituted (C6-C30)arylsilyl group, a substituted or unsubstituted (C6-C30)aryl(C1-C30)alkylsilyl group, a substituted or unsubstituted (C1-C30)alkylamino group, a substituted or unsubstituted (C6-C30)arylamino group, or a substituted or unsubstituted (C1-C30)alkyl(C6-C30)arylamino group;

X represents O, S, $NR_{11}$, or $SiR_{12}R_{13}$;

$R_4$, $R_5$, and $R_6$ each independently represent hydrogen, deuterium, a halogen, a cyano group, a substituted or unsubstituted (C1-C30)alkyl group, a substituted or unsubstituted (C6-C30)aryl group, a substituted or unsubstituted 5- to 30-membered heteroaryl group, a substituted or unsubstituted (C3-C30)cycloalkyl group, a substituted or unsubstituted (C1-C30)alkoxy group, a substituted or unsubstituted (C1-C30)alkylsilyl group, a substituted or unsubstituted (C6-C30)arylsilyl group, a substituted or unsubstituted (C6-C30)aryl(C1-C30)alkylsilyl group, a substituted or unsubstituted (C1-C30)alkylamino group, a substituted or unsubstituted (C6-C30)arylamino group, or a substituted or unsubstituted (C1-C30)alkyl(C6-C30)arylamino group; or are linked to an adjacent substituent(s) to form a substituted or unsubstituted mono- or polycyclic, (C3-C30) alicyclic or aromatic ring whose carbon atom(s) may be replaced with at least one hetero atom selected from nitrogen, oxygen and sulfur;

$R_{11}$ to $R_{13}$ each independently represent a substituted or unsubstituted (C1-C30)alkyl group, a substituted or unsubstituted (C6-C30)aryl group, or a substituted or unsubstituted 5- to 30-membered heteroaryl group; or are linked to an adjacent substituent(s) to form a substituted or unsubstituted mono- or polycyclic, (C3-C30) alicyclic or aromatic ring whose carbon atom(s) may be replaced with at least one hetero atom selected from nitrogen, oxygen and sulfur;

a, c, d, and e each independently represent an integer of 1 to 4; where a, c, d, or e is an integer of 2 or more, each $R_2$, each $R_4$, each $R_5$, or each $R_6$ is the same or different;

b represents an integer of 1 to 3; where b is an integer of 2 or more, each $R_3$ is the same or different;

n represents an integer of 0 or 1;

m represents an integer of 1 or 2; and the heteroaryl and heteroarylene groups contain at least one hetero atom selected from B, N, O, S, P(=O), Si, and P.

Effects of the Invention

According to the present invention, an electron transport material is provided, which provides an organic EL device with high efficiency and long lifespan, and the production of a light-emitting device, a display device, or a lighting device is possible by using an organic EL device.

EMBODIMENTS OF THE INVENTION

Figure 1:
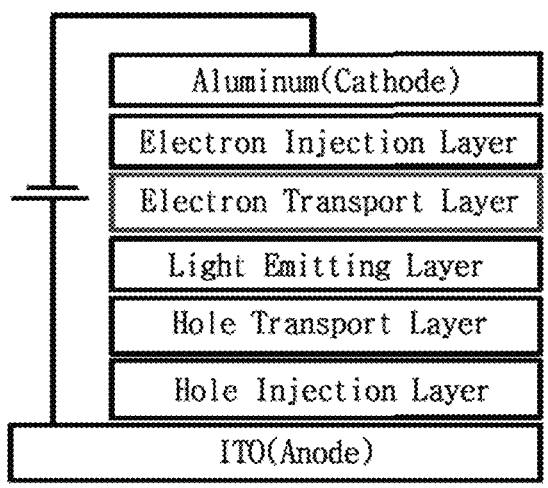
FIG. 1 shows one embodiment of the structure of the organic EL device comprising the electron transport layer according to the present invention.

Hereinafter, the present invention will be described in detail. However, the following description is intended to explain the invention, and is not meant in any way to restrict the scope of the invention.

The compound of formula 1 is represented by the following formula 3, 4, or 5:

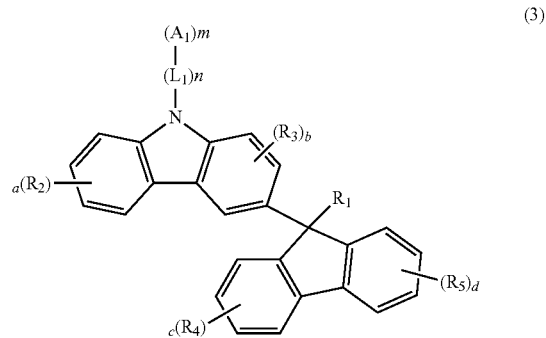

(3)

-continued

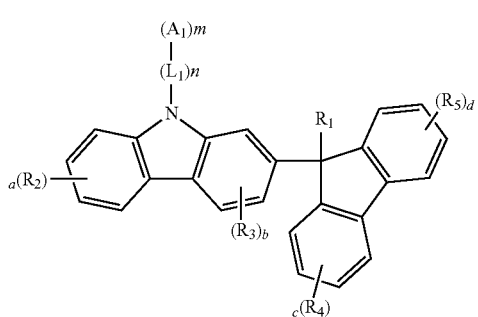

(4)

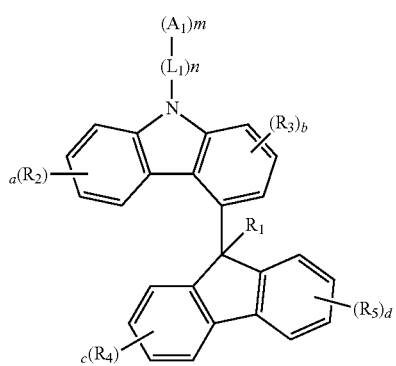

(5)

wherein

A₁, L₁, R₁, R₂, R₃, R₄, R₅, a, b, c, d, m, and n are as defined in formula 1.

In formula 1, A₁ preferably represents a substituted or unsubstituted pyridyl, a substituted or unsubstituted pyrimidyl, a substituted or unsubstituted triazinyl, a substituted or unsubstituted pyrazinyl, a substituted or unsubstituted quinolinyl, a substituted or unsubstituted quinazolinyl, a substituted or unsubstituted quinoxalinyl, a substituted or unsubstituted naphthyridinyl, or a substituted or unsubstituted phenanthrolinyl.

In formula 1, L₁ preferably represents a single bond, or a substituted or unsubstituted (C6-C12)arylene group.

In formula 1, R₁ preferably represents a substituted or unsubstituted (C6-C12)aryl group, or a substituted or unsubstituted 5- to 15-membered heteroaryl group.

In formula 1, R₂ preferably represents hydrogen, a (C6-012)aryl group which is unsubstituted or substituted with a di(C6-012)arylamine group, a substituted or unsubstituted 5- to 15-membered heteroaryl group, or a structure of formula 2, wherein X represents O, S, or NR₁₁, and R₁₁ represents a substituted or unsubstituted (C6-012)aryl group, or R₂ forms a benzocarbazole ring by fusing to the carbazole structure.

Herein, "(C1-C30)alkyl(ene)" is meant to be a linear or branched alkyl(ene) having 1 to 30 carbon atoms, in which the number of carbon atoms is preferably 1 to 20, more preferably 1 to 10, and includes methyl, ethyl, n-propyl, isopropyl, n-butyl, isobutyl, tert-butyl, etc. "(C2-C30)alkenyl" is meant to be a linear or branched alkenyl having 2 to 30 carbon atoms, in which the number of carbon atoms is preferably 2 to 20, more preferably 2 to 10, and includes vinyl, 1-propenyl, 2-propenyl, 1-butenyl, 2-butenyl, 3-butenyl, 2-methylbut-2-enyl, etc. "(C2-C30)alkynyl" is a linear or branched alkynyl having 2 to 30 carbon atoms, in which the number of carbon atoms is preferably 2 to 20, more preferably 2 to 10, and includes ethynyl, 1-propynyl, 2-propynyl, 1-butynyl, 2-butynyl, 3-butynyl, 1-methylpent-2-ynyl, etc. "(C3-C30)cycloalkyl" is a mono- or polycyclic hydrocarbon having 3 to 30 carbon atoms, in which the number of carbon atoms is preferably 3 to 20, more preferably 3 to 7, and includes cyclopropyl, cyclobutyl, cyclopentyl, cyclohexyl, etc. "3- to 7-membered heterocycloalkyl" is a cycloalkyl having at least one heteroatom selected from B, N, O, S, P(=O), Si and P, preferably O, S and N, and 3 to 7, preferably 5 to 7 ring backbone atoms, and includes tetrahydrofuran, pyrrolidine, thiolan, tetrahydropyran, etc. "(C6-C30)aryl(ene)" is a monocyclic or fused ring derived from an aromatic hydrocarbon having 6 to 30 carbon atoms, in which the number of carbon atoms is preferably 6 to 20, more preferably 6 to 15, and includes phenyl, biphenyl, terphenyl, naphthyl, fluorenyl, phenanthrenyl, anthracenyl, indenyl, triphenylenyl, pyrenyl, tetracenyl, perylenyl, chrysenyl, naphthacenyl, fluoranthenyl, etc. "3- to 30-membered heteroaryl(ene)" is an aryl group having at least one, preferably 1 to 4 heteroatom selected from the group consisting of B, N, O, S, P(=O), Si and P, and 3 to 30 ring backbone atoms; is a monocyclic ring, or a fused ring condensed with at least one benzene ring; has preferably 3 to 20, more preferably 3 to 15 ring backbone atoms; may be partially saturated; may be one formed by linking at least one heteroaryl or aryl group to a heteroaryl group via a single bond(s); and includes a monocyclic ring-type heteroaryl including furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl including benzofuranyl, benzothiophenyl, isobenzofuranyl, dibenzofuranyl, dibenzothiophenyl, benzoimidazolyl, benzothiazolyl, benzoisothiazolyl, benzoisoxazolyl, benzoxazolyl, isoindolyl, indolyl, indazolyl, benzothiadiazolyl, quinolyl, isoquinolyl, cinnolinyl, quinazolinyl, quinoxalinyl, carbazolyl, phenoxazinyl, phenanthridinyl, benzodioxolyl, etc. "Halogen" includes F, Cl, Br and I.

Herein, "substituted" in the expression "substituted or unsubstituted" means that a hydrogen atom in a certain functional group is replaced with another atom or group, i.e., a substituent. Substituents of the substituted alkyl(ene) group, the substituted alkenyl group, the substituted alkynyl group, the substituted alkoxy, the substituted cycloalkyl group, the substituted aryl(ene) group, the substituted heteroaryl(ene) group, the substituted alkylsilyl group, the substituted arylsilyl group, the substituted alkylamino group, the substituted arylamino group, or the substituted mono- or polycyclic, (C3-C30) alicyclic or aromatic ring in the above formulae are each independently at least one selected from the group consisting of deuterium; a halogen; a cyano group; a carboxyl group; a nitro group; a hydroxyl group; a (C1-C30)alkyl group; a halo(C1-C30)alkyl group; a (C2-C30)alkenyl group; a (C2-C30)alkynyl group; a (C1-C30)alkoxy group; a (C1-C30)alkylthio group; a (C3-C30) cycloalkyl group; a (C3-C30)cycloalkenyl group; a 3- to 7-membered heterocycloalkyl group; a (C6-C30)aryloxy group; a (C6-C30)arylthio group; a 3- to 30-membered heteroaryl group which is unsubstituted or substituted with a (C6-C30)aryl group; a (C6-C30)aryl group which is unsubstituted or substituted with a 3- to 30-membered heteroaryl group; a tri(C1-C30)alkylsilyl group; a tri(C6-C30)arylsilyl group; a di(C1-C30)alkyl(C6-C30)arylsilyl group; a (C1-C30)alkyldi(C6-C30)arylsilyl group; an amino group; a mono- or di(C1-C30)alkylamino group; a mono- or di(C6-C30)arylamino group; a (C1-C30)alkyl(C6-C30)arylamino group; a (C1-C30)alkylcarbonyl group; a (C1-C30) alkoxycarbonyl group; a (C6-C30)arylcarbonyl group; a di(C6-C30)arylboronyl group; a di(C1-C30)alkylboronyl group; a (C1-C30)alkyl(C6-C30)arylboronyl group; a (C6-C30)aryl(C1-C30)alkyl group; and a (C1-C30)alkyl(C6-C30)aryl group.
The compound of formula 1 may be selected from the group consisting of the following compounds, but is not limited thereto:
ETL-1
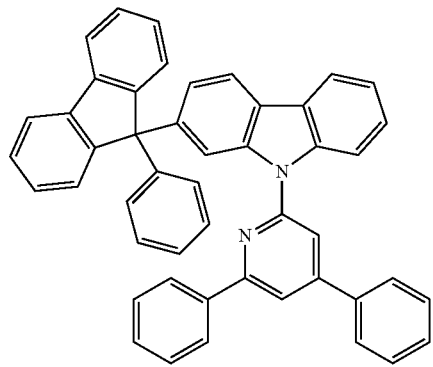
ETL-2
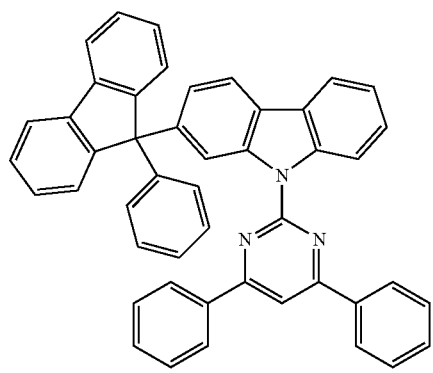
ETL-3
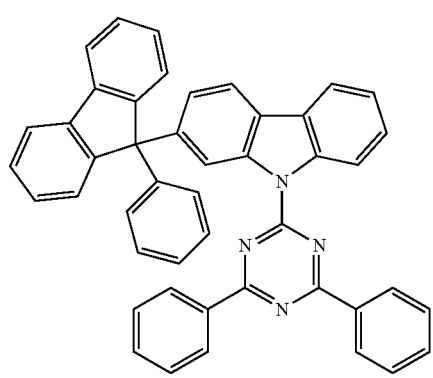
ETL-4
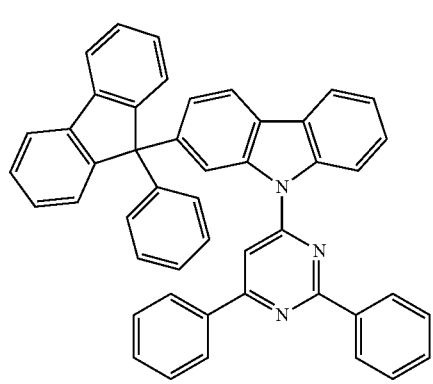
ETL-5
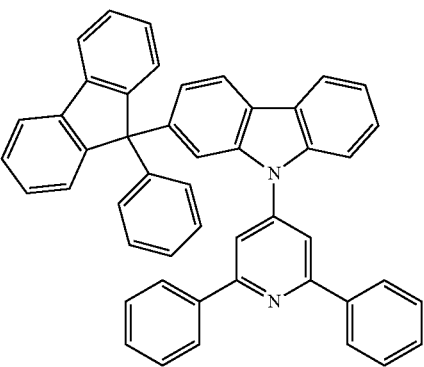
ETL-6
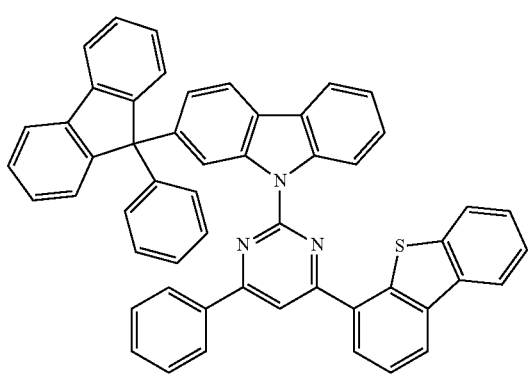
ETL-7
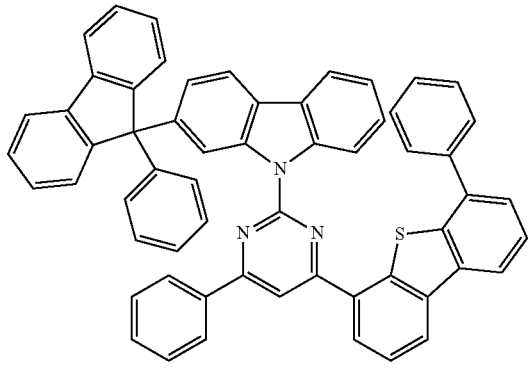
ETL-8
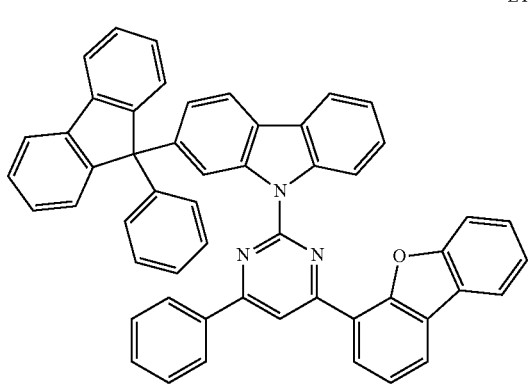

ETL-9
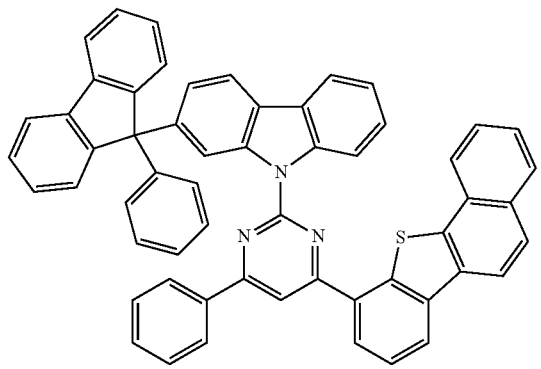
ETL-13
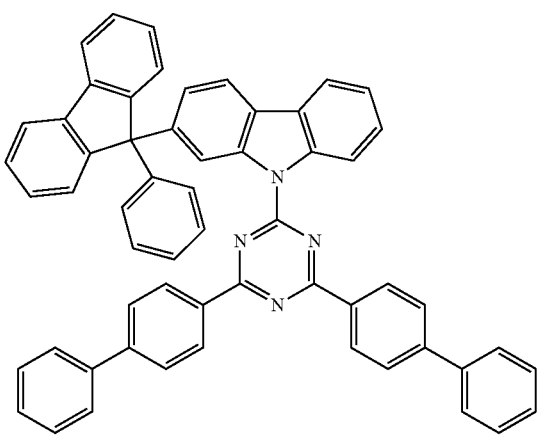
ETL-10
ETL-11
ETL-12
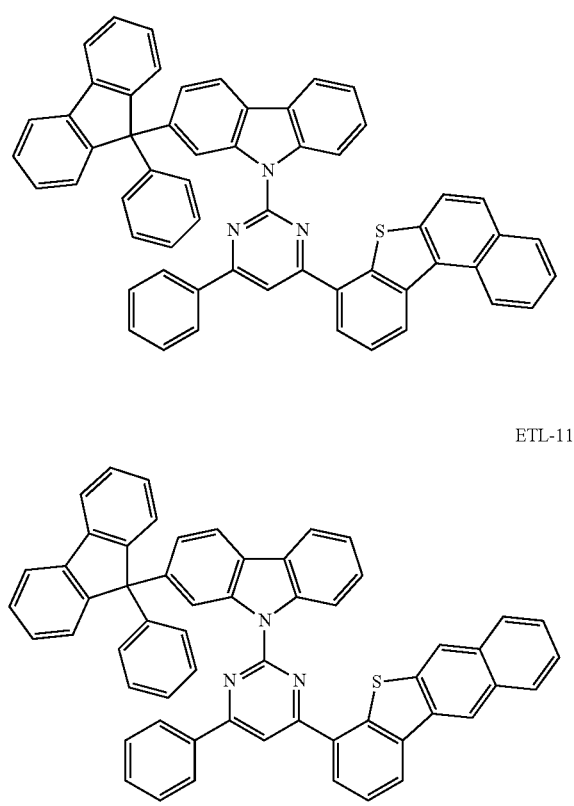
ETL-14
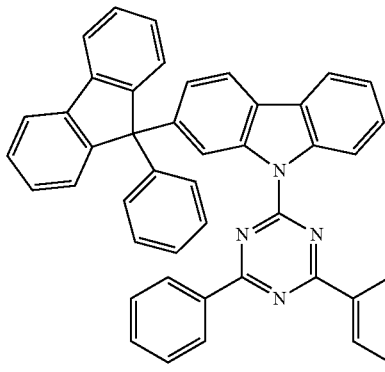
ETL-15
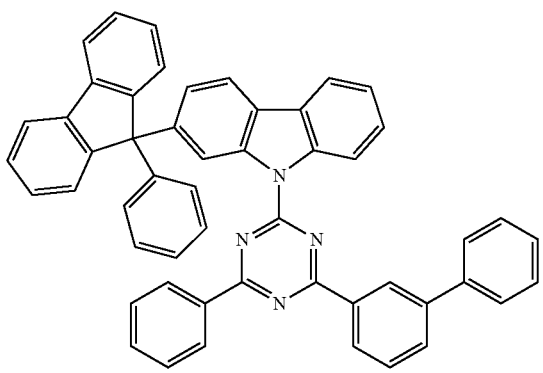

-continued
ETL-16
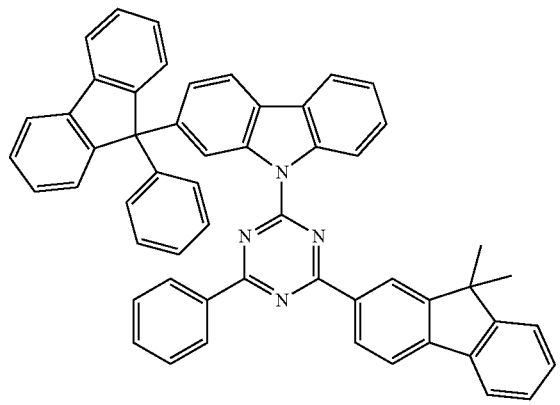
ETL-17
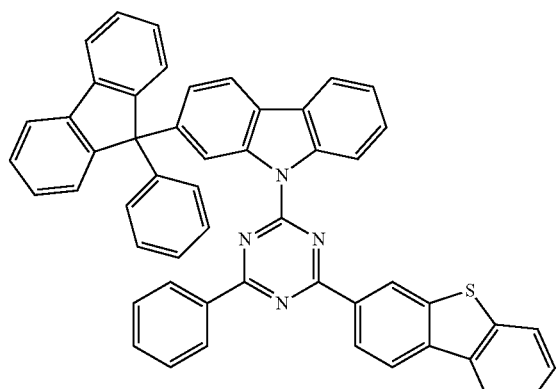
ETL-18
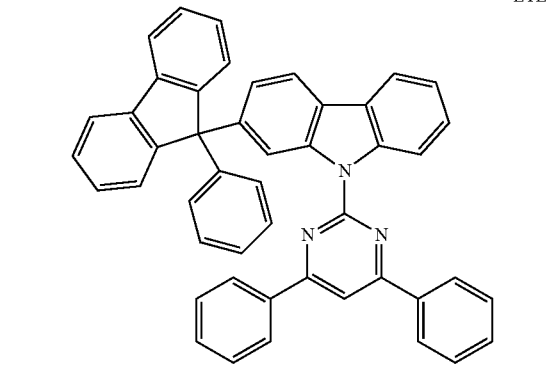
ETL-19
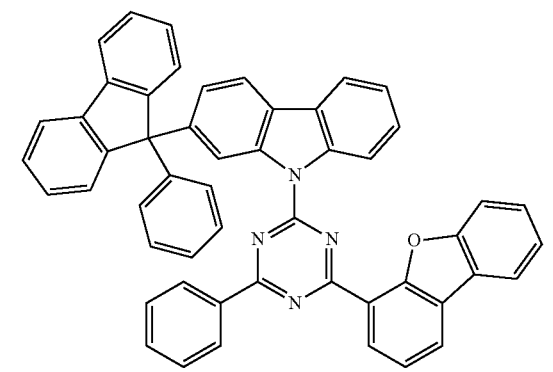
ETL-20
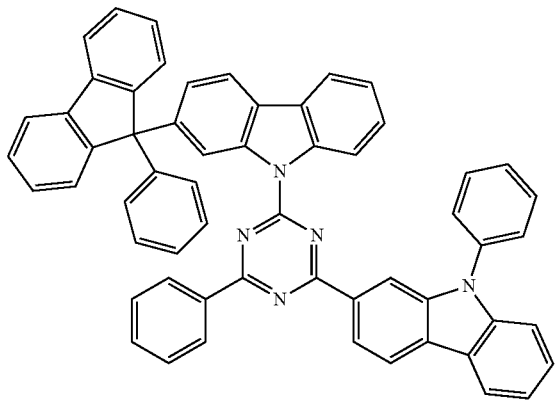
ETL-21
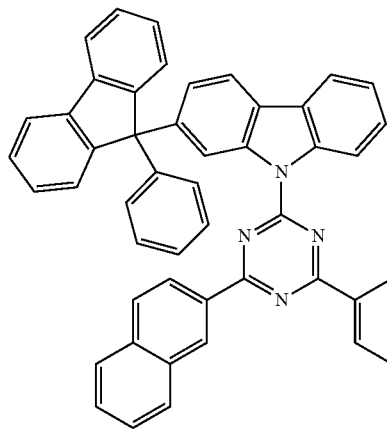
ETL-22
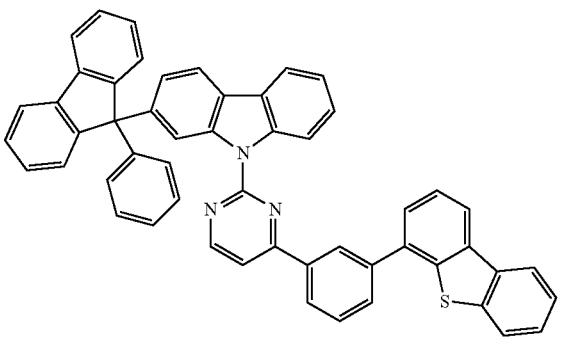
ETL-23
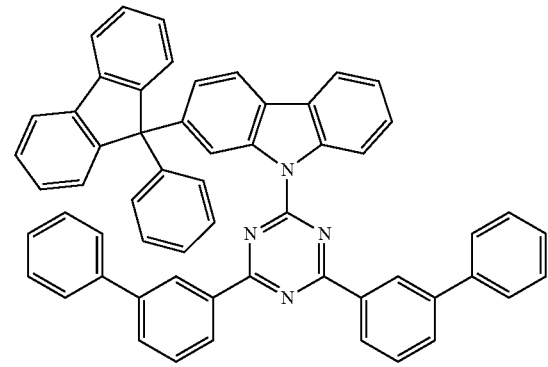

-continued
ETL-24
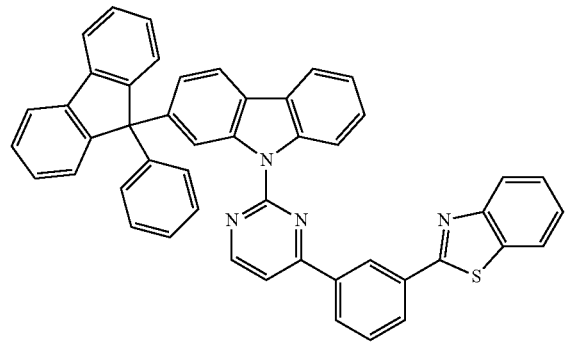
ETL-25
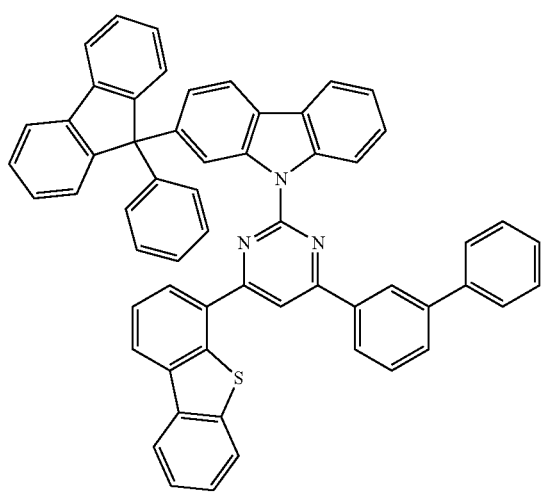
ETL-26
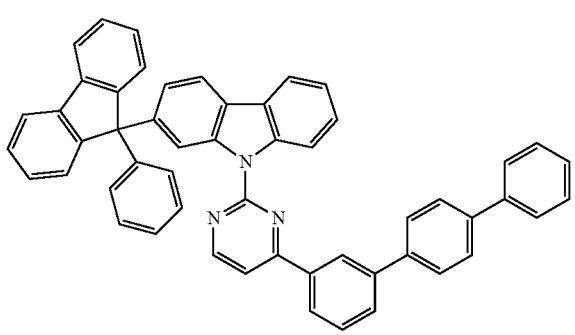
ETL-27
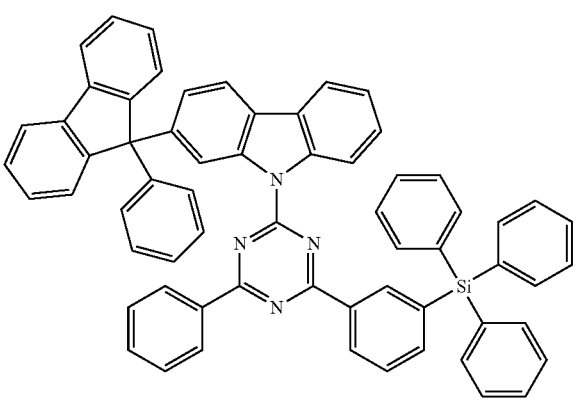
-continued
ETL-28
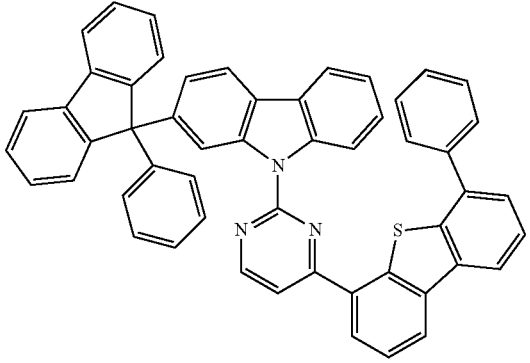
ETL-29
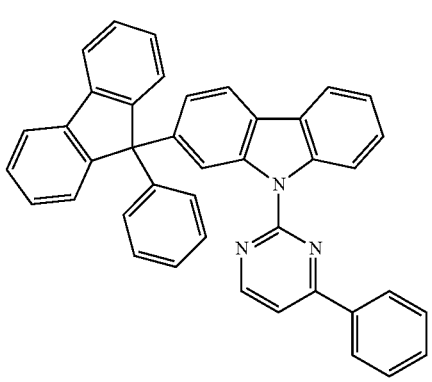
ETL-30
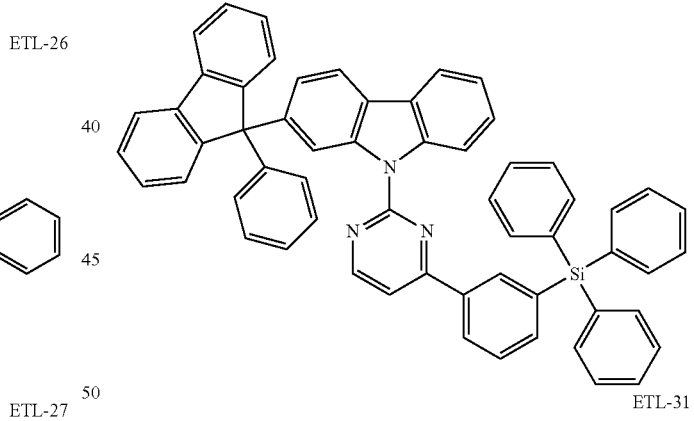
ETL-31
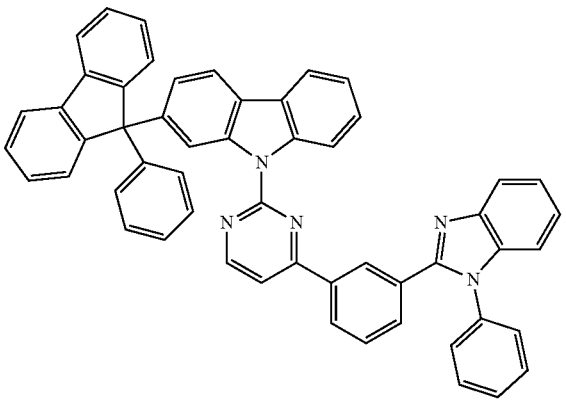

ETL-32
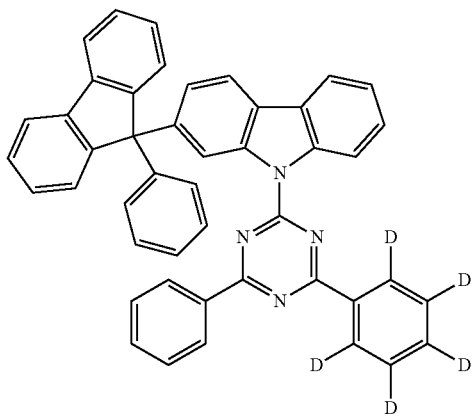
ETL-33
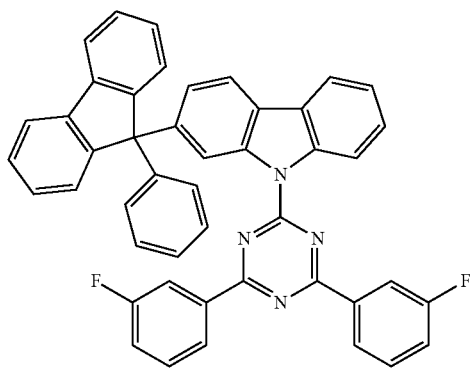
ETL-34
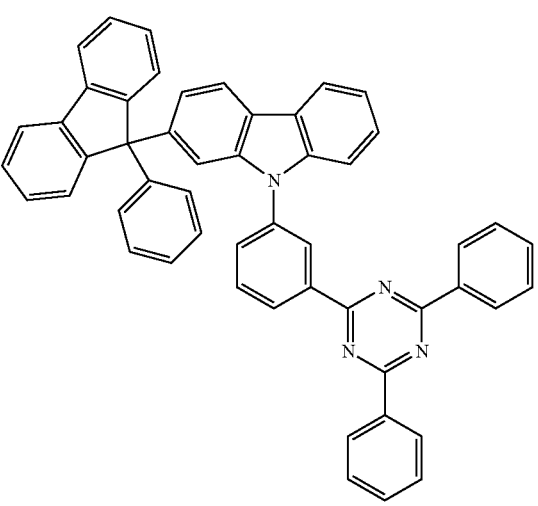
ETL-35
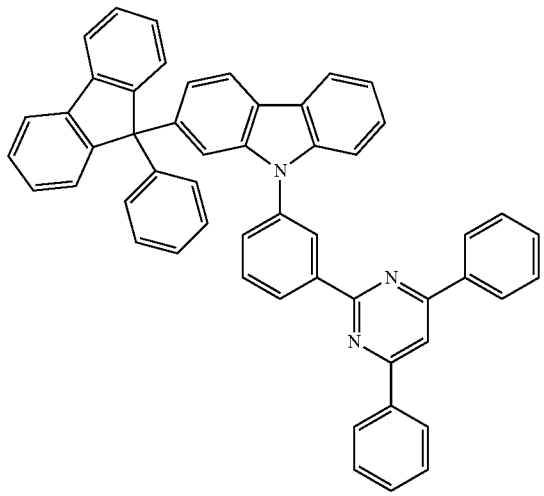
ETL-36
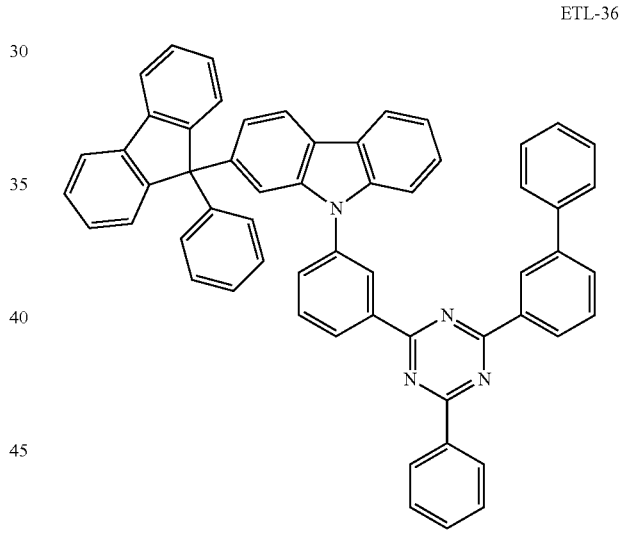
ETL-37
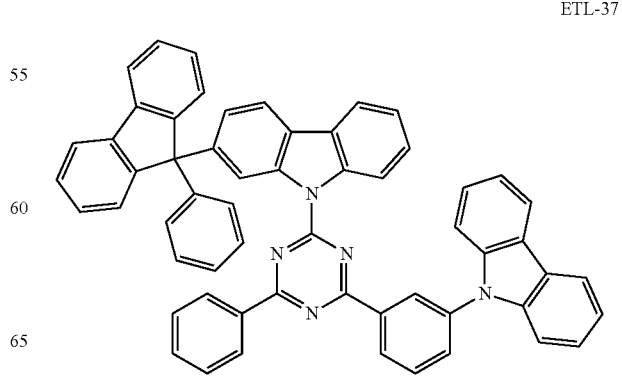

ETL-38
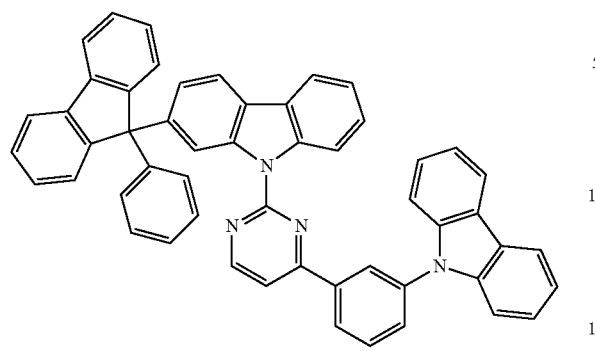
ETL-39
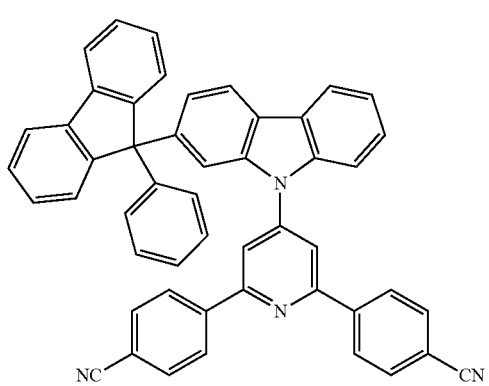
ETL-40
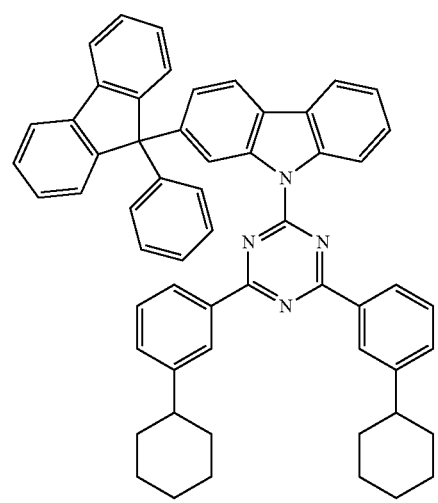
ETL-41
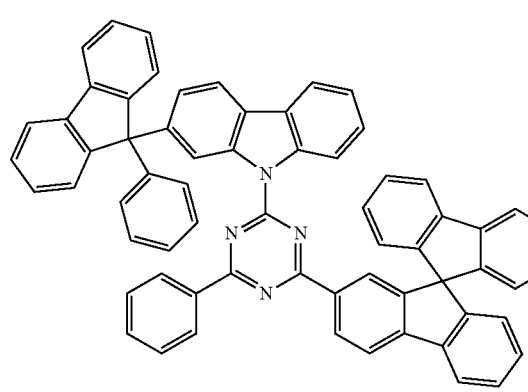
ETL-42
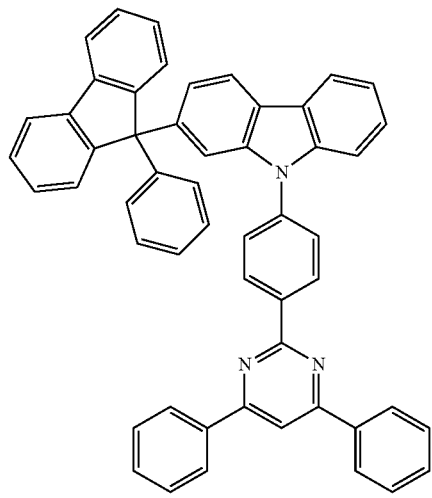
ETL-43
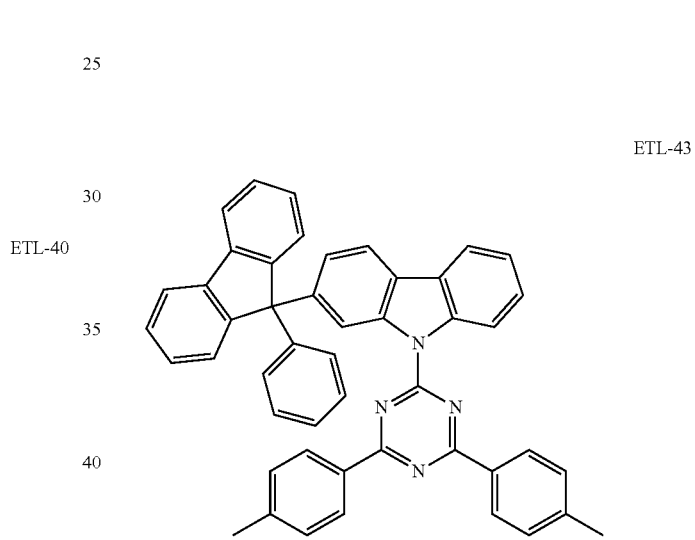
ETL-44
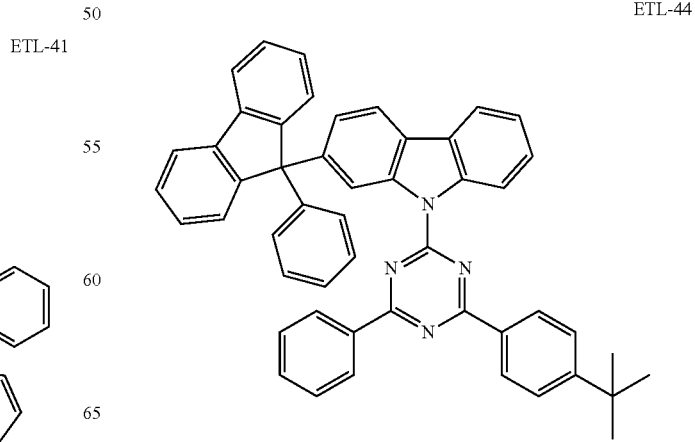

ETL-45
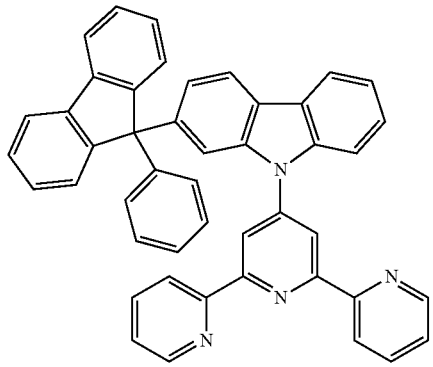
ETL-46
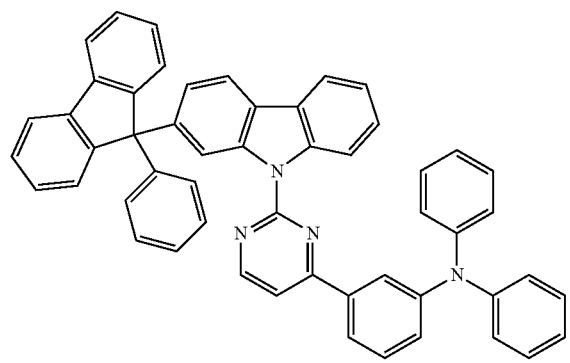
ETL-47
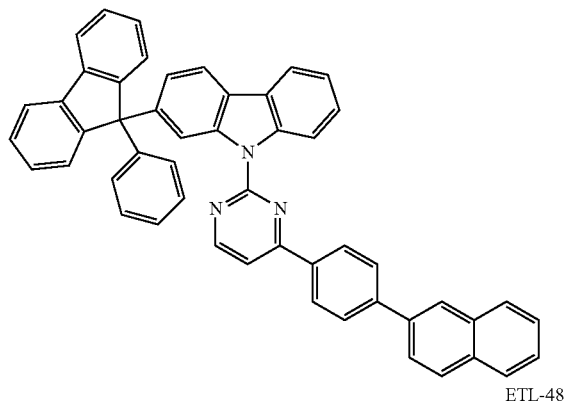
ETL-48
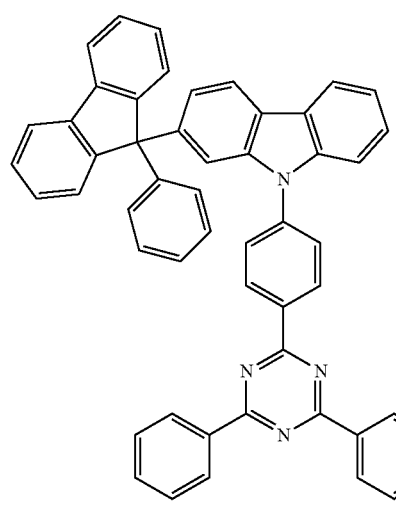
ETL-49
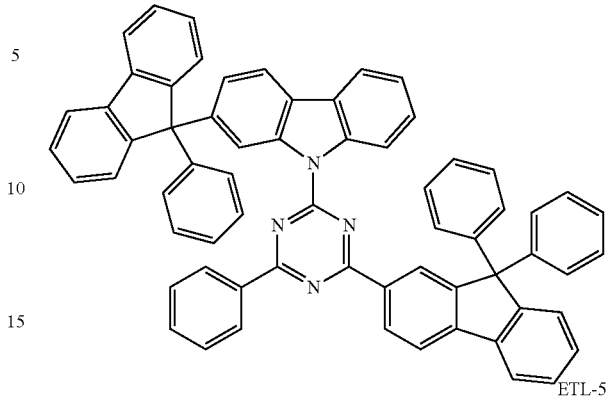
ETL-50
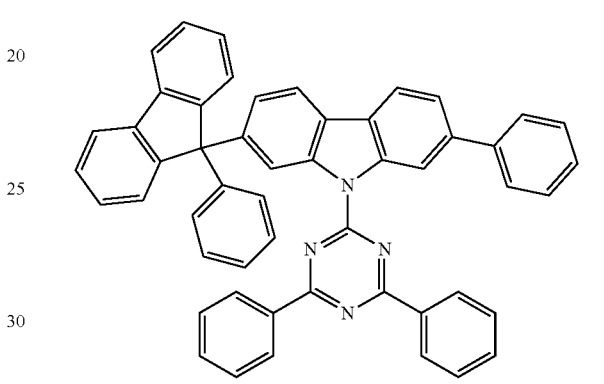
ETL-51
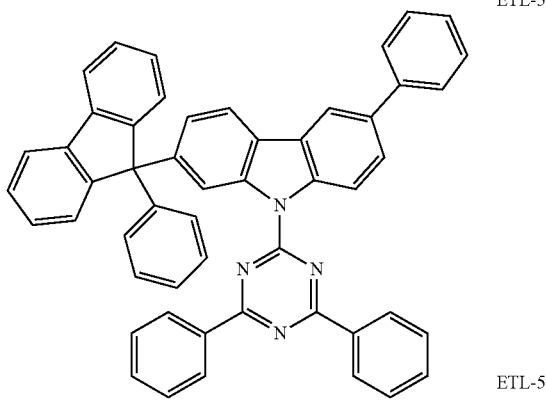
ETL-52
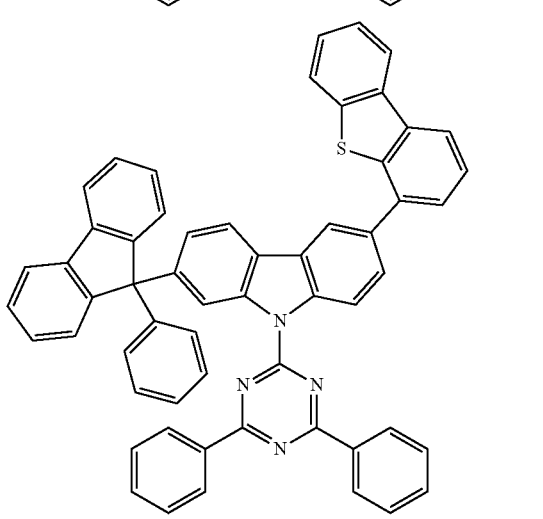

ETL-53
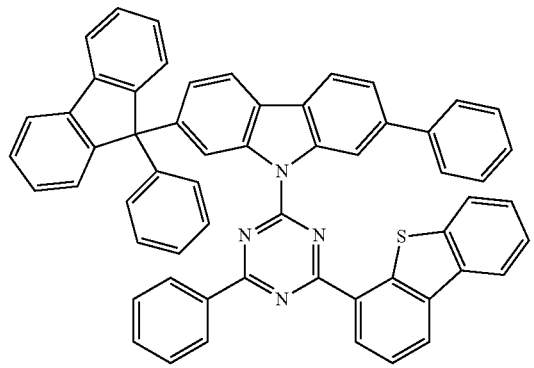
ETL-54
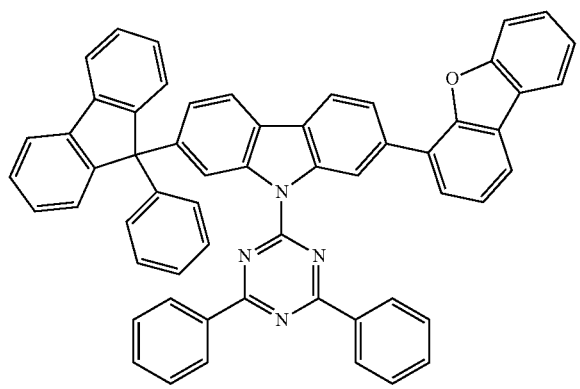
ETL-55
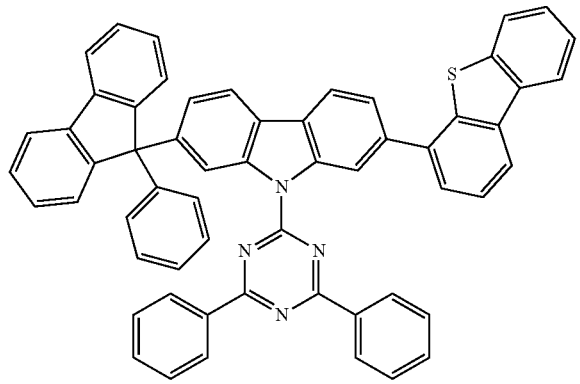
ETL-56
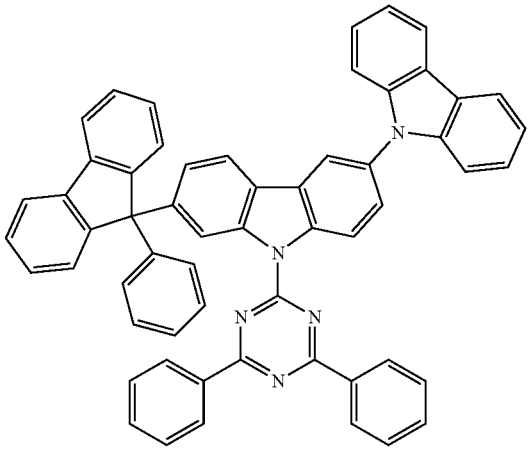
ETL-57
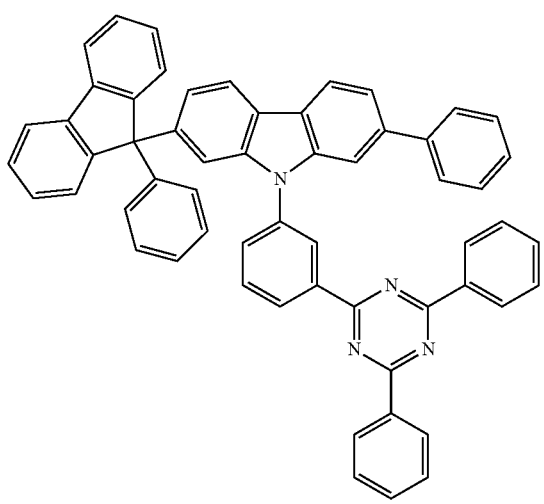
ETL-58
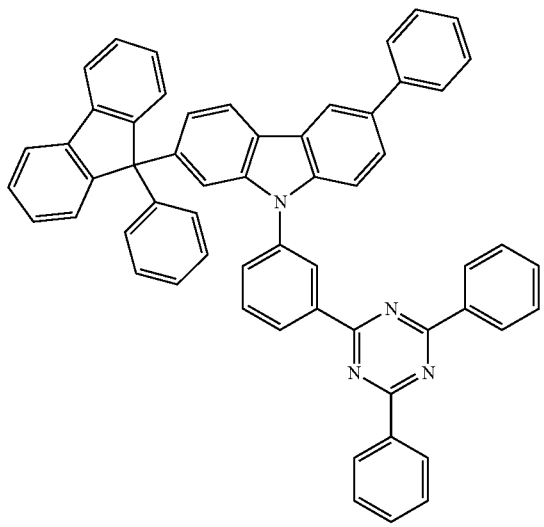

ETL-59
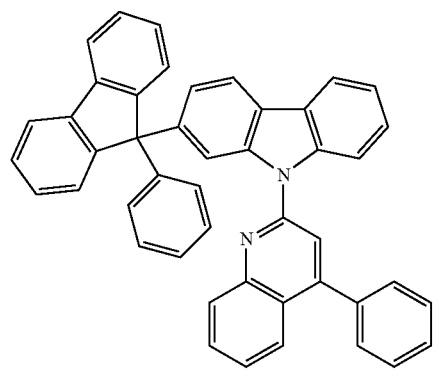
ETL-60
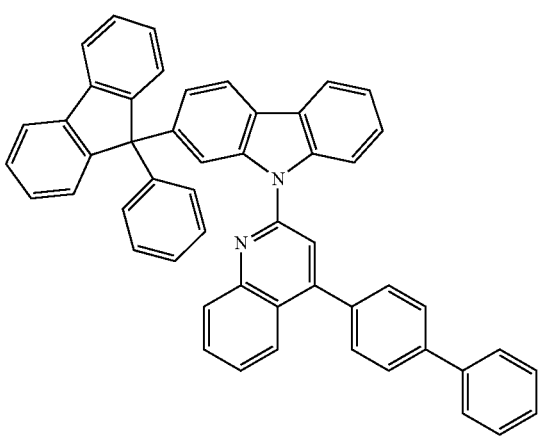
ETL-61
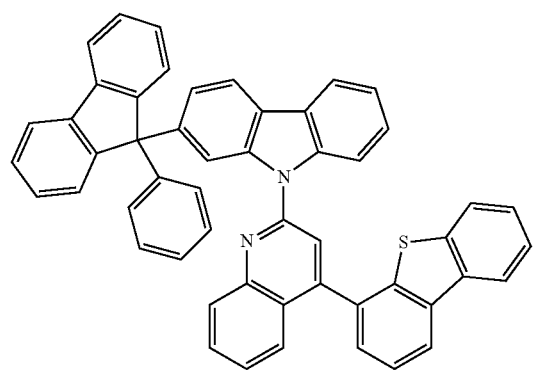
ETL-62
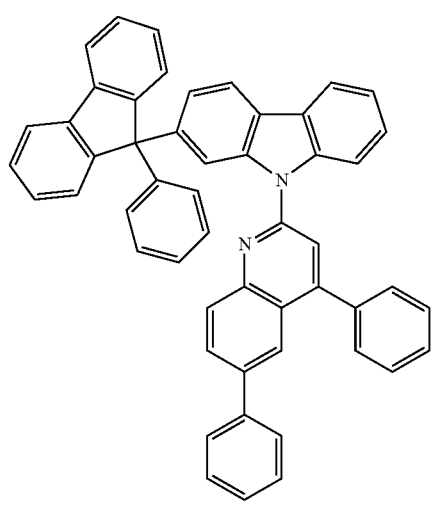
ETL-63
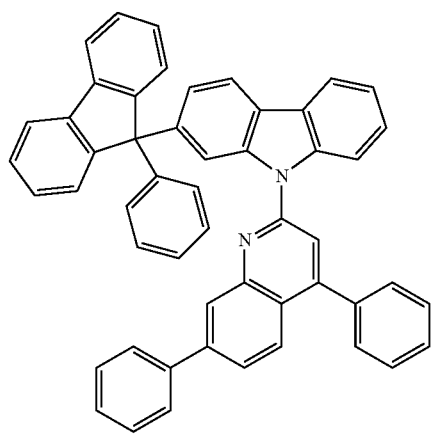
ETL-64
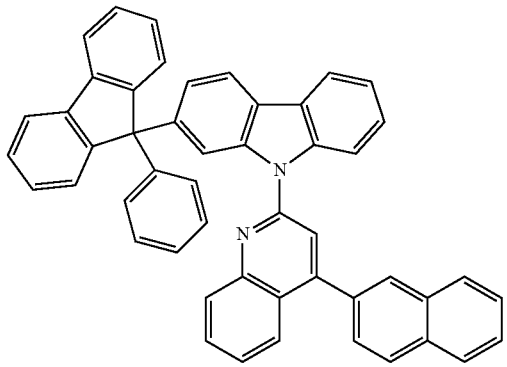

ETL-65
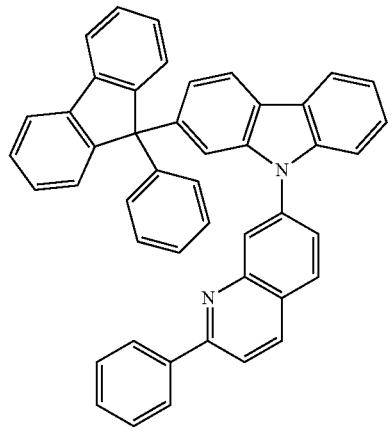
ETL-66
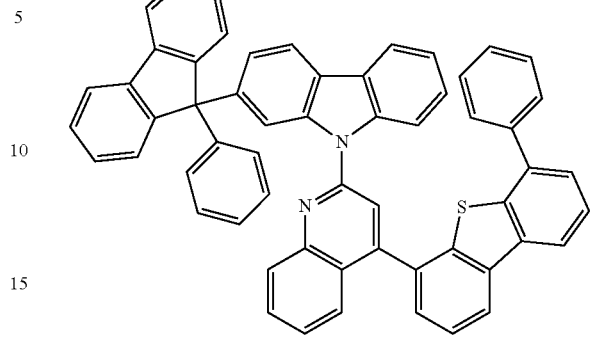
ETL-67
ETL-68
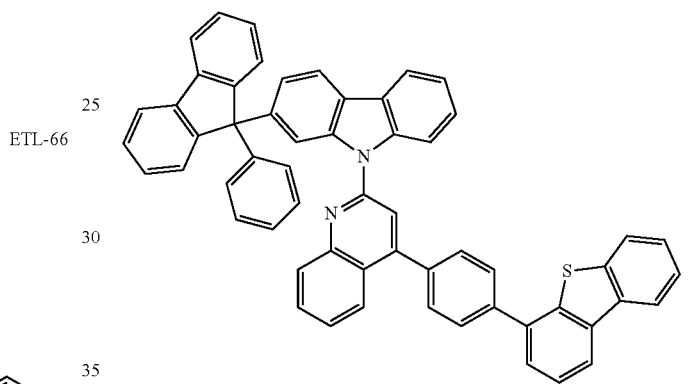
ETL-69
ETL-70
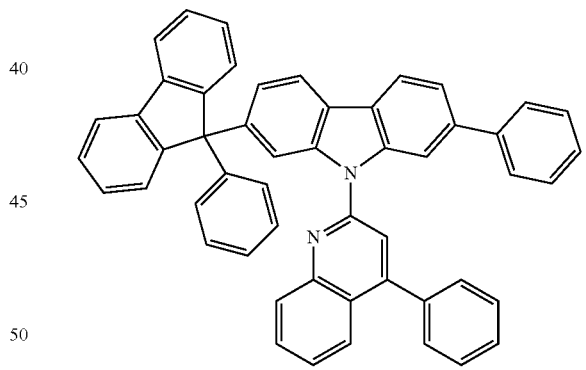
ETL-71
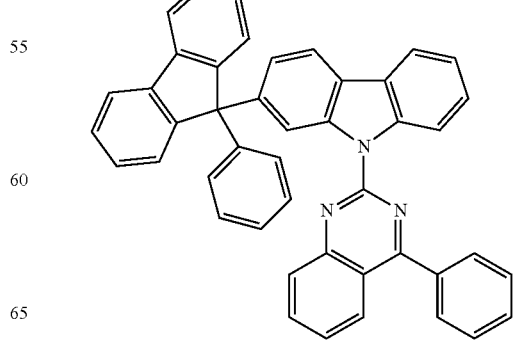

ETL-72
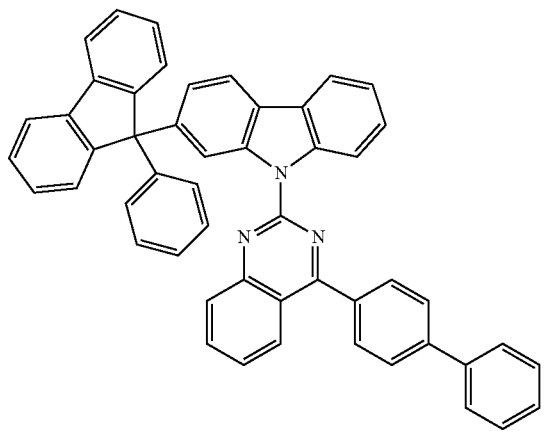
ETL-73
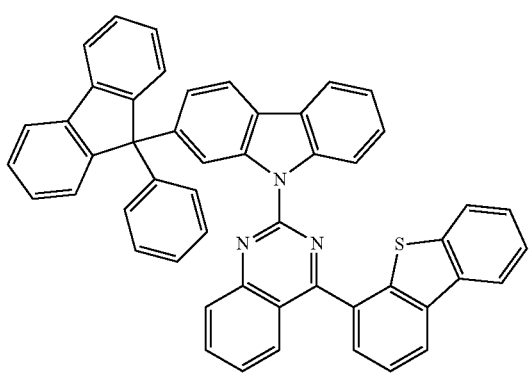
ETL-74
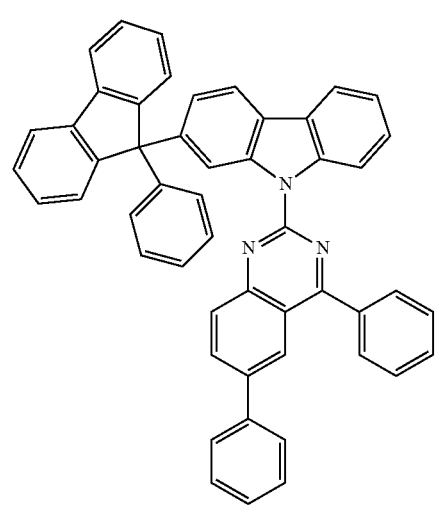
ETL-75
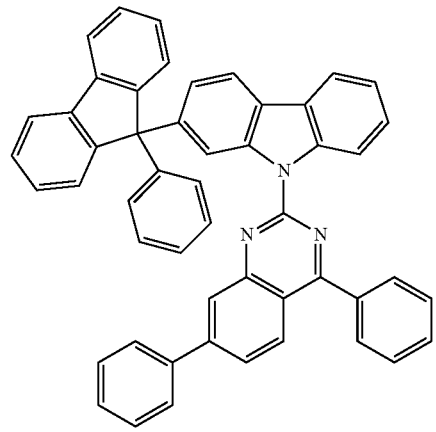
ETL-76
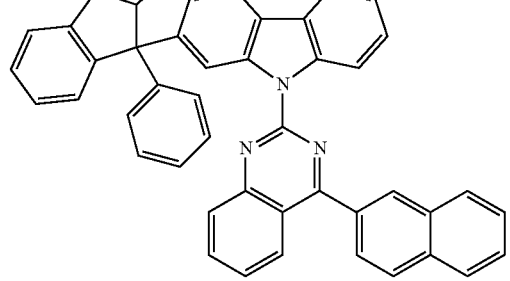
ETL-77

ETL-78
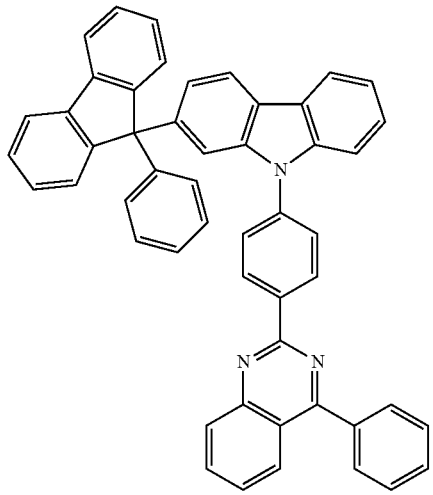
ETL-79
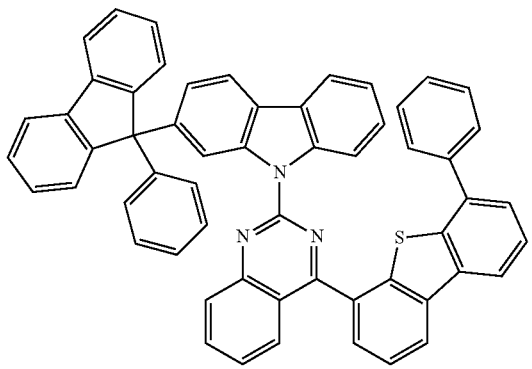
ETL-80
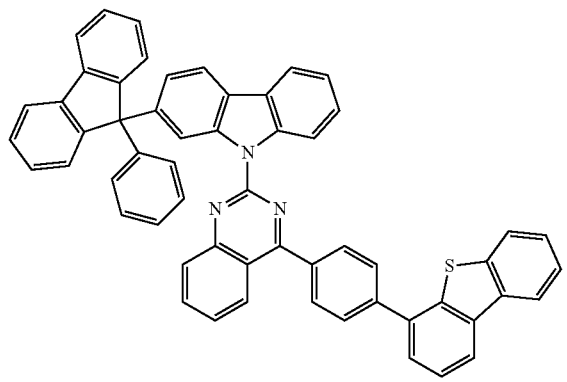
ETL-81
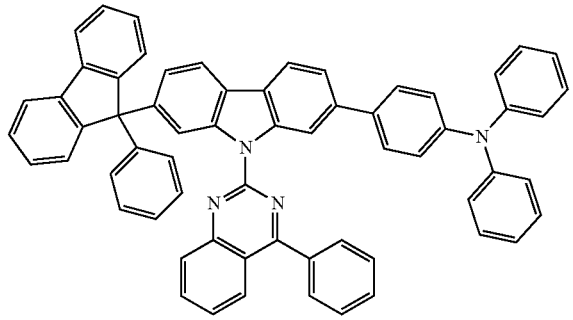
ETL-82
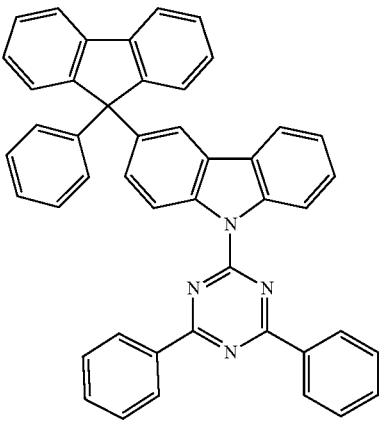
ETL-83
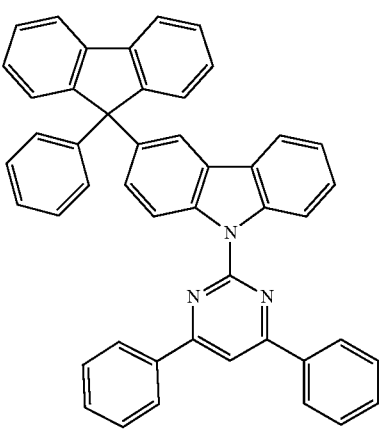
ETL-84
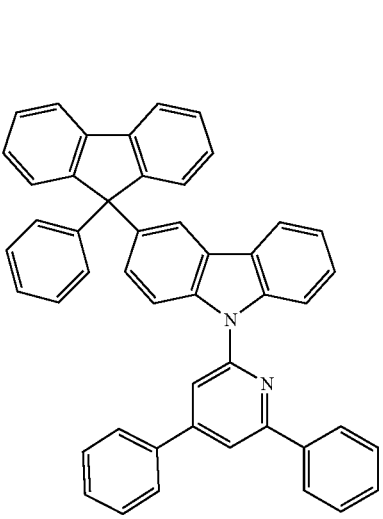

ETL-85
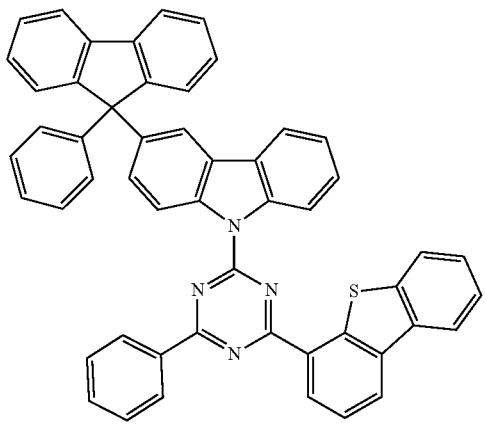
ETL-86
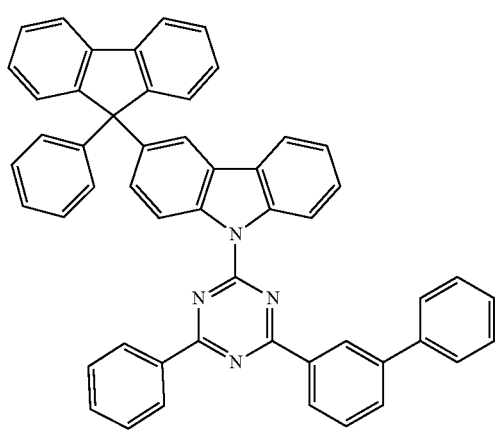
ETL-87
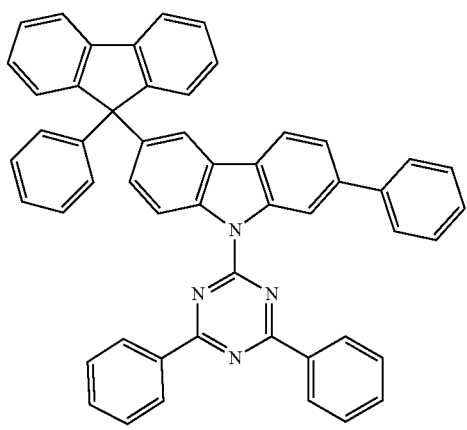
ETL-88
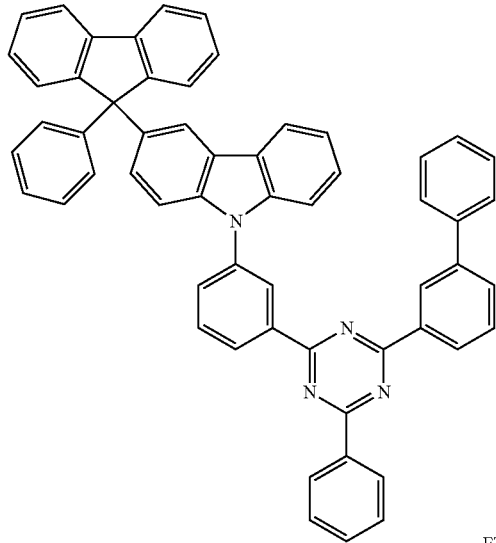
ETL-89
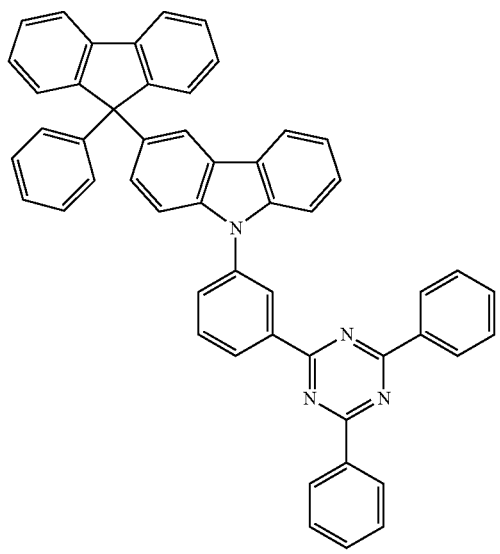
ETL-90
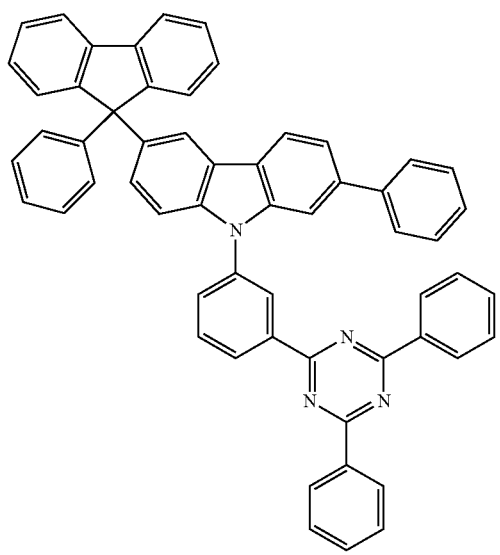

ETL-91
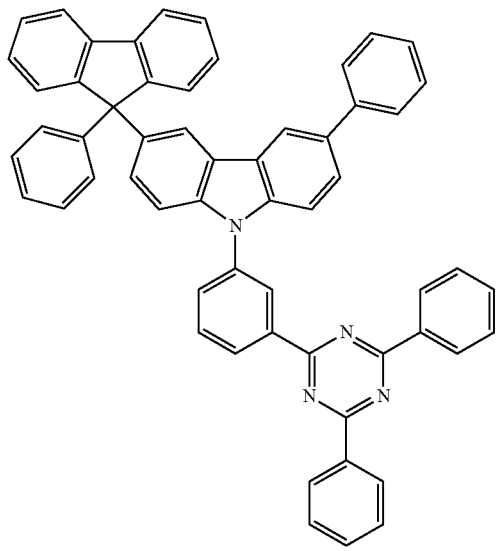
ETL-92
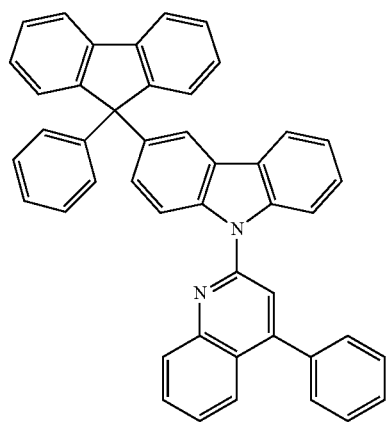
ETL-93
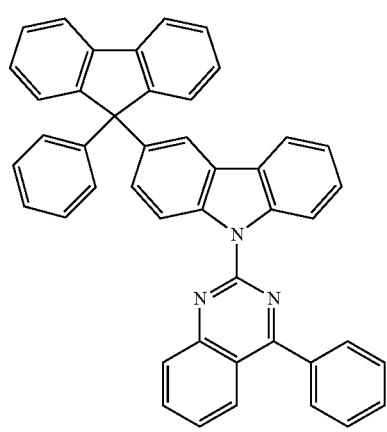
ETL-94
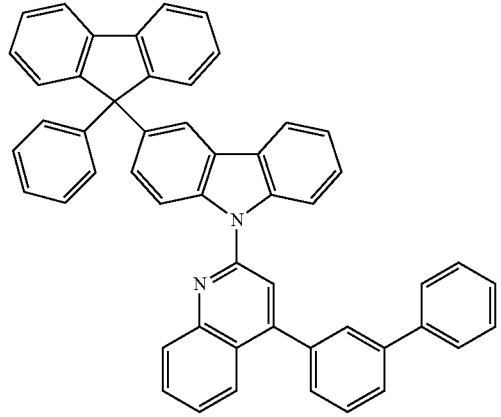
ETL-95
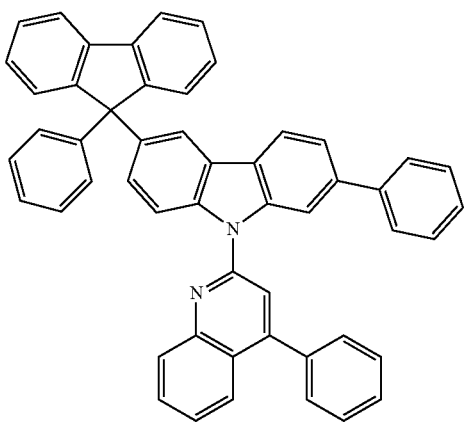
ETL-96
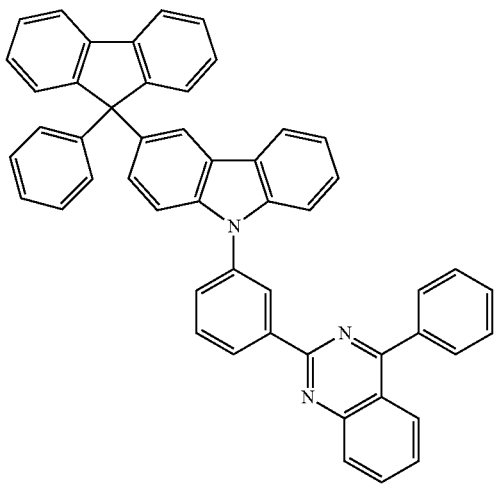

ETL-97
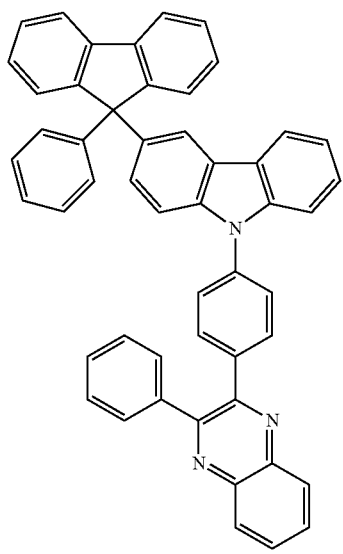
ETL-98
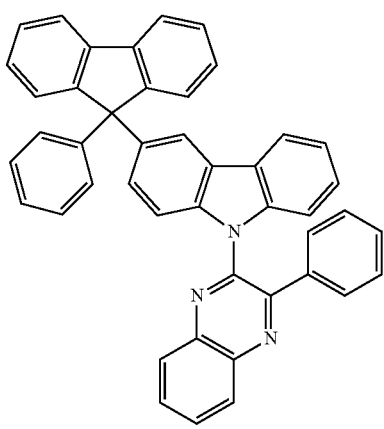
ETL-99
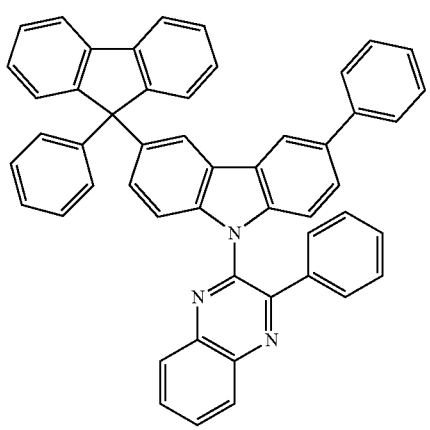
ETL-100
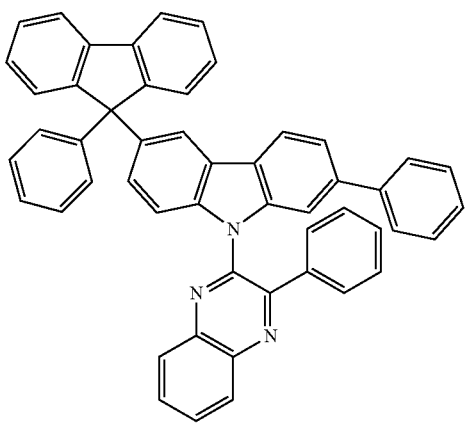
ETL-101
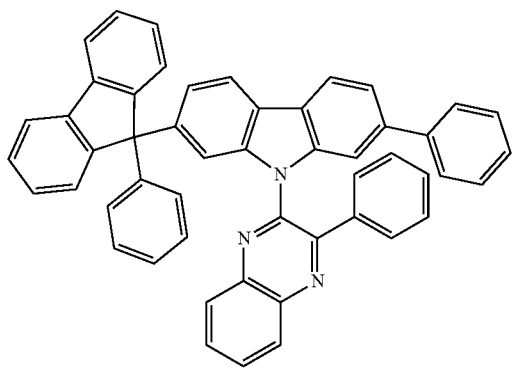
ETL-102
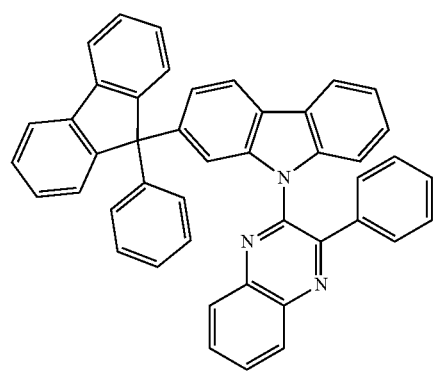

ETL-103
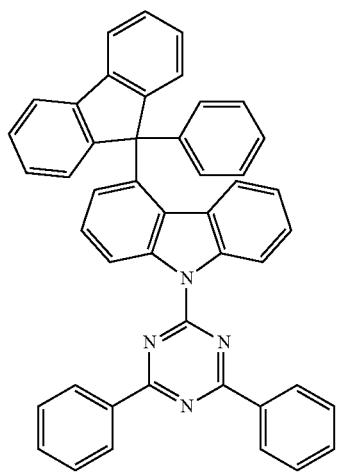
ETL-104
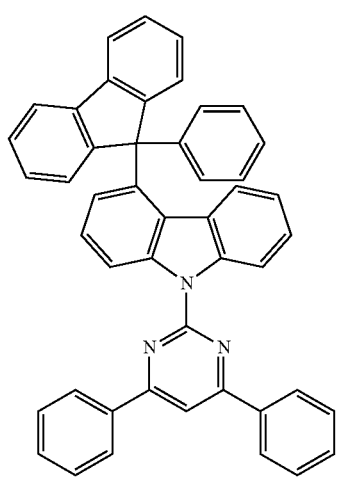
ETL-105
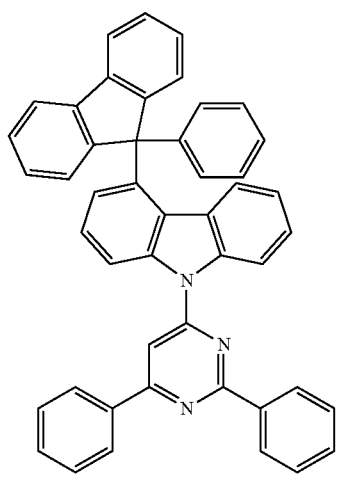
ETL-106
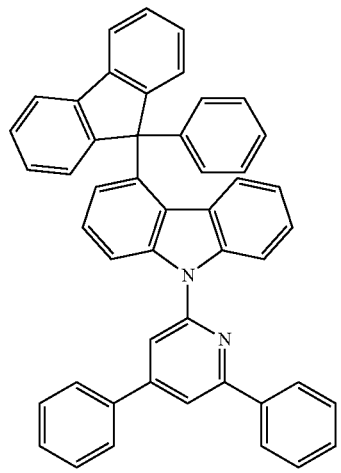
ETL-107
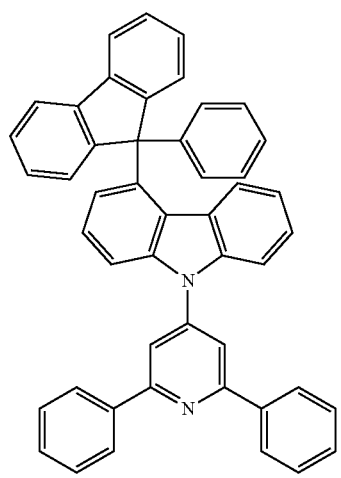
ETL-108
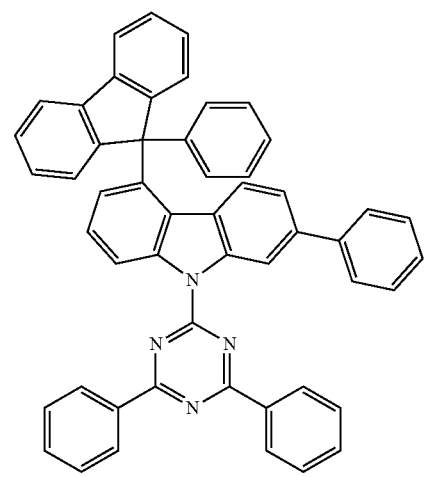

ETL-109
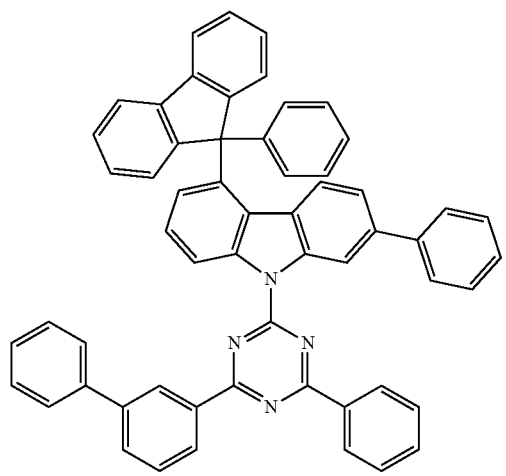
ETL-110
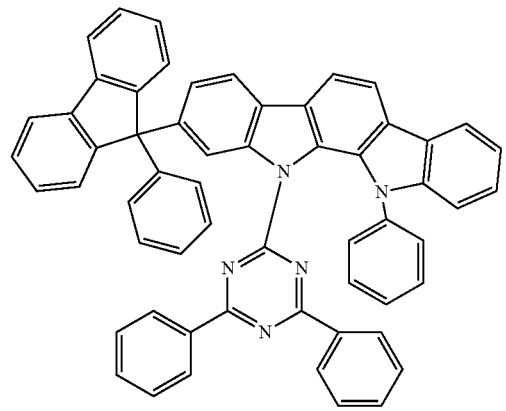
ETL-111
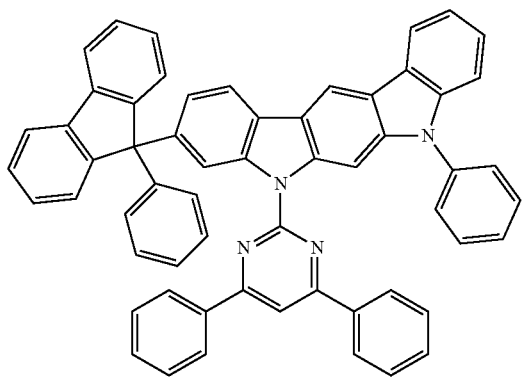
ETL-112
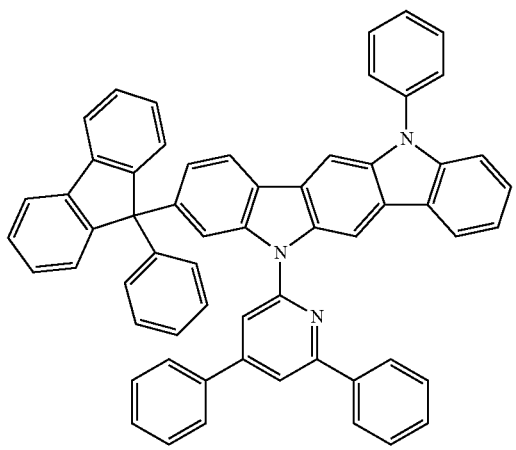
ETL-113
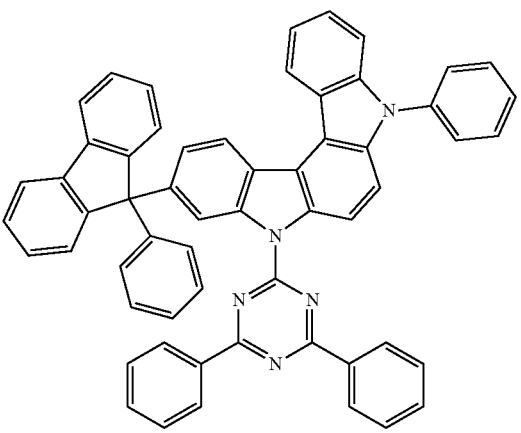
ETL-114
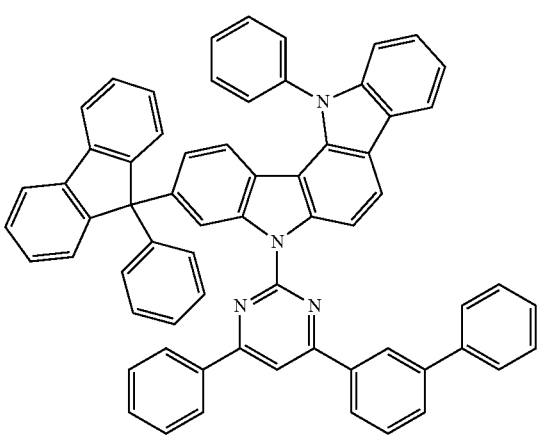

ETL-115
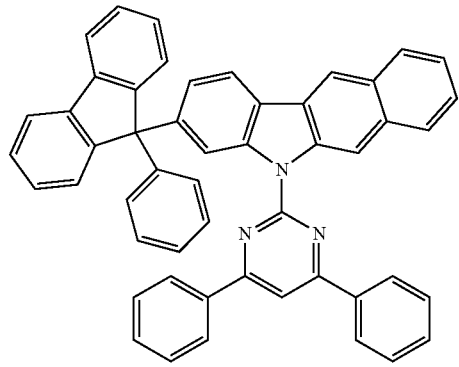
ETL-118
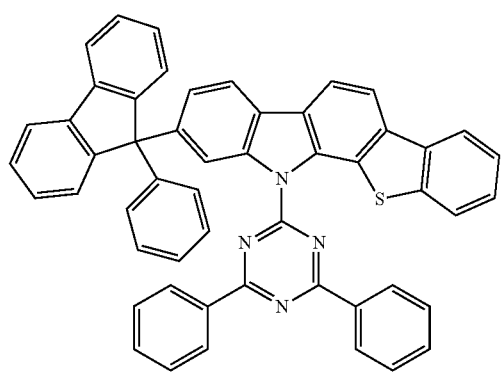
ETL-116
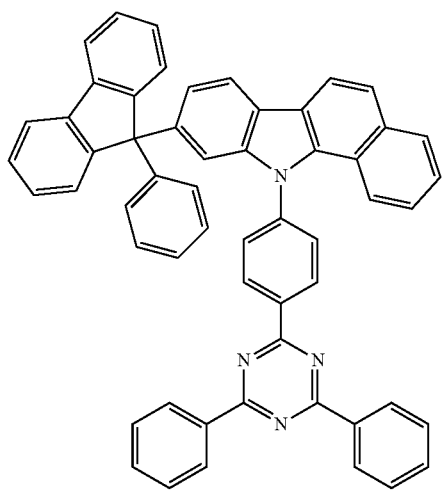
ETL-119
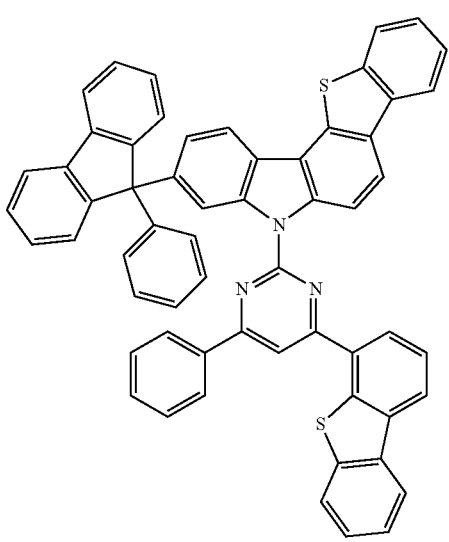
ETL-117
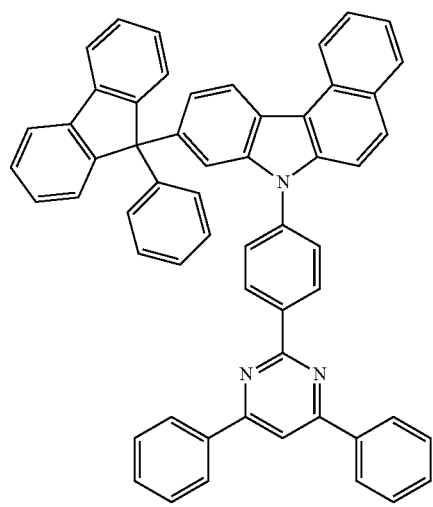
ETL-120
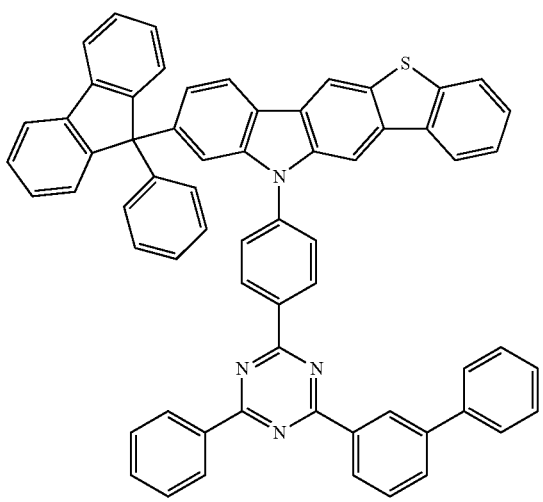

-continued
ETL-121
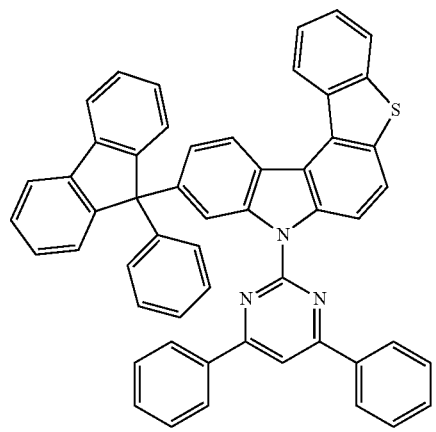
ETL-122
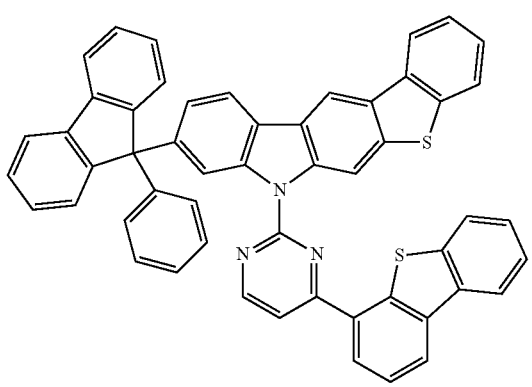
ETL-123
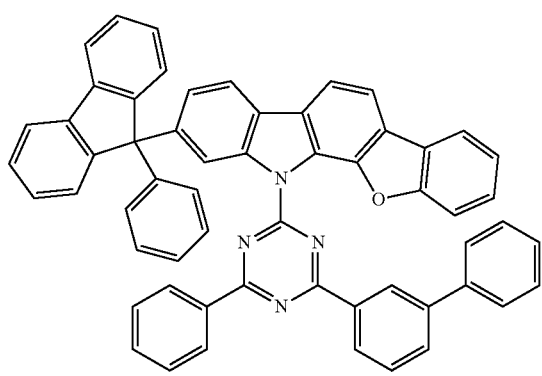
ETL-124
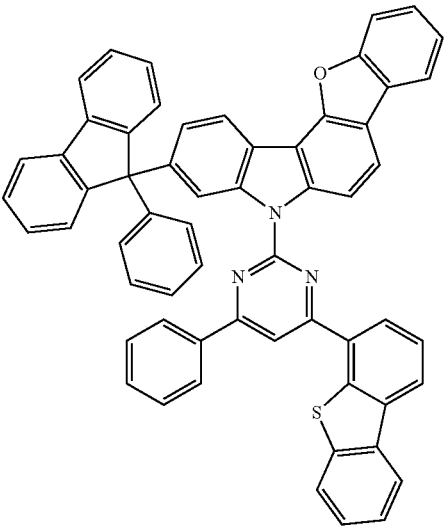
ETL-125
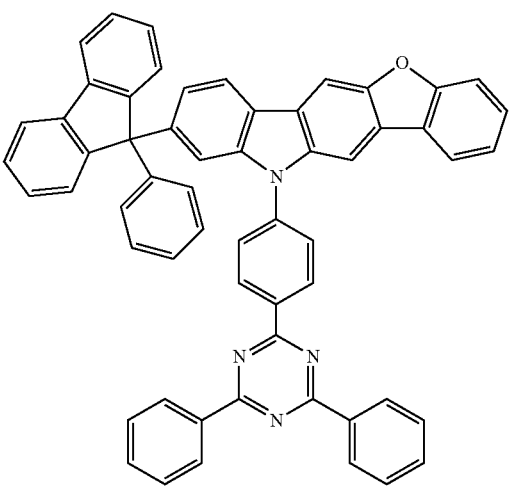
ETL-126
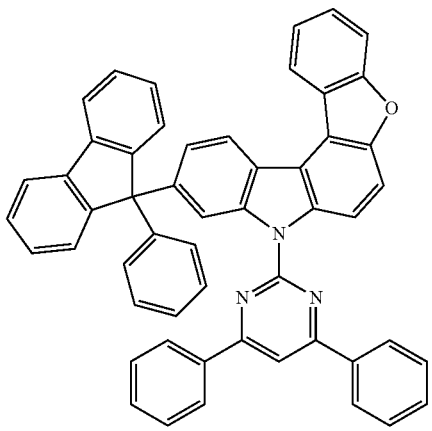

ETL-127
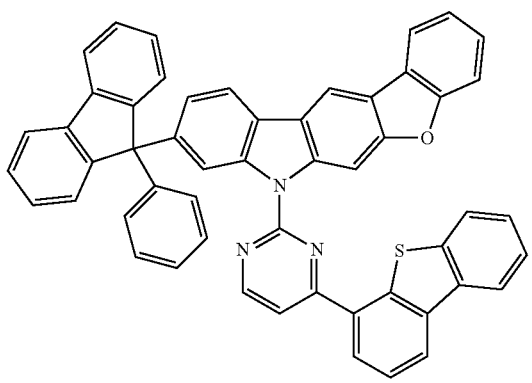
ETL-128
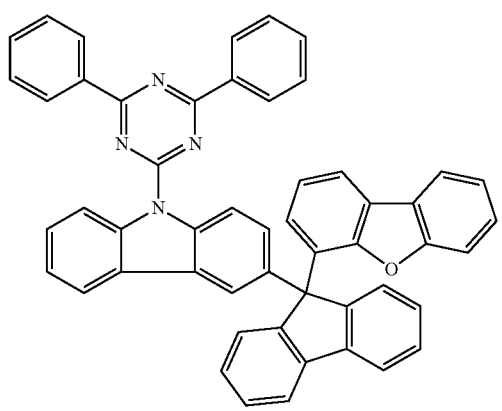
ETL-129
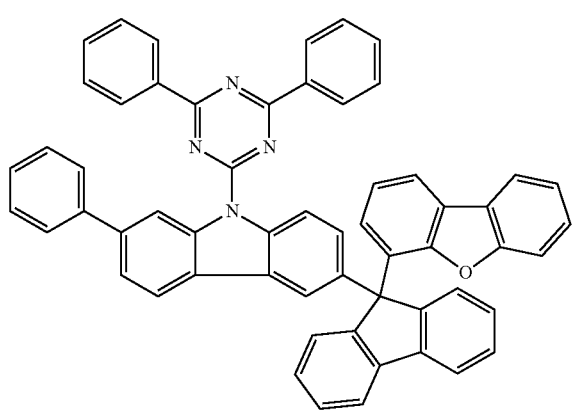
ETL-130
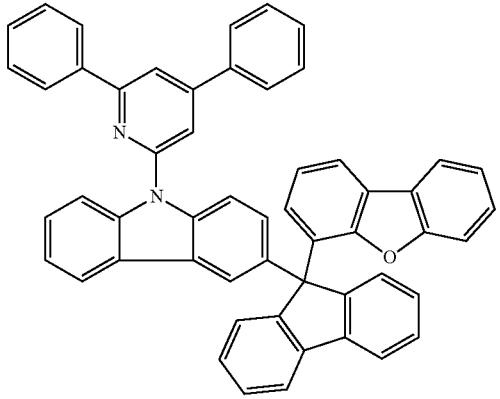
ETL-131
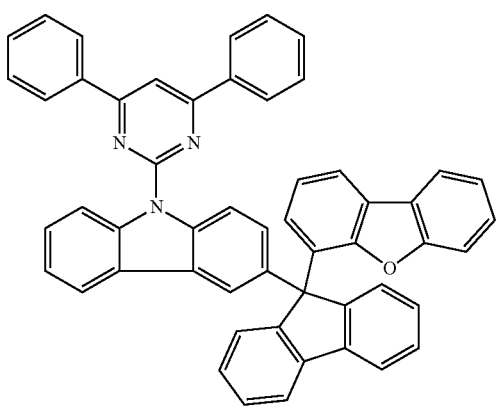
ETL-132
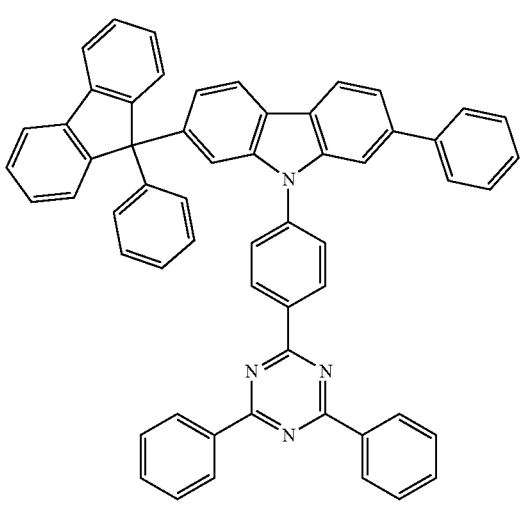

ETL-133
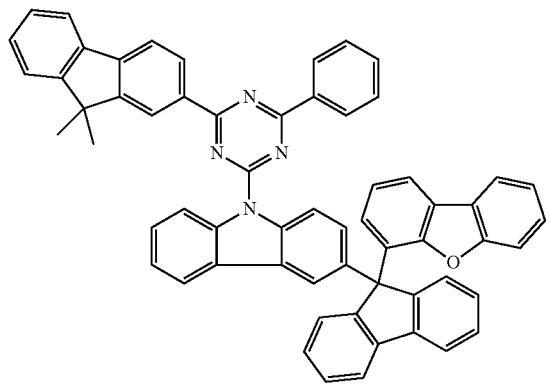
ETL-136
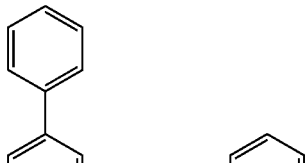
ETL-134
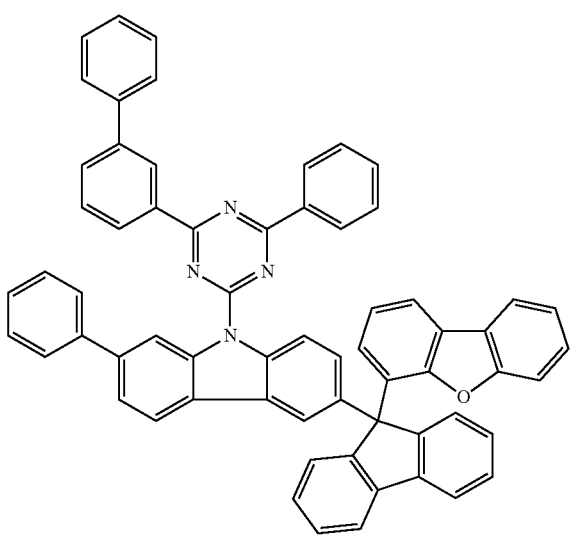
ETL-137
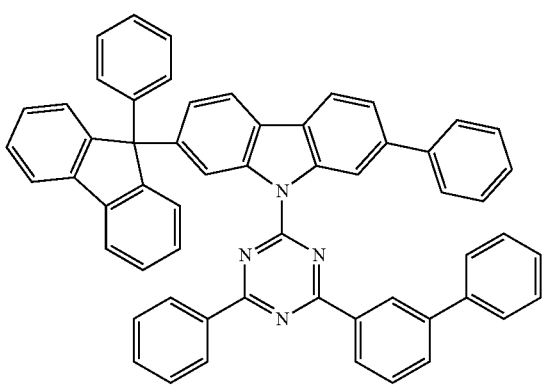
ETL-135
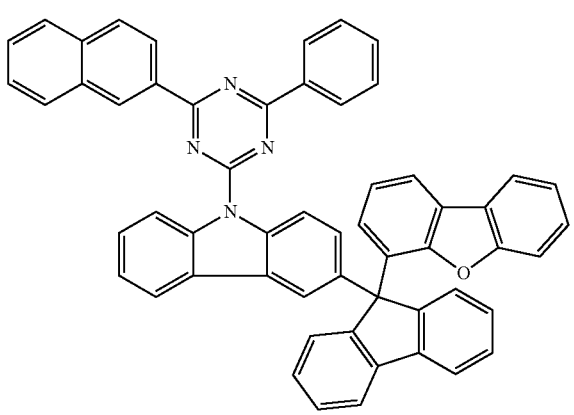
The compound of formula 1 as an electron transport material according to the present invention can be prepared by known methods to one skilled in the art, and can be prepared, for example, according to the following reaction schemes 1 to 3:
Reaction scheme 1
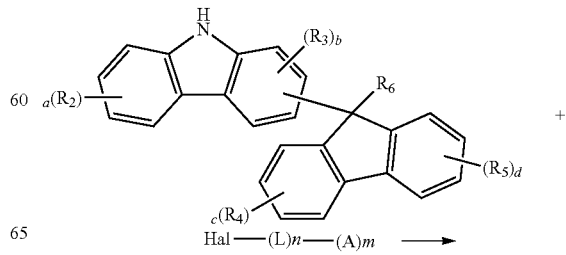

-continued

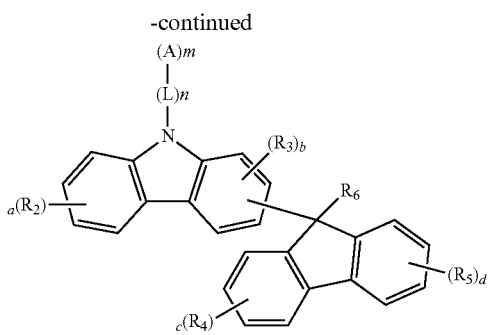

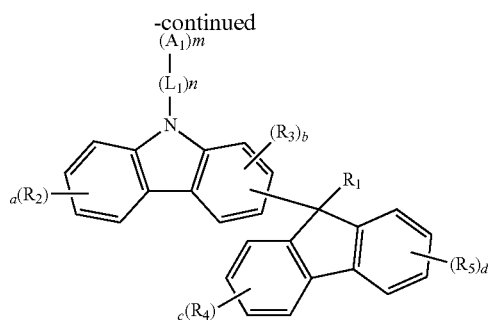

wherein

A and L are the same as $A_1$ and $L_1$ defined in formula 1, respectively; $A_1$, $L_1$, $R_1$ to $R_6$, a, b, c, d, m, and n are as defined in formula 1; and Hal represents a halogen.

The present invention further provides an electron transport material comprising the compound of formula 1, and an organic EL device comprising the material. An electron transport material can be comprised of the compound of formula 1 alone, or can be a mixture or composition for an electron transport layer which further comprises a conventional material generally included in electron transport materials.

The present invention provides an organic EL device comprising an anode, a cathode, and at least one organic layer between the two electrodes, wherein the organic layer comprises a light-emitting layer which contains host and dopant compounds. A light-emitting layer emitting light may be a single layer or multi-layers having two or more layers. The doping concentration of dopant compounds to host compounds in a light-emitting layer is preferably less than 20 wt %.

Furthermore, the present invention provides an organic EL device comprising an electron transport material comprising the compound of formula 1 and a reducing dopant. The organic EL device of the present invention may comprise an electron transport material in the organic layer and use a reducing dopant in a light-emitting layer. The reducing dopant is one or more selected from the group consisting of an alkaline metal, an alkaline earth metal, a rare-earth metal, an oxide of an alkaline metal, a halide of an alkaline metal, an oxide of an alkaline earth metal, a halide of an alkaline earth metal, an oxide of a rare-earth metal, a halide of a rare-earth metal, an organic complex of an alkaline metal, an organic complex of an alkaline earth metal, and an organic complex of a rare-earth metal.

The organic EL device of the present invention may further include at least one compound selected from the group consisting of arylamine-based compounds and styrylarylamine-based compounds in the organic layer.

In the organic EL device of the present invention, an organic layer may further comprise at least one metal selected from the group consisting of metals of Group 1, metals of Group 2, transition metals of the $4^{th}$ period, transition metals of the $5^{th}$ period, lanthanides, and organic metals of d-transition elements of the Periodic Table, or at least one complex compound comprising the metal.

Preferably, in the organic EL device of the present invention, at least one layer (hereinafter, "a surface layer") selected from a chalcogenide layer, a metal halide layer, and a metal oxide layer may be placed on an inner surface(s) of one or both electrode(s). Specifically, it is preferred that a chalcogenide (including oxides) layer of silicon or aluminum is placed on an anode surface of a light-emitting Reaction scheme 2

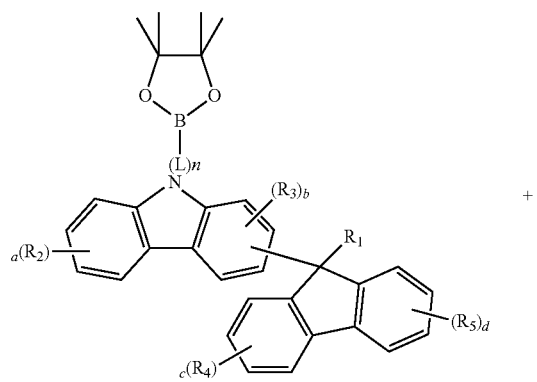

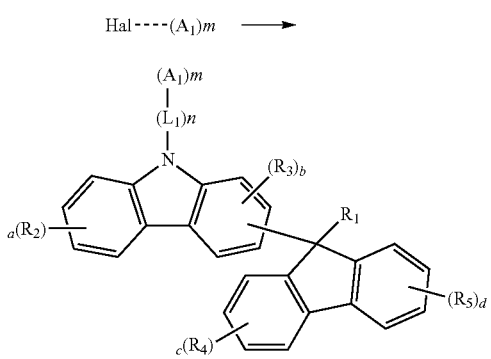

Reaction scheme 3

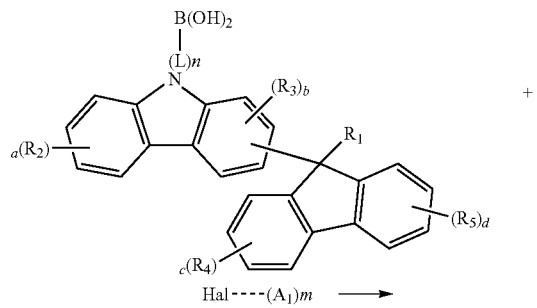

medium layer, and a metal halide layer or metal oxide layer is placed on a cathode surface of an electroluminescent medium layer. The surface layer provides operating stability for the organic EL device. Preferably, the chalcogenide includes $SiO_X(1≤X≤2)$, $AlO_X(1≤X≤1.5)$, SiON, SiAlON, etc.; the metal halide includes LiF, $MgF_2$, $CaF_2$, a rare earth metal fluoride, etc.; and the metal oxide includes $Cs_2O$, $Li_2O$, MgO, SrO, BaO, CaO, etc.

A hole injection layer (HIL), a hole transport layer (HTL), an electron blocking layer (EBL), or their combinations can be used between an anode and a light-emitting layer. A hole injection layer may be multi-layers in order to lower a hole injection barrier (or hole injection voltage) from an anode to a hole transport layer or electron blocking layer, wherein each of the multi-layers simultaneously may use two compounds. A hole transport layer or an electron blocking layer may also be multi-layers.

An electron buffer layer, a hole blocking layer (HBL), an electron transport layer (ETL), an electron injection layer (EIL), or their combinations can be used between a light-emitting layer and a cathode. An electron buffer layer may be multi-layers in order to control the injection of an electron and improve interface properties between a light-emitting layer and an electron injection layer, wherein each of the multi-layers simultaneously may use two compounds. A hole blocking layer or a electron transport layer may also be multi-layers, wherein each of the multi-layers may use a multi-component of compounds.

Preferably, in the organic EL device of the present invention, a mixed region of an electron transport compound and a reductive dopant, or a mixed region of a hole transport compound and an oxidative dopant may be placed on at least one surface of a pair of electrodes. In this case, an electron transport compound is reduced to an anion, and thus it becomes easier to inject and transport electrons from the mixed region to a light-emitting medium. Furthermore, a hole transport compound is oxidized to a cation, and thus it becomes easier to inject and transport holes from the mixed region to a light-emitting medium. Preferably, an oxidative dopant includes various Lewis acids and acceptor compounds; and a reductive dopant includes alkali metals, alkali metal compounds, alkaline earth metals, rare-earth metals, and mixtures thereof. A reductive dopant layer may be employed as a charge-generating layer to prepare an organic EL device having two or more light-emitting layers and emitting white light.

In order to form each layer constituting the organic EL device of the present invention, dry film-forming methods, such as vacuum deposition, sputtering, plasma, ion plating methods, etc., or wet film-forming methods, such as spin coating, dip coating, flow coating methods, etc., can be used.

When using a wet film-forming method, a thin film is formed by dissolving or dispersing the material constituting each layer in suitable solvents, such as ethanol, chloroform, tetrahydrofuran, dioxane, etc. The solvents are not specifically limited as long as the material constituting each layer is soluble or dispersible in the solvents, which do not cause any problems in forming a layer.

Hereinafter, the compounds of the present invention, the preparation method thereof, and luminous properties of devices comprising the compounds as an electron transport material will be explained in detail with reference to the following examples:

Example 1

Preparation of Compound ETL-34

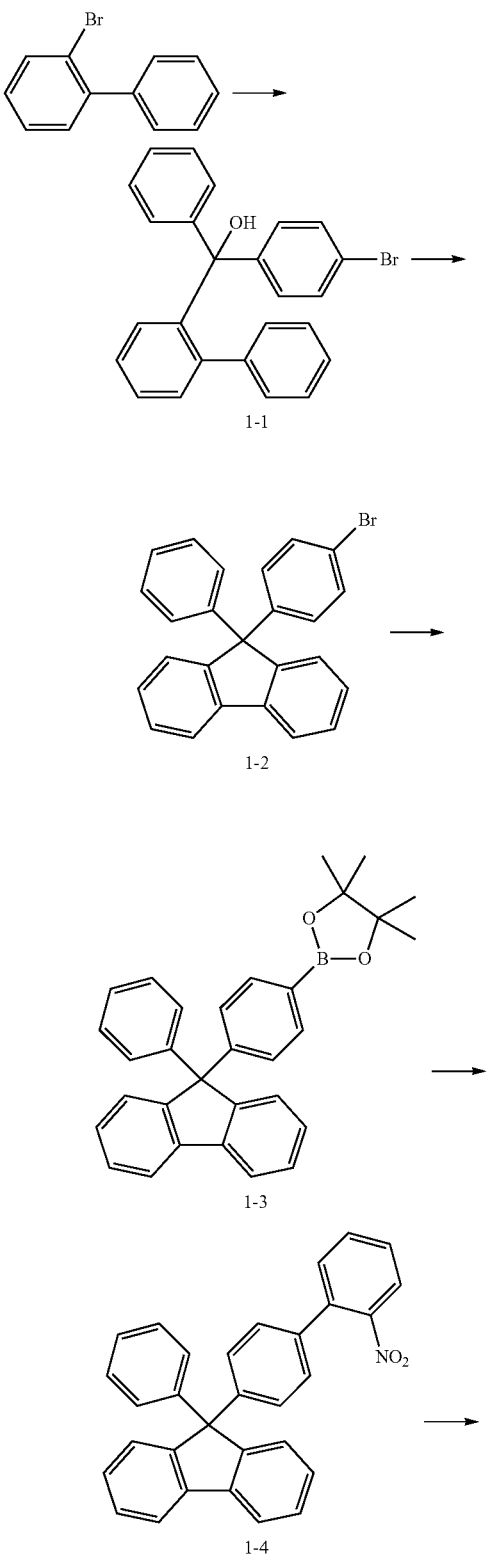

1-1

1-2

1-3

1-4

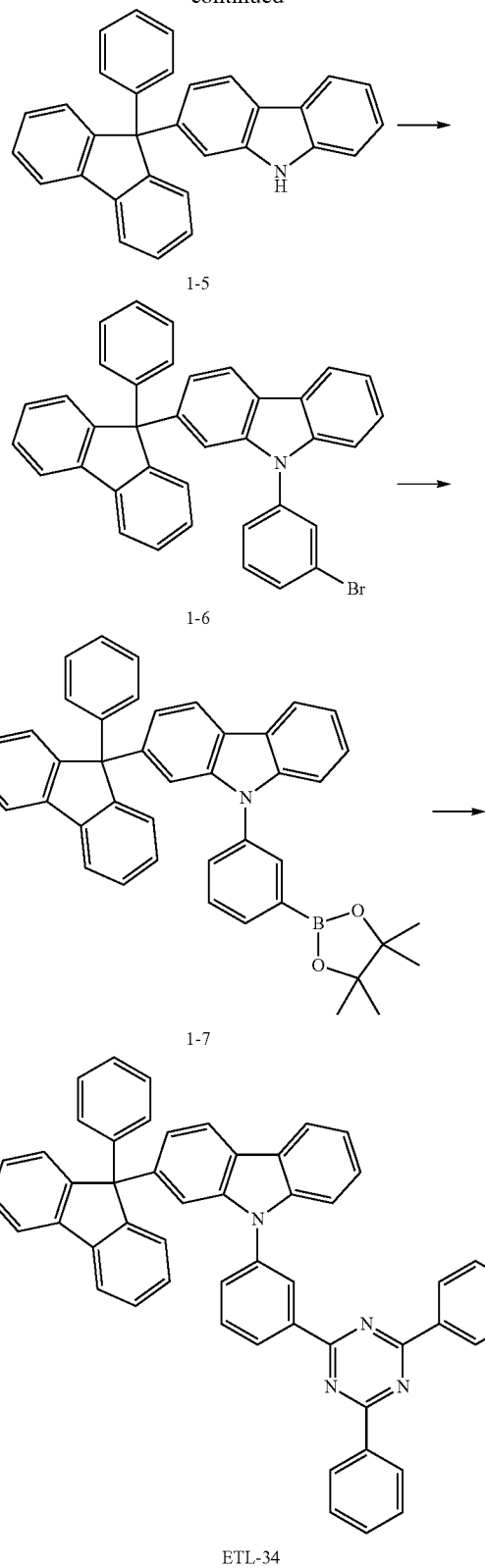

(RBF) and the mixture was cooled to −78° C. 2.5 M n-butyl lithium (103.0 mL, 257.0 mmol) was added to the mixture. After 2 hrs, (4-bromophenyl)(phenyl)methanone (56.0 g, 214.0 mmol) was added to the mixture. After 17 hrs, the mixture was extracted with methylene chloride (MC) and H$_2$O, and the MC layer was dried over MgSO$_4$ and was concentrated to obtain compound 1-1.

Compound 1-1, hydrochloric acid (100.0 mL) and acetic acid (1 L) were stirred under reflux in a 3 L RBF. After 14 hrs, the resulting solid was filtered. The filtered solid was dissolved in chloroform (CHCl$_3$) and was separated through column chromatography to obtain compound 1-2 (35.0 g, 42%).

Preparation of Compound 1-3

Compound 1-2 (35.0 g, 89.0 mmol), bis(pinacolato)diborane (27.0 g, 106.0 mmol), bis(triphenylphosphine)palladium(II) dichloride (Pd(PPh$_3$)$_2$Cl$_2$) (3.1 g, 4.45 mmol), potassium acetate (KOAc) (22.0 g, 222.0 mmol), and 1,4-dioxane (445.0 mL) were stirred under reflux in a 1 L RBF. After 3 hrs, the mixture was extracted with dichloromethane (DCM) and H$_2$O. The DCM layer was dried over MgSO$_4$ and was filtered. The obtained solid was dissolved in CHCl$_3$ and was separated through column chromatography to obtain compound 1-3 (22.0 g, 56%).

Preparation of Compound 1-4

Compound 1-3 (22.0 g, 50.0 mmol), 2-bromonitrobenzene (12.0 g, 60.0 mmol), tetrakis(triphenylphosphine)palladium(0) (Pd(PPh$_3$)$_4$) (1.7 g, 1.5 mmol), K$_2$CO$_3$ (13.7 g, 99.4 mmol), toluene (100.0 mL), ethanol (EtOH) (25.0 mL), and H$_2$O (25.0 L) were stirred under reflux in a 500 mL RBF. After 5 hrs, the mixture was extracted with DCM and H$_2$O, and the DCM layer was dried over MgSO$_4$ and was filtered. The obtained solid was dissolved in CHCl$_3$ and was separated through column chromatography to obtain compound 1-4 (15.0 g, 70%).

Preparation of Compound 1-5

Compound 1-4 (15.0 g, 35.0 mmol), triethylphosphite (P(OEt)$_3$) (100.0 mL), and 1,2-dichlorobenzene (1,2-DCB) (50.0 mL) were stirred under reflux in a 500 mL RBF. After 13 hrs, the solvent was distilled out, and the resulting product was dissolved in CHCl$_3$ and was separated through column chromatography to obtain compound 1-5 (8.42 g, 59%).

Preparation of Compound 1-6

Compound 1-5 (8.4 g, 21.0 mmol), 1-bromo-3-iodobenzene (8.7 g, 31.0 mmol), CuI (2.0 g, 10.3 mmol), ethylenediamine (EDA) (1.4 mL, 21.0 mmol), K$_3$PO$_4$ (13.0 g, 62.0 mmol), and toluene (103.0 mL) were stirred under reflux in a 500 mL RBF for 23 hrs. Upon completing the reaction, the mixture was cooled to room temperature and was extracted with DCM and H$_2$O. The DCM layer was dried over MgSO$_4$ and was concentrated under reduced pressure. The obtained solution was separated through column chromatography to obtain compound 1-6 (9.5 g, 94%).

Preparation of Compound 1-7

Compound 1-6 (9.5 g, 19.5 mmol), bis(pinacolato)diborane (6.4 g, 25.0 mmol), Pd(PPh$_3$)$_2$Cl$_2$ (684.0 mg, 0.97 mmol), KOAc (4.8 g, 49.0 mmol), and 1,4-dioxane (196.0 mL) were stirred under reflux in a 500 mL RBF. After 6 hrs, the mixture was extracted with DCM and H₂O. The DCM layer was dried over MgSO₄ and was filtered. The obtained solid was dissolved in CHCl₃ and was separated through column chromatography to obtain compound 1-7 (8.0 g, 69%).

Preparation of Compound ETL-34

Compound 1-7 (8.0 g, 13.0 mmol), 2-chloro-4,6-diphenyl-1,3,5-triazine (4.2 g, 15.7 mmol), Pd(PPh₃)₄ (454.0 mg, 0.39 mmol), K₂CO₃ (3.6 g, 26.0 mmol), toluene (30.0 mL), EtOH (7.0 mL), and H₂O (7.0 mL) were stirred under reflux in a 250 mL RBF. After 3 hrs, the mixture was extracted with DCM and H₂O. The DCM layer was dried over MgSO₄ and was filtered. The obtained solid was dissolved in CHCl₃ and was separated through column chromatography to obtain compound ETL-34 (3.95 g, 42%).

m.p. 288° C., UV 290 nm (in toluene), PL 430 nm (in toluene), MS/EIMS 714.28

Example 2

Preparation of Compound ETL-57

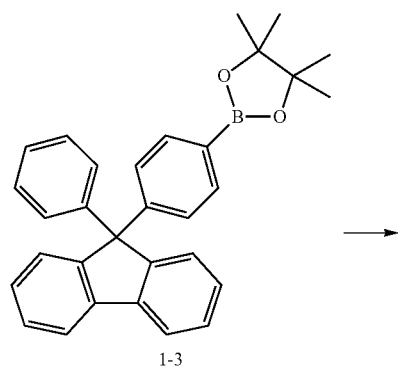

1-3

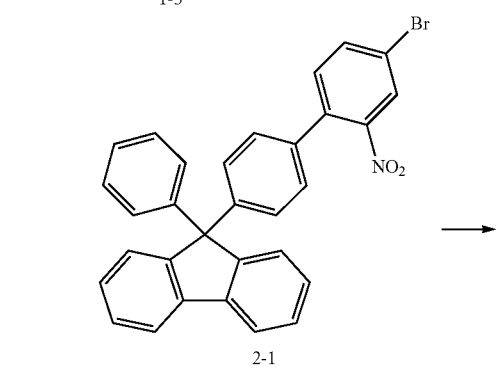

2-1

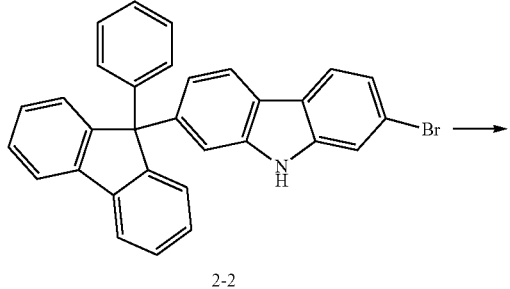

2-2

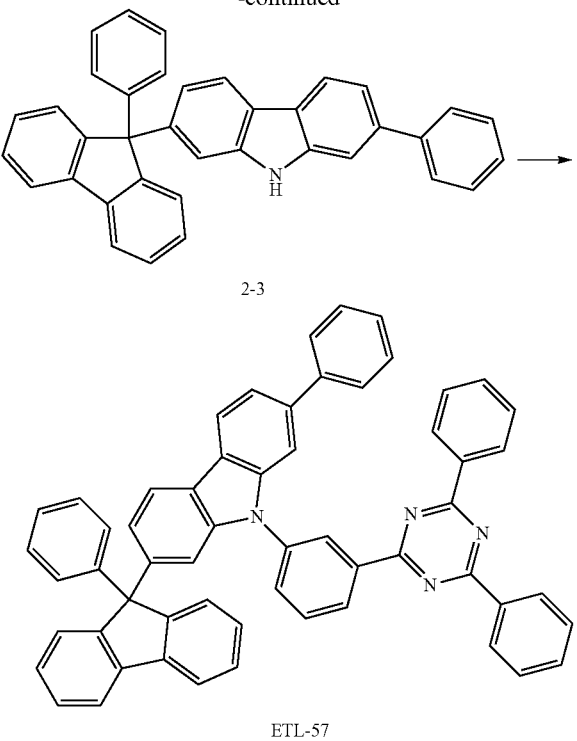

2-3

ETL-57

Preparation of Compound 2-1

Compound 1-3 (35.0 g, 78.0 mmol), 2,5-dibromonitrobenzene (26.2 g, 93.0 mmol), Pd(PPh₃)₄ (3.6 g, 3.1 mmol), and Na₂CO₃ (20.6 g, 195.0 mmol) were dissolved in toluene (400.0 mL), EtOH (50.0 mL), and H₂O (100.0 L) in a 2 L RBF and were stirred overnight at 130° C. After working-up the reaction mixture with ethyl acetate (EA)/H₂O, the mixture was dehydrated with MgSO₄ and was distilled under reduced pressure. The crude product was separated through column chromatography by using methylene chloride (MC):hexane (Hx) to obtain compound 2-1 (30.0 g, 75%) as a solid.

Preparation of Compound 2-2

Compound 2-1 (30.0 g, 57.8 mmol), triethylphosphite (200.0 mL), and 1,2-DCB (200.0 mL) were stirred in a 1 L RBF at 150° C. for 2 hrs. The reaction mixture was distilled to obtain a solid. The crude product was separated through column chromatography by using MC:Hx to obtain compound 2-2 (19.0 g, 68%) as a white solid.

Preparation of Compound 2-3

Compound 2-2 (22.7 g, 47.0 mmol), phenylboronic acid (5.7 g, 47.0 mmol), Pd(PPh₃)₄ (1.8 g, 1.5 mmol), K₂CO₃ (13.5 g, 97.0 mmol), toluene (200.0 mL), EtOH (50.0 mL), and H₂O (50.0 mL) were stirred in a 500 mL RBF at 120° C. for 2.5 hrs. After working-up the reaction mixture with EA/H₂O, the mixture was dehydrated with MgSO₄ and was distilled under reduced pressure. The crude product was separated through column chromatography by using MC:Hx to obtain compound 2-3 (16.0 g, 84%) as a white solid.

Preparation of Compound ETL-57

Compound 2-3 (10.0 g, 20.6 mmol), 2-(3-bromophenyl)-4,6-diphenyl-1,3,5-triazine (9.6 g, 24.8 mmol), palladium (II) acetate (Pd(OAc)$_2$) (232.0 mg, 1.0 mmol), 2-dicyclohexylphosphino-2',6'-dimethoxybiphenyl (s-phos) (850.0 mg, 2.0 mmol), sodium tert-butoxide (NaOtBu) (5.0 g, 51.6 mmol), and o-xylene (200.0 mL) were stirred in a 500 mL RBF at 180° C. for 2 hrs. After working-up the reaction mixture with EA/H$_2$O, the mixture was dehydrated with MgSO$_4$ and was distilled under reduced pressure. The crude product was separated through column chromatography by using MC:Hx to obtain compound ETL-57 (7.3 g, 45%) as a white solid.

m.p. 312° C., UV 344 nm (in toluene), PL 427 nm (in toluene), MS/EIMS 791

Example 3

Preparation of Compound ETL-90

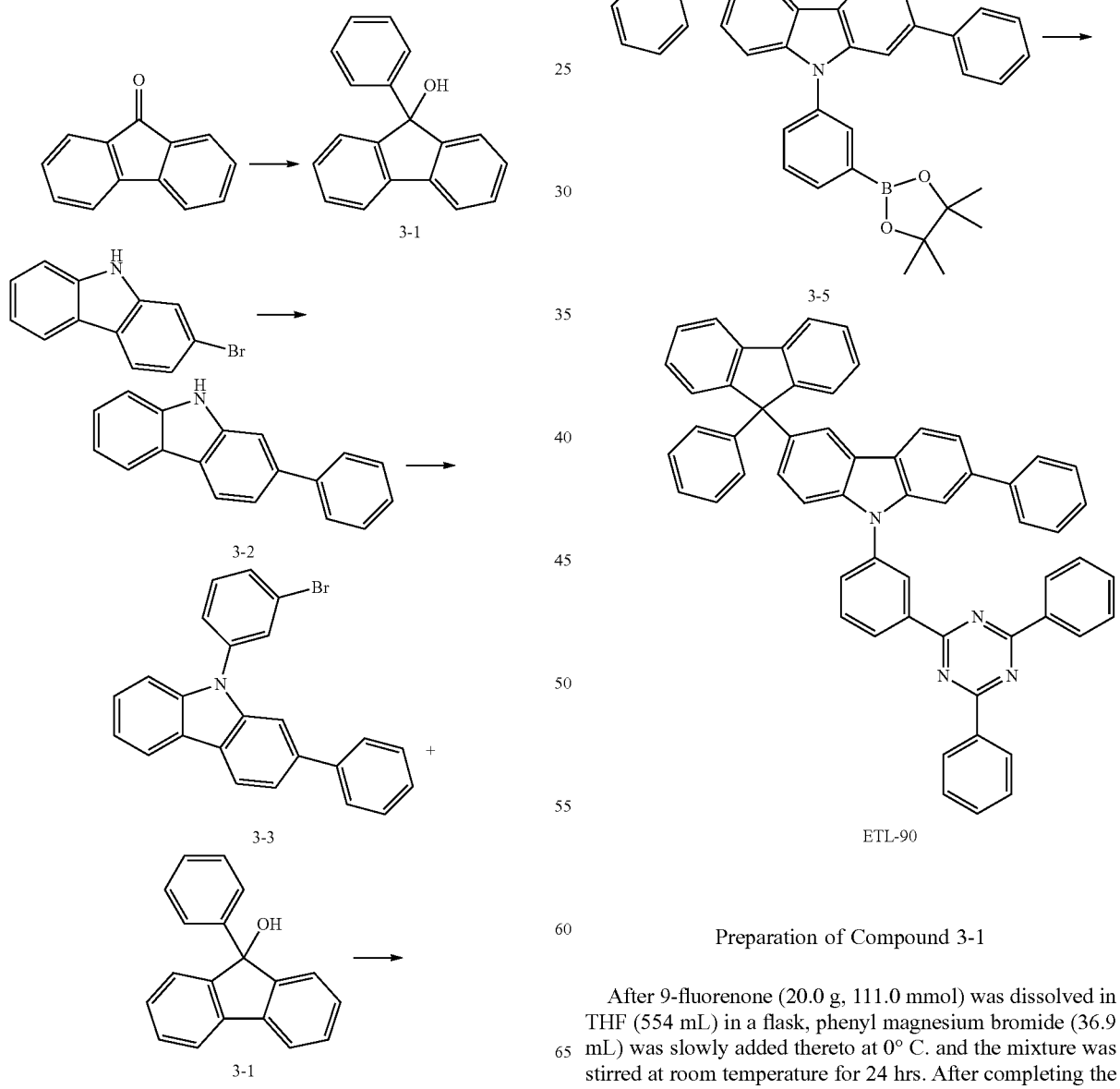

Preparation of Compound 3-1

After 9-fluorenone (20.0 g, 111.0 mmol) was dissolved in THF (554 mL) in a flask, phenyl magnesium bromide (36.9 mL) was slowly added thereto at 0° C. and the mixture was stirred at room temperature for 24 hrs. After completing the reaction, the organic layer was extracted with EA, was dried by removing the remaining moisture with MgSO$_4$, and was separated through column chromatography to obtain compound 3-1 (20.0 g, 70%).

Preparation of Compound 3-2

2-Bromo-9H-carbazole (20.0 g, 81.2 mmol), phenylboronic acid (11.9 g, 97.5 mmol), Pd(PPh$_3$)$_4$ (4.7 g, 4.06 mmol), 2M K$_2$CO$_3$ (121.0 mL), toluene (250.0 mL), and EtOH (121.0 mL) were stirred under reflux in a flask for 5 hrs. After completing the reaction, the organic layer was extracted with EA, was dried by removing the remaining moisture with MgSO$_4$, and was separated through column chromatography to obtain compound 3-2 (17.0 g, 86%).

Preparation of Compound 3-3

Compound 3-2 (17.0 g, 70.0 mmol), 1-iodo-3-bromobenzene (17.7 mL, 140.0 mmol), CuI (6.6 g, 35.0 mmol), and K$_3$PO$_4$ (44.5 g, 210.0 mmol) were dissolved in EDA (4.7 mL, 70.0 mmol) and toluene (350.0 mL) in a flask and were refluxed at 120° C. for 5 hrs. After completing the reaction, the organic layer was extracted with EA, was dried by removing the remaining moisture with MgSO$_4$, and was separated through column chromatography to obtain compound 3-3 (27.0 g, 97%).

Preparation of Compound 3-4

Compound 3-3 (27.0 g, 67.7 mmol) and compound 3-1 (17.5 g, 67.7 mmol) were dissolved in DCM (522.0 mL) in a flask. P$_2$O$_5$ (0.04 mL, 1.35 mmol) in methanesulfonic acid (MSA) was added to the mixture, and the mixture was stirred for 10 min. After completing the reaction, NaHCO$_3$ (aq) was added to the mixture. The organic layer was extracted with DCM, was dried by removing the remaining moisture with MgSO$_4$, and was separated through column chromatography to obtain compound 3-4 (40.0 g, 95%).

Preparation of Compound 3-5

Compound 3-4 (15.0 g, 23.4 mmol), 2-(3-bromophenyl)-4,6-diphenyl-1,3,5-triazine (6.6 g, 25.74 mmol), palladium (II) chloride (PdCl$_2$(PPh$_3$)$_4$) (659.0 mg, 0.94 mmol), and KOAc (10.0 g, 102.9 mmol) were dissolved in 1,4-dioxane (156.0 mL) in a flask. The mixture was refluxed at 120° C. for 4 hrs. After completing the reaction, the organic layer was extracted with EA, was dried by removing the remaining moisture with MgSO$_4$, and was separated through column chromatography to obtain compound 3-5 (10.6 g, 66%).

Preparation of Compound ETL-90

Compound 3-5 (10.6 g, 15.4 mmol), 2-chloro-4,6-diphenyl-1,3,5-triazine (3.8 g, 14.0 mmol), Pd(PPh$_3$)$_4$ (820.0 mg, 0.77 mmol), 2M K$_2$CO$_3$ (60.0 mL), EtOH (60.0 mL), and toluene (180.0 mL) were refluxed in a flask at 120° C. for 5 hrs. After completing the reaction, the organic layer was extracted with EA, was dried by removing the remaining moisture with MgSO$_4$, and was recrystallized by using EA and MeOH to obtain compound ETL-90 (4.0 g, 32.7%).

m.p. 256° C., UV 324 nm (in toluene), PL 439 nm (in toluene), MS/EIMS 790.95

Device Example 1

Production of an OLED Device by Using an Organic Compound for an Electron Transport Material According to the Present Invention An OLED device comprising an organic compound for an electron transport material of the present invention was produced as follows: A transparent electrode indium tin oxide (ITO) thin film (15 Ω/sq) on a glass substrate for an OLED device (GEOMATEC CO., LTD., Japan) was subjected to an ultrasonic washing with trichloroethylene, acetone, ethanol, and distilled water, sequentially, and was then stored in isopropanol. Next, the ITO substrate was mounted on a substrate holder of a vacuum vapor depositing apparatus. N$^4$,N$^{4'}$-diphenyl-N$^4$,N$^{4'}$-bis(9-phenyl-9H-carbazol-3-yl)-[1,1'-biphenyl]-4,4'-diamine was introduced into a cell of the vacuum vapor depositing apparatus, and the pressure in the chamber of the apparatus was then controlled to 10$^{-6}$ torr. Thereafter, an electric current was applied to the cell to evaporate the introduced material, thereby forming a hole injection layer 1 having a thickness of 60 nm on the ITO substrate. 1,4,5,8,9,12-hexaazatriphenylene-hexacarbonitrile was then introduced into another cell of the vacuum vapor depositing apparatus, and an electric current was applied to the cell to evaporate the introduced material, thereby forming a hole injection layer 2 having a thickness of 5 nm on hole injection layer 1. N-([1,1'-biphenyl]-4-yl)-9,9-dimethyl-N-(4-(9-phenyl-9H-carbazol-3-yl)phenyl)-9H-fluorene-2-amine was introduced into one cell of the vacuum vapor depositing apparatus. Thereafter, an electric current was applied to the cell to evaporate the introduced material, thereby forming a hole transport layer 1 having a thickness of 20 nm on hole injection layer 2. N,N-di([1,1'-biphenyl]-4-yl)-4'-(9H-carbazol-9-yl)-[1,1'-biphenyl]-4-amine was then introduced into another cell of the vacuum vapor depositing apparatus, and an electric current was applied to the cell to evaporate the introduced material, thereby forming a hole transport layer 2 having a thickness of 5 nm on hole transport layer 1. Thereafter, BH-1 as a host compound was introduced into one cell of the vacuum vapor depositing apparatus and BD-1 as a dopant was introduced into another cell. The two materials were evaporated at a different rate and the dopant was deposited in a doping amount of 2 wt %, based on the total weight of the host and dopant, to form a light-emitting layer having a thickness of 20 nm on the hole transport layer. Next, compound ETL-132 was evaporated on one cell to form an electron transport layer having a thickness of 35 nm on the light-emitting layer. After depositing lithium quinolate having a thickness of 4 nm as an electron injection layer on the electron transport layer, an Al cathode having a thickness of 80 nm was then deposited by another vacuum vapor deposition apparatus on the electron injection layer. Thus, an OLED device was produced. All the materials used for producing the OLED device were purified by vacuum sublimation at 10$^{-6}$ torr prior to use.

[BH-1]

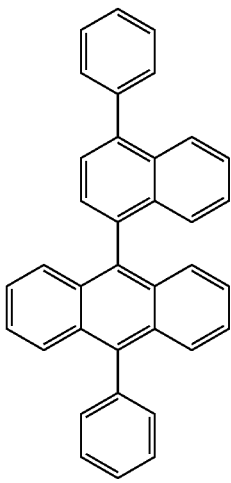

[BD-1]

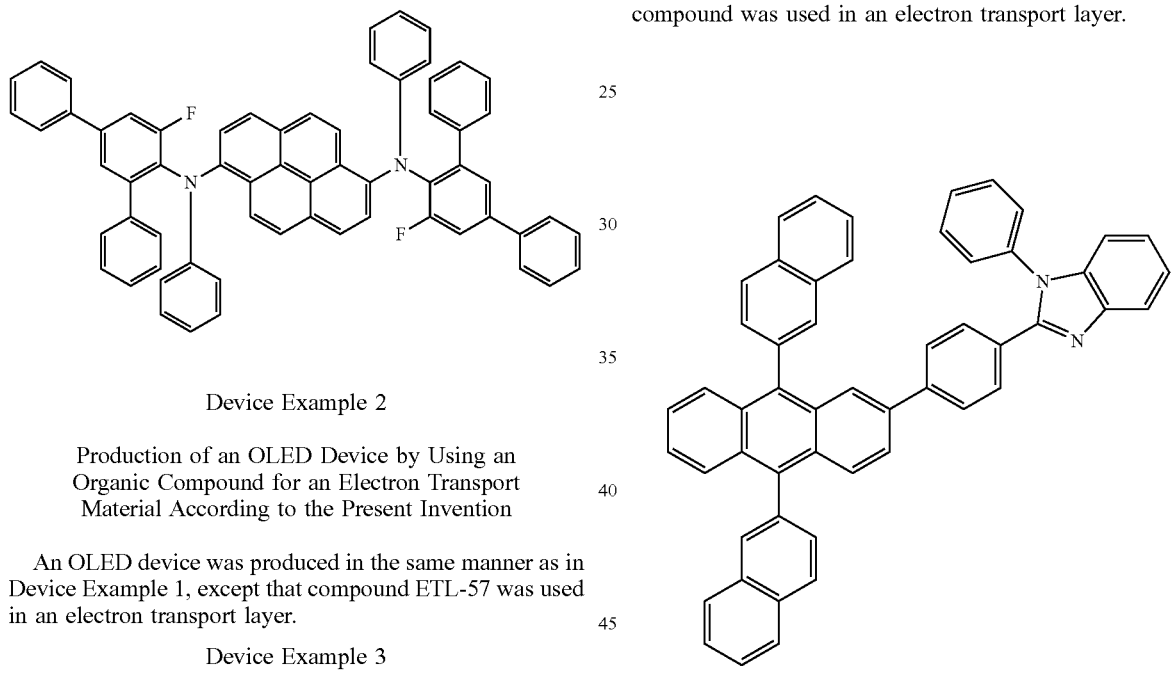

Device Example 2

Production of an OLED Device by Using an Organic Compound for an Electron Transport Material According to the Present Invention An OLED device was produced in the same manner as in Device Example 1, except that compound ETL-57 was used in an electron transport layer.

Device Example 3

Production of an OLED Device by Using an Organic Compound for an Electron Transport Material According to the Present Invention An OLED device was produced in the same manner as in Device Example 1, except that compound ETL-50 was used in an electron transport layer.

Device Example 4

Production of an OLED Device by Using an Organic Compound for an Electron Transport Material According to the Present Invention An OLED device was produced in the same manner as in Device Example 1, except that compound ETL-137 was used in an electron transport layer.

Comparative Example 1

Production of an OLED Device by Using a Conventional Organic Compound for an Electron Transport Material An OLED device was produced in the same manner as in Device Example 1, except that the following comparative compound was used in an electron transport layer.

Figure 2:
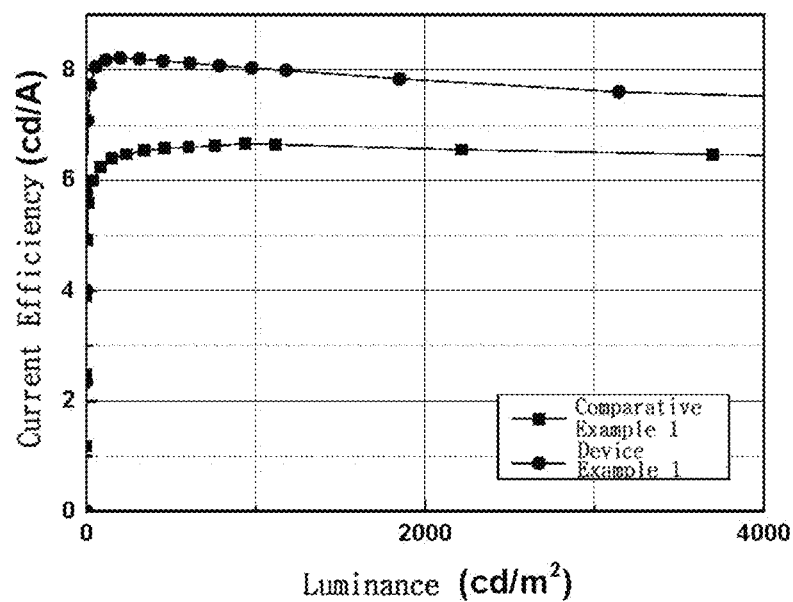
FIG. 2 shows graphs of current efficiency (cd/A) vs. luminance (cd/m$^2$) of the organic EL devices which are respectively produced according to Device Example 1 and Comparative Example 1.

The current efficiency vs. luminance values of the OLED devices produced above are shown in a graph in FIG. 2. Furthermore, driving voltage at a luminance of 1,000 nit, luminous efficiency, and CIE color coordinate of the OLED devices produced in Device Examples 1 to 4 and Comparative Example 1 are provided in Table 1 below.

TABLE 1

|  | Electron Transport Layer | Voltage (V) | Efficiency (cd/A) | Color Coordinate (x) | Color Coordinate (y) | LUMO (eV) | HOMO (eV) |
|---|---|---|---|---|---|---|---|
| Comparative Examples 1 | Comparative Compound | 4.9 | 5.3 | 0.141 | 0.136 | 1.81 | 5.12 |
| Device Example 1 | ETL-132 | 4.0 | 7.9 | 0.138 | 0.105 | 1.92 | 5.41 |
| Device Example 2 | ETL-57 | 4.1 | 7.8 | 0.138 | 0.102 | 1.94 | 5.37 |

TABLE 1-continued

|  | Electron Transport Layer | Voltage (V) | Efficiency (cd/A) | Color Coordinate (x) | Color Coordinate (y) | LUMO (eV) | HOMO (eV) |
|---|---|---|---|---|---|---|---|
| Device Example 3 | ETL-50 | 4.2 | 7.8 | 0.138 | 0.102 | 1.84 | 5.51 |
| Device Example 4 | ETL-137 | 4.5 | 7.4 | 0.138 | 0.102 | 1.88 | 5.52 |

The above data were determined under the condition that electron affinity of an electron transport layer (Ab) is higher than electron affinity of a host (Ah, LUMO=1.6 eV), and electron transport layers of Device Examples according to the present invention have higher electron affinity than that of Comparative Example 1. LUMO (lowest unoccupied molecular orbital) energy value and HOMO (highest occupied molecular orbital) energy value have inherently negative number, but LUMO energy value (A) and HOMO energy value in the present invention are conveniently expressed in their absolute values. Furthermore, the comparison between LUMO energy values is based on their absolute values. LUMO energy value and HOMO energy value in the present invention are calculated by Density Functional Theory.

Figure 3:
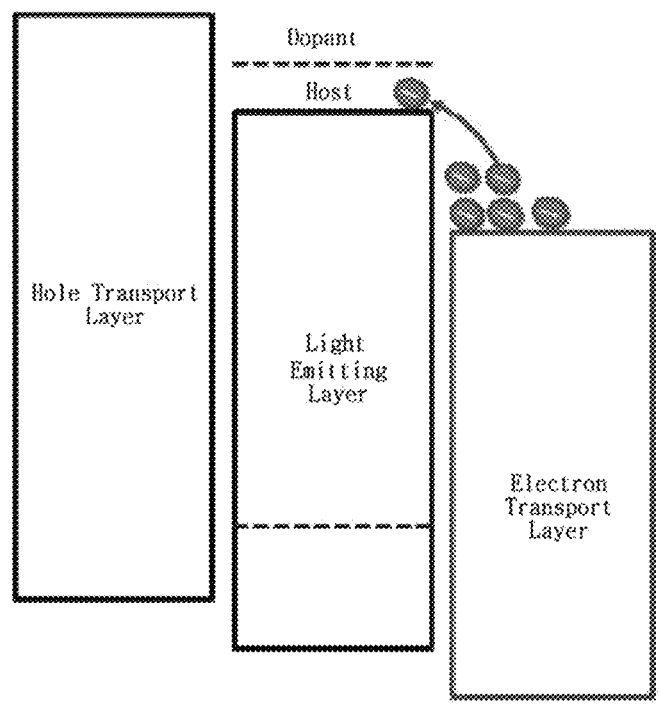
FIG. 3 shows energy diagram of the organic EL device comprising the electron transport layer according to the present invention.

As depicted in FIG. 3, the devices according to the present invention have a big barrier between a light-emitting layer and an electron transport layer in the process of transporting electrons compared with the device of Comparative Example 1 (see LUMO energy value). However, the devices of the present invention have fast electron current property, and thus have lower driving voltage and higher efficiency than the device of Comparative Example 1. Furthermore, the compound of the present invention has higher HOMO energy value than the comparative compound of Comparative Example 1, and thus restricts efficiently movement of excitons produced in a light-emitting layer and hole carriers as shown in FIG. 3. According to this, the compound of the present invention is regarded as showing color coordinate having the nearest to pure blue compared with the comparative compound of Comparative Example 1.

Comparison of Electron Current Property of the Comparative Compound of Comparative Example 1 and the Compound of Present Invention In order to demonstrate fast electron current property of an electron transport layer in the devices according to the present invention, voltage property was compared by preparing an Electron Only Device (EOD).

The device was produced as follows: Barium, 2,9-dimethyl-4,7-diphenyl-1,10-phenanthroline (BCP) were introduced into cells in a vacuum vapor depositing apparatus. Thereafter, an electric current was applied to the cells to evaporate the introduced materials, thereby forming a hole blocking layer (HBL) having a thickness of 10 nm on the ITO substrate. Thereafter, BH-1 as a host compound was introduced into one cell of the vacuum vapor depositing apparatus and BD-1 as a dopant was introduced into another cell. The two materials were evaporated at a different rate and the dopant was deposited in a doping amount of 2 wt %, based on the total weight of the host and dopant, to form a light-emitting layer having a thickness of 20 nm on a hole transport layer. Next, the compounds in the table below were evaporated to form an electron transport layer having a thickness of 33 nm on the light-emitting layer. After depositing lithium quinolate having a thickness of 4 nm as an electron injection layer on the electron transport layer, an Al cathode having a thickness of 80 nm was then deposited by another vacuum vapor deposition apparatus on the electron injection layer. Thus, an OLED device was produced. All the materials used for producing the OLED device were purified by vacuum sublimation at $10^{-6}$ torr prior to use. Voltages at 10 and 50 mA/cm$^2$ according to each material of an electron transport layer are provided in Table 2 below.

TABLE 2

| Electron Transport Layer | Voltage(V) (10 mA/cm$^2$) | Voltage(V) (50 mA/cm$^2$) |
|---|---|---|
| Comparative Compound | 4.4 | 5.0 |
| ETL-132 | 3.2 | 4.3 |
| ETL-57 | 3.4 | 4.1 |
| ETL-50 | 3.5 | 4.8 |
| ETL-137 | 3.7 | 4.9 |

As shown in Table 2 above, the compounds of the present invention have faster electron current property at both voltages (10 and 50 mA/cm$^2$) than the comparative compound of Comparative Example 1. The EOD identified that the compounds of the present invention were suitable to provide low driving voltage and high efficiency.

The invention claimed is:

1. An electron transport material comprising a compound represented by the following formula 1:

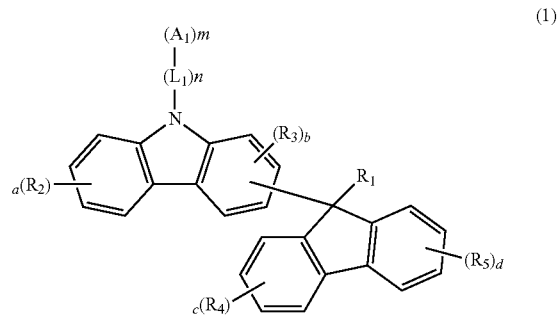

(1)

wherein $A_1$ represents a substituted or unsubstituted pyridyl, a substituted or unsubstituted pyrimidyl, a substituted or unsubstituted triazinyl, a substituted or unsubstituted pyrazinyl, a substituted or unsubstituted quinolinyl, a substituted or unsubstituted quinazolinyl, a substituted or unsubstituted quinoxalinyl, a substituted or unsubstituted naphthyridinyl, or a substituted or unsubstituted phenanthrolinyl;

$L_1$ represents a single bond, or phenylene, biphenylene or naphthylene unsubstituted or substituted with deuterium;

R₁ represents a substituted or unsubstituted (C1-C30) alkyl group, or phenylene, biphenylene or naphthylene unsubstituted or substituted with deuterium;

R₂ represents hydrogen, deuterium, or a structure of formula 2:

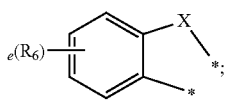
(2)

or

R₂, fused to the carbazole structure, forms a benzocarbazole ring;

R₃ represents hydrogen, deuterium, a halogen, a substituted or unsubstituted (C6-C30)aryl group, or a substituted or unsubstituted 5- to 30-membered heteroaryl group;

X represents O, S, NR₁₁, or SiR₁₂R₁₃;

R₄, R₅, and R₆ each independently represent hydrogen, deuterium, a substituted or unsubstituted (C6-C30)aryl group, or a substituted or unsubstituted 5- to 30-membered heteroaryl group;

R₁₁ to R₁₃ each independently represent a substituted or unsubstituted (C6-C30)aryl group, or a substituted or unsubstituted 5- to 30-membered heteroaryl group;

a, c, d, and e each independently represent an integer of 1 to 4; where a, c, d, or e is an integer of 2 or more, each R₂, each R₄, each R₅, or each R₆ is the same or different;

b represents an integer of 1 to 3; where b is an integer of 2 or more, each R₃ is the same or different;

n represents an integer of 0 or 1;

m represents an integer of 1 or 2; and the heteroaryl and heteroarylene groups contain at least one hetero atom selected from B, N, O, S, P(=O), Si, and P.

2. The electron transport material according to claim 1, wherein the compound of formula 1 is represented by the following formula 3, 4, or 5:

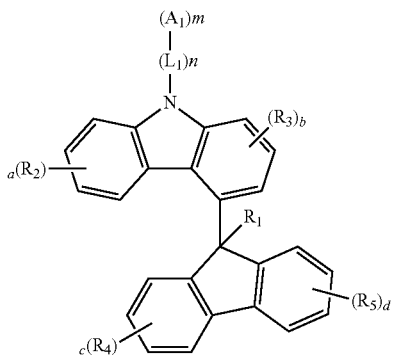
(3)

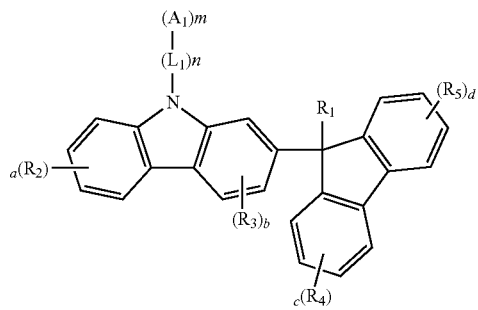
(4)

(5)

wherein

A₁, L₁, R₁, R₂, R₃, R₄, R₅, a, b, c, d, m, and n are as defined in claim 1.

3. An electron transport material selected from the group consisting of the following compounds:

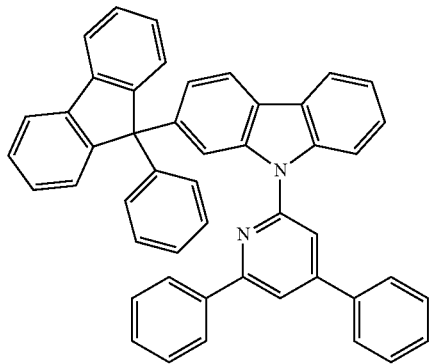
ETL-1

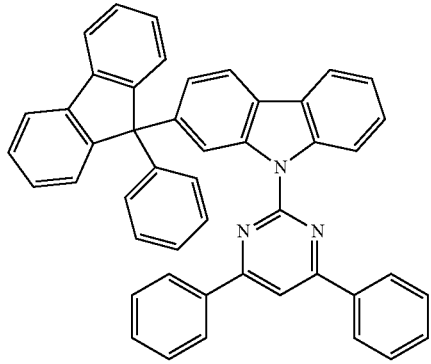
ETL-2

ETL-3
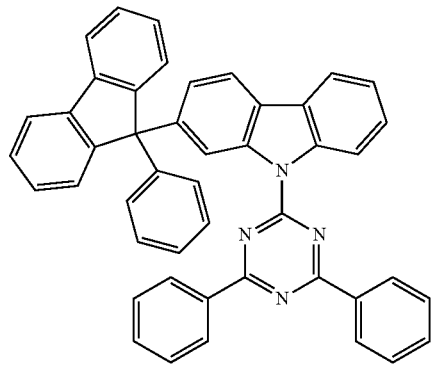
ETL-7
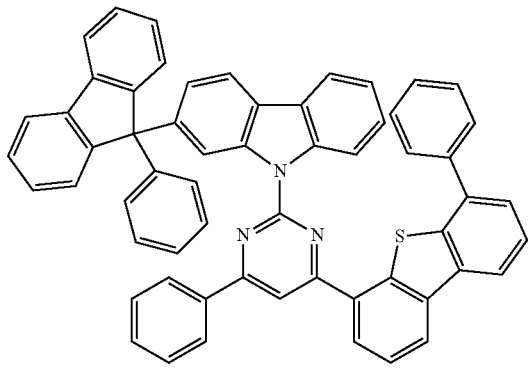
ETL-4
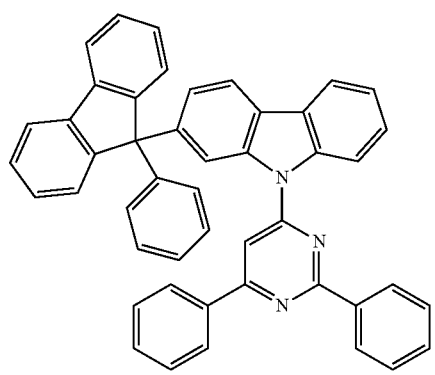
ETL-8
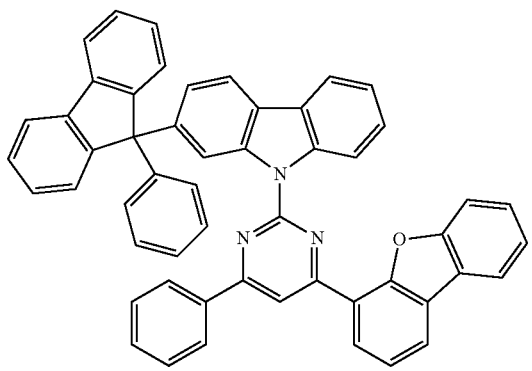
ETL-5
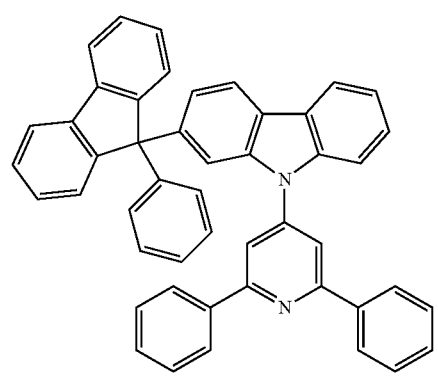
ETL-9
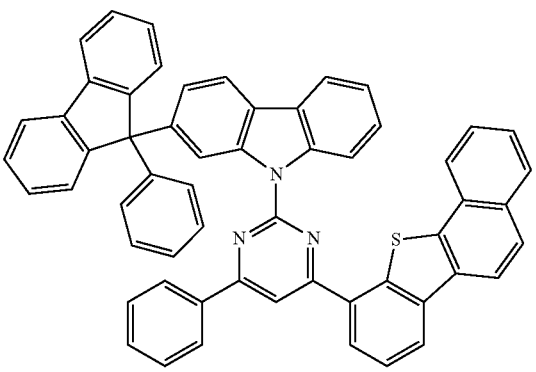
ETL-6
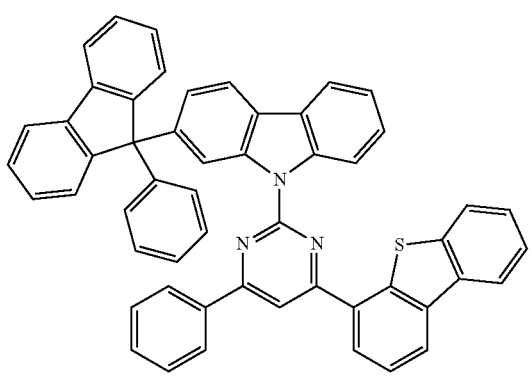
ETL-10
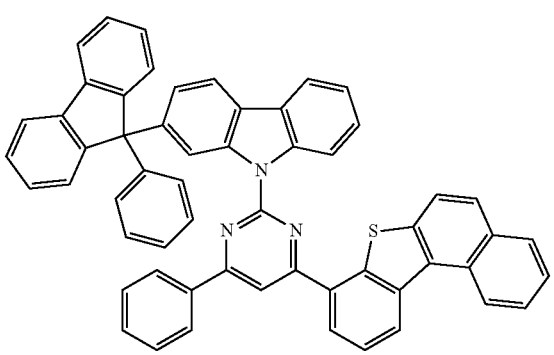

ETL-11
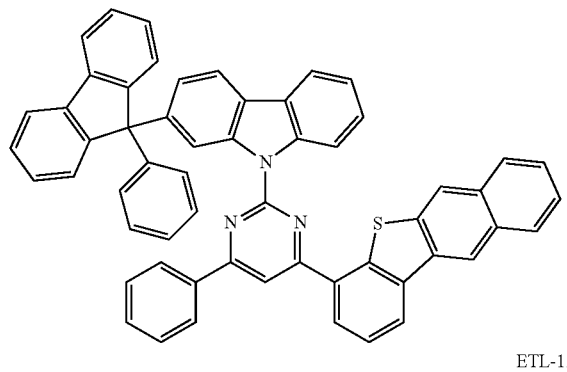
ETL-12
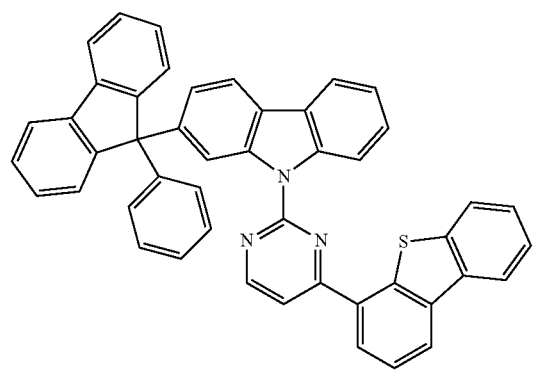
ETL-13
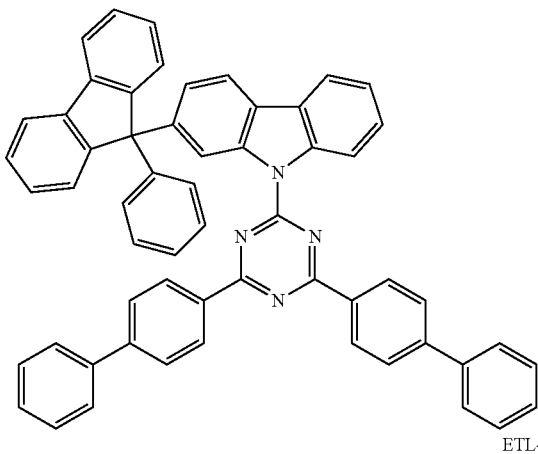
ETL-14
ETL-15
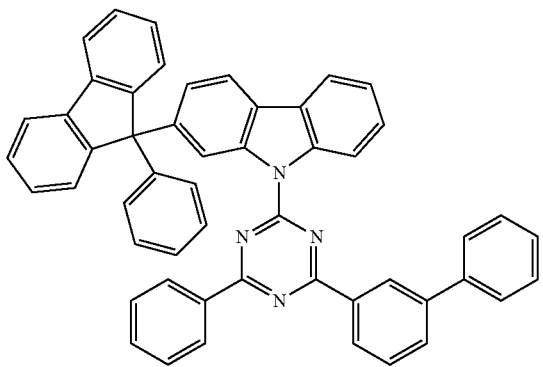
ETL-16
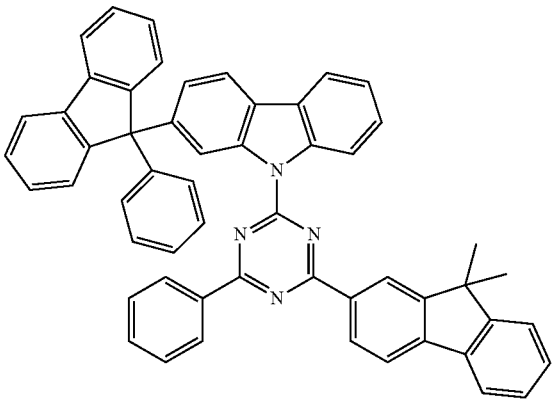
ETL-17
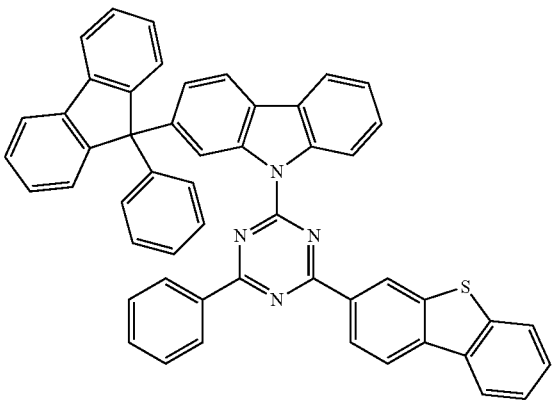
ETL-18
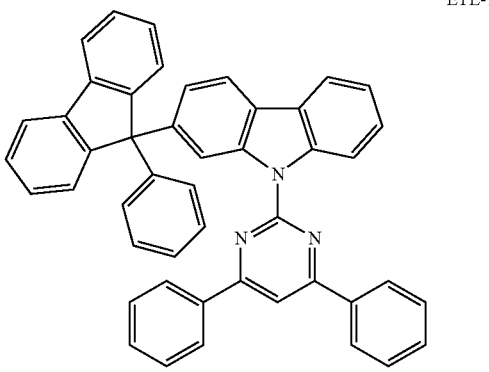

-continued
ETL-19
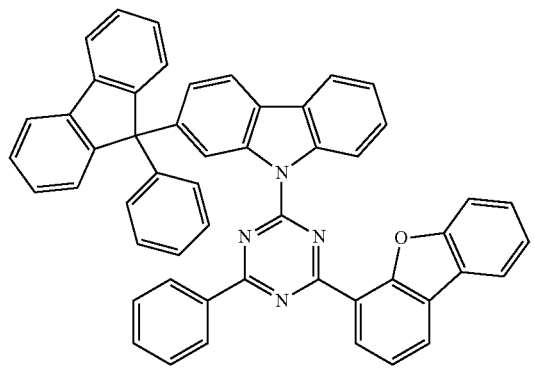
ETL-20
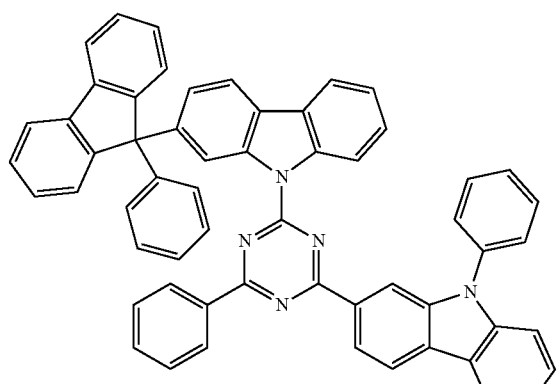
ETL-21
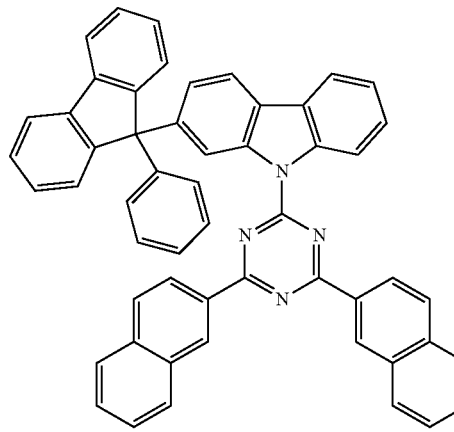
ETL-22
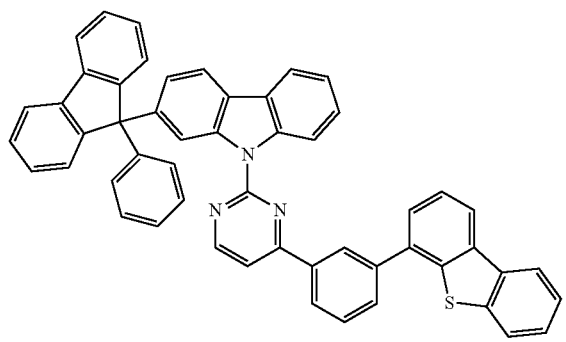
-continued
ETL-23
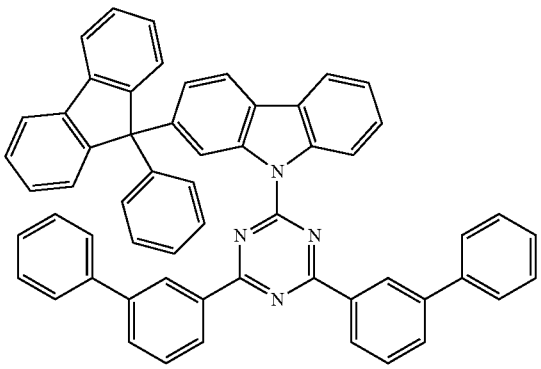
ETL-24
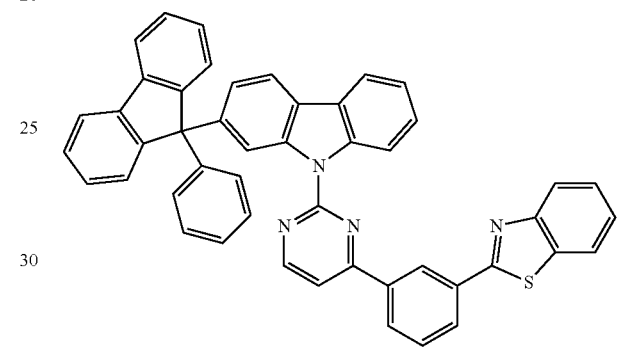
ETL-25
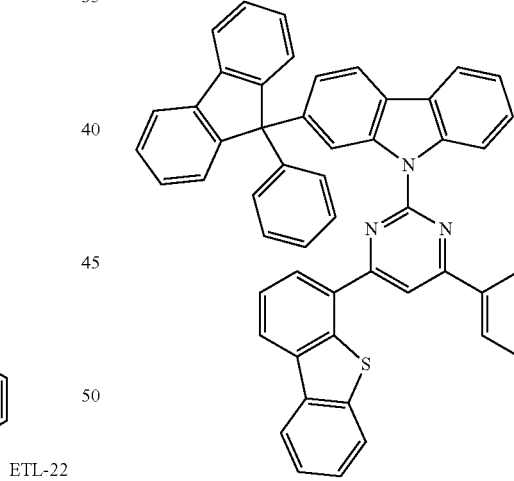
ETL-26
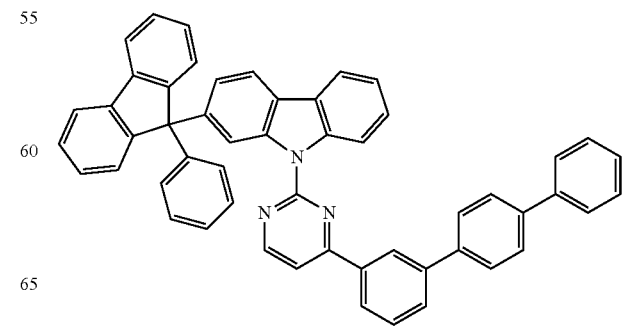

-continued
ETL-27
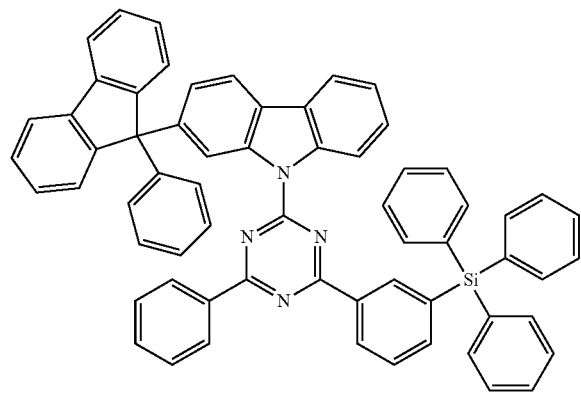
ETL-28
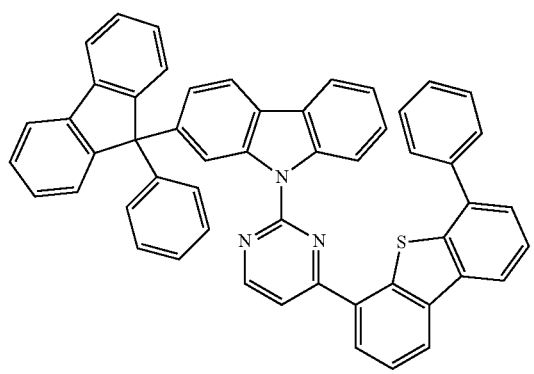
ETL-29
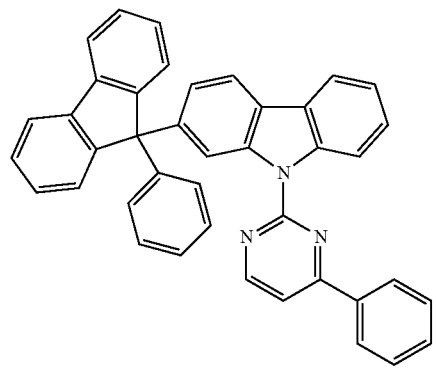
ETL-30
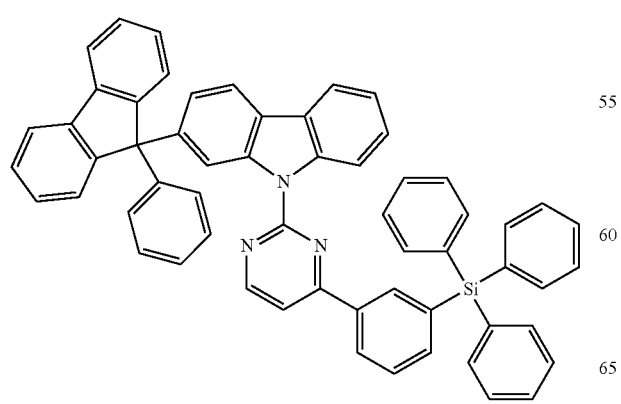
-continued
ETL-31
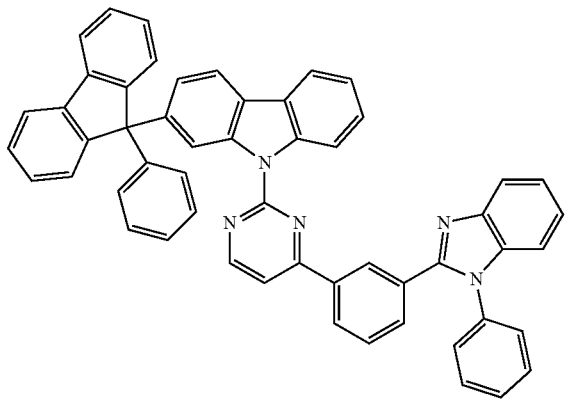
ETL-32
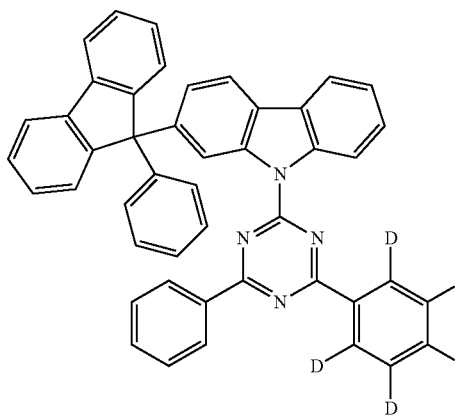
ETL-33
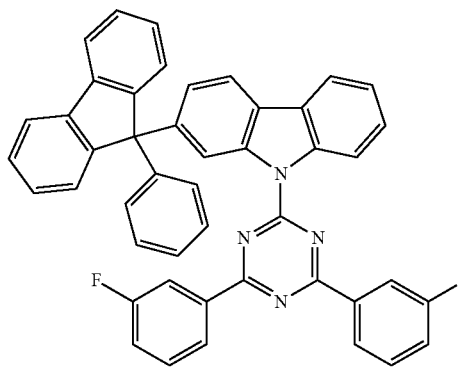

ETL-34
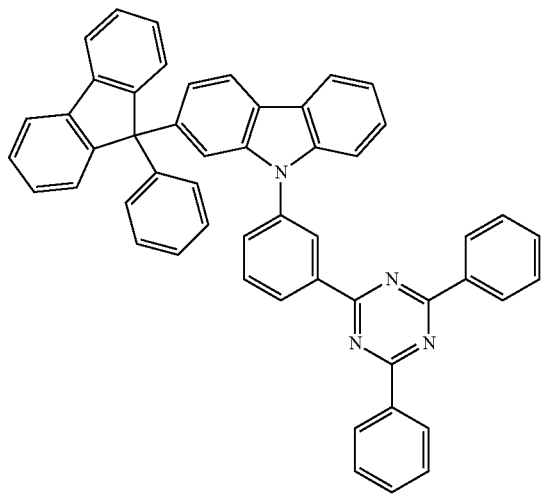
ETL-37
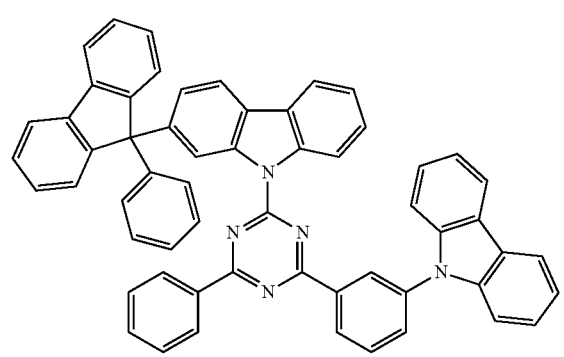
ETL-38
ETL-35
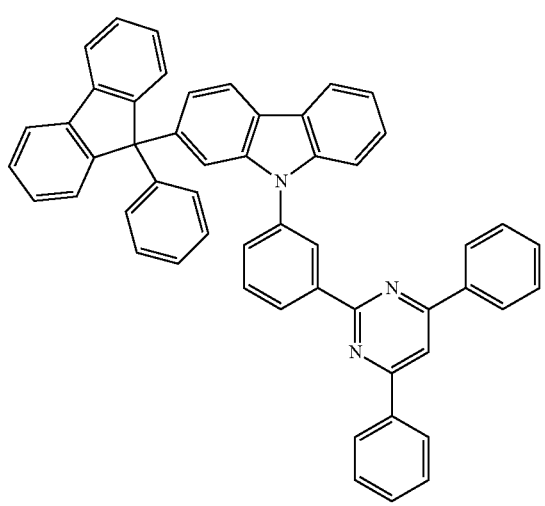
ETL-39
ETL-36
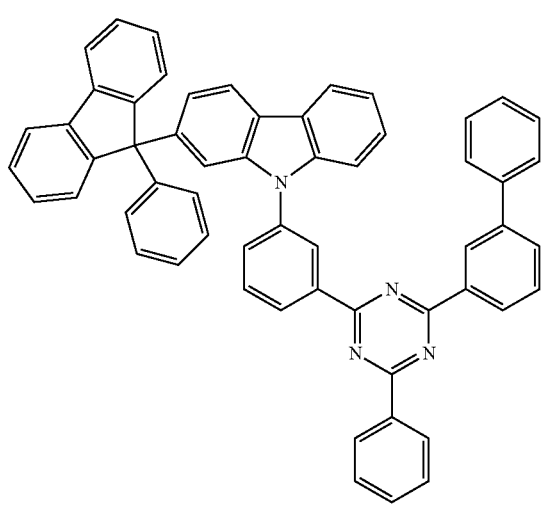
ETL-40
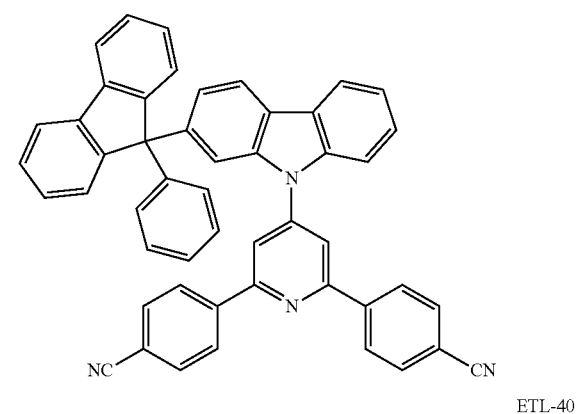

ETL-41
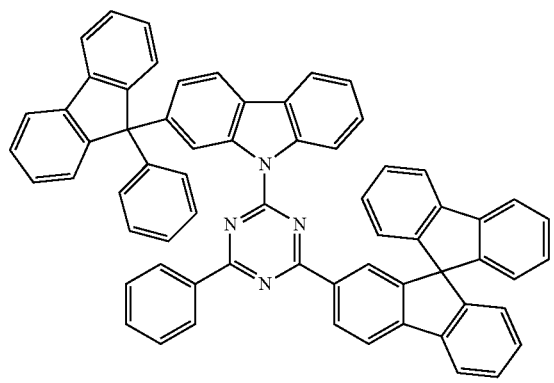
ETL-42
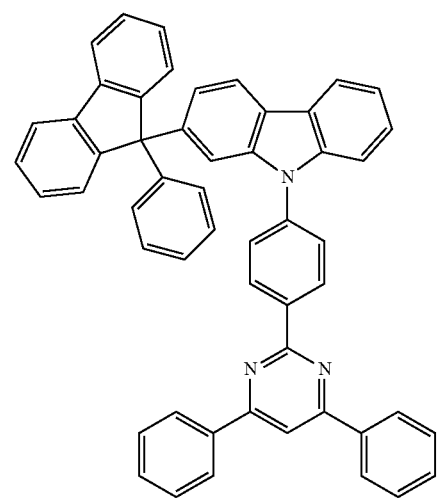
ETL-43
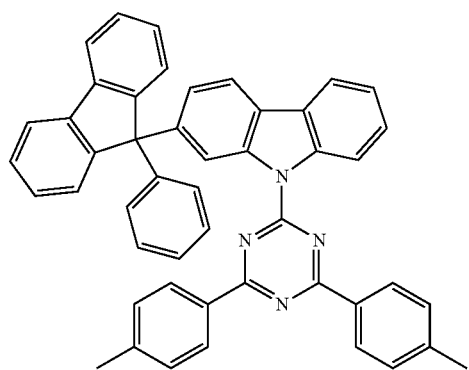
ETL-44
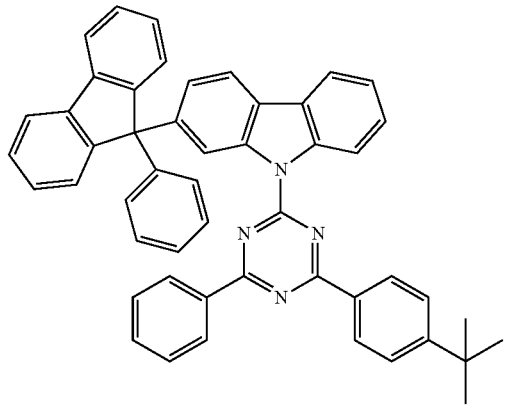
ETL-45
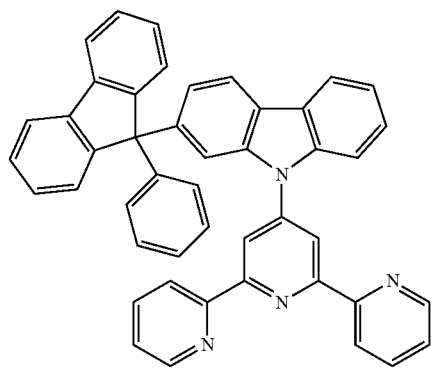
ETL-46
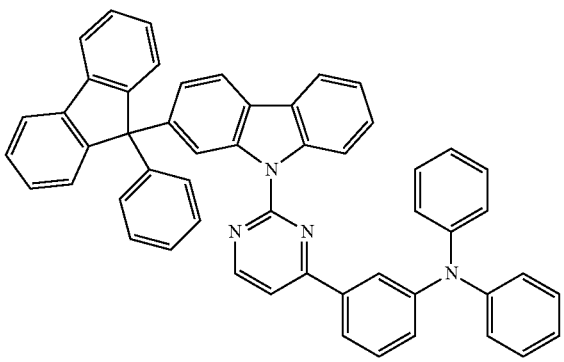
ETL-47
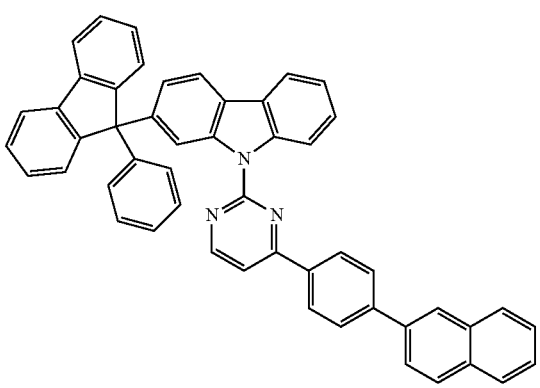

ETL-48
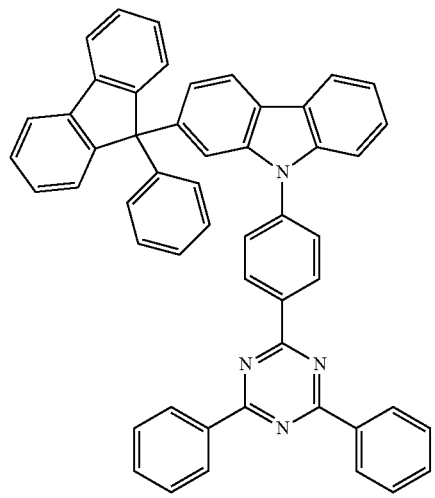
ETL-49
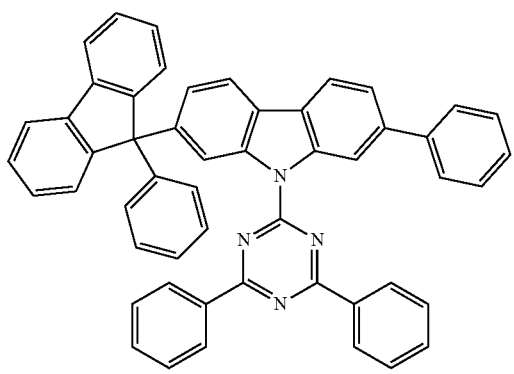
ETL-50
ETL-51
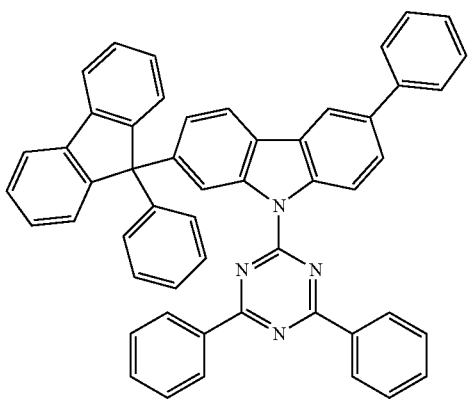
ETL-52
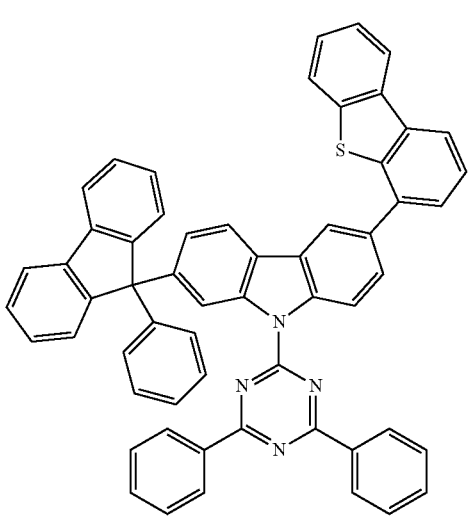
ETL-53
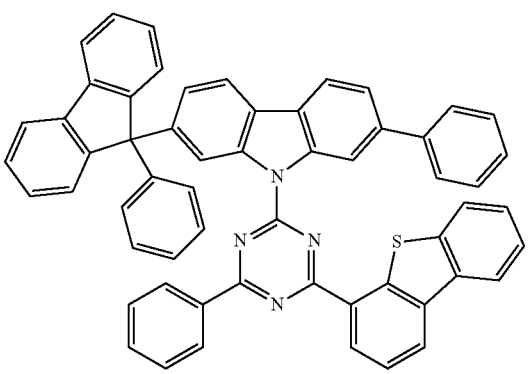

ETL-54
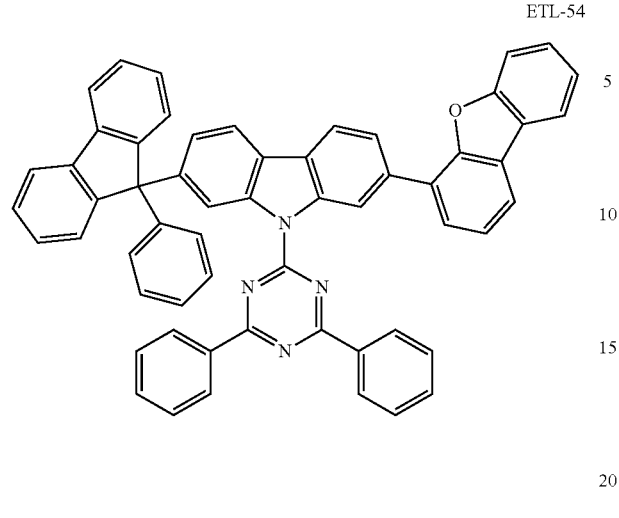
ETL-57
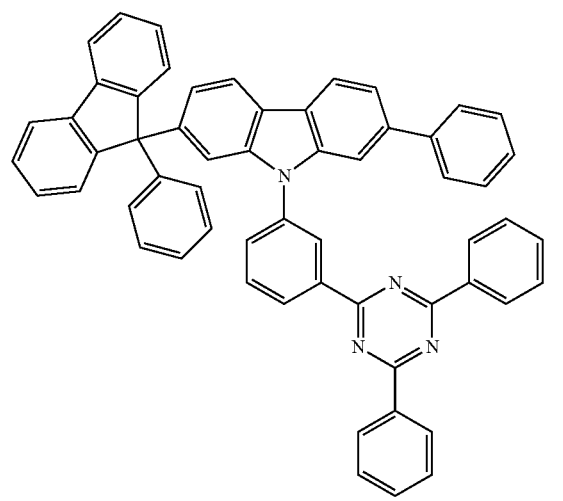
ETL-55
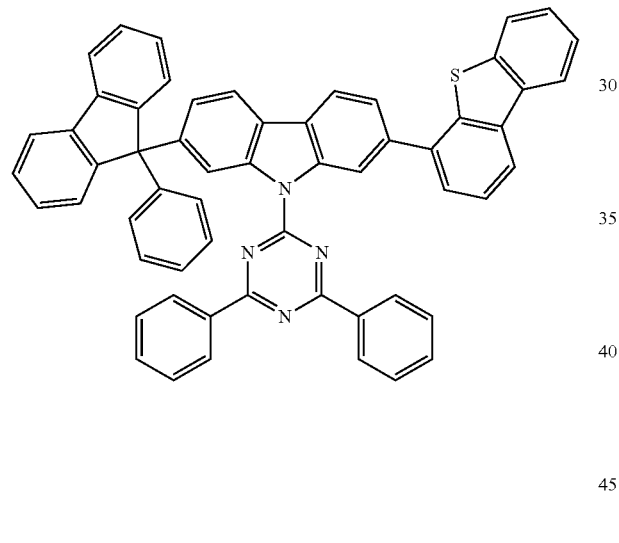
ETL-58
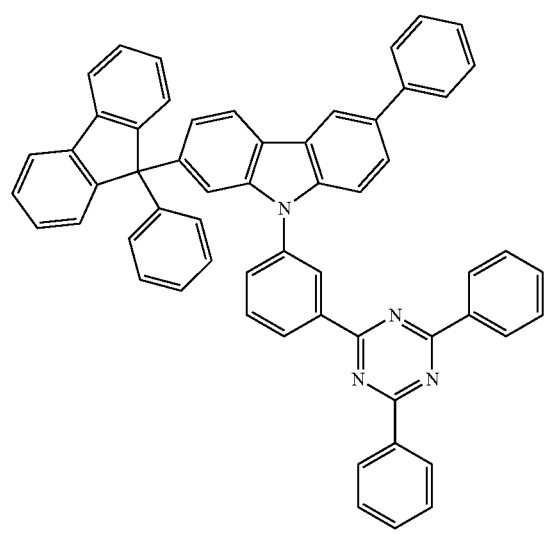
ETL-56
ETL-59
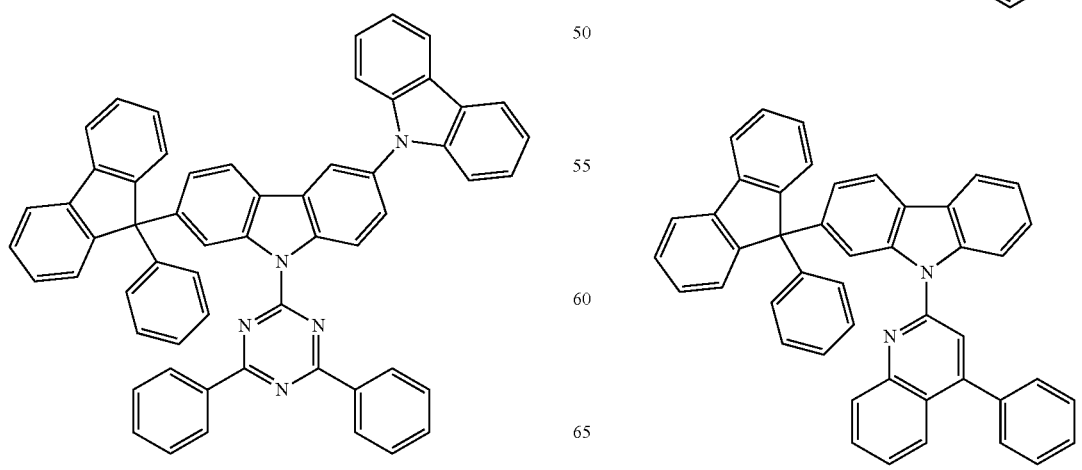

ETL-60
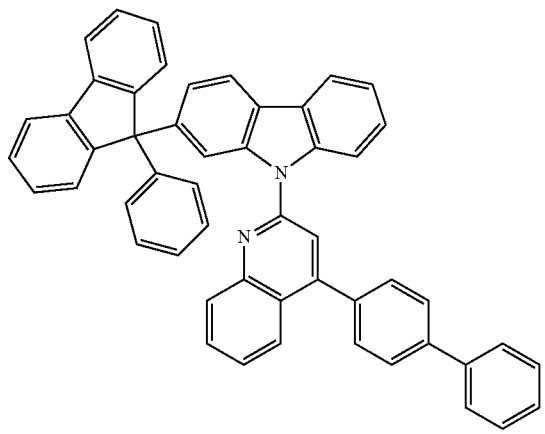
ETL-61
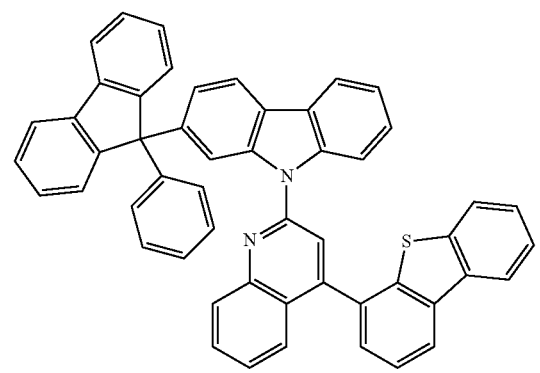
ETL-62
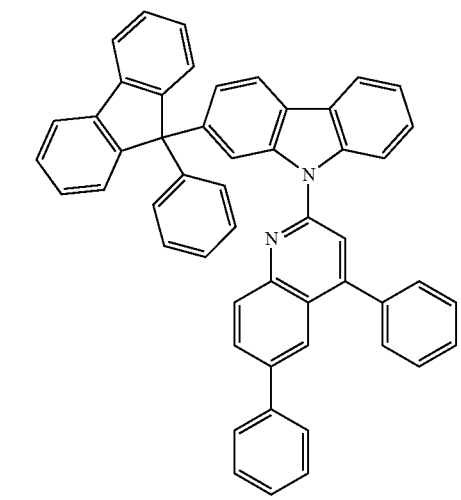
ETL-63
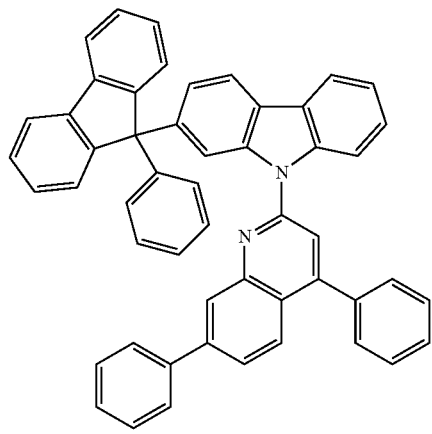
ETL-64
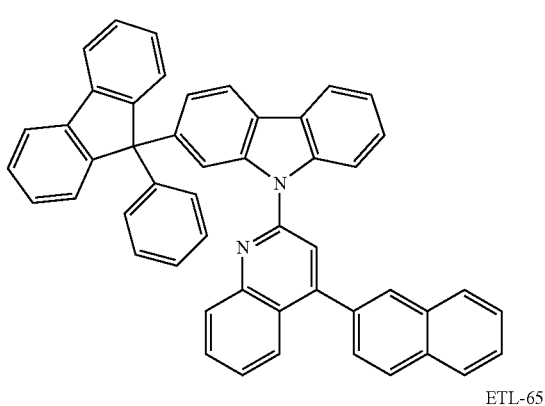
ETL-65
ETL-66
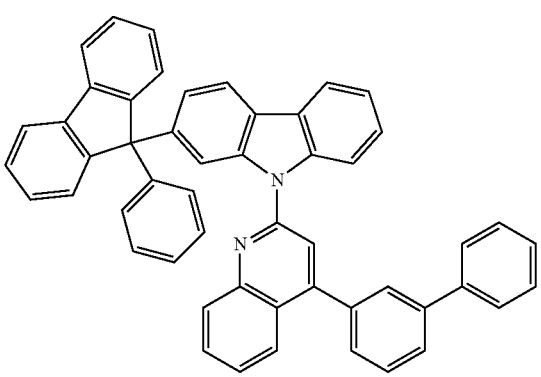

ETL-67
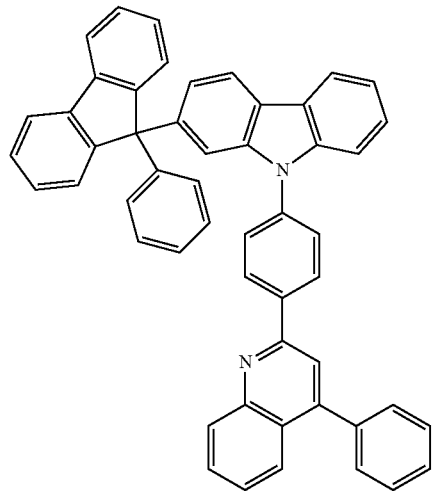
ETL-68
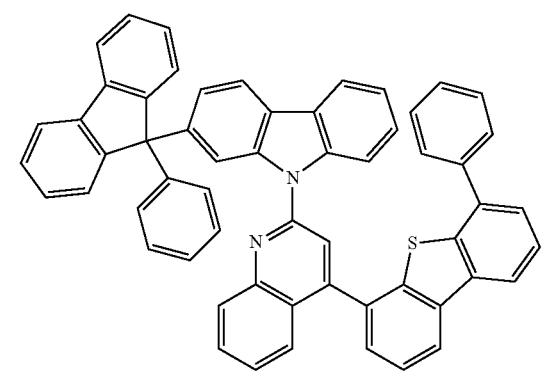
ETL-69
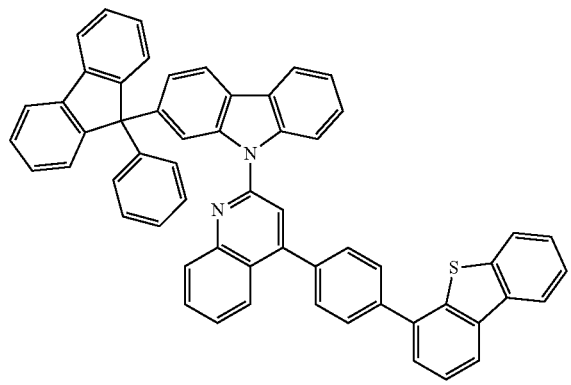
ETL-70
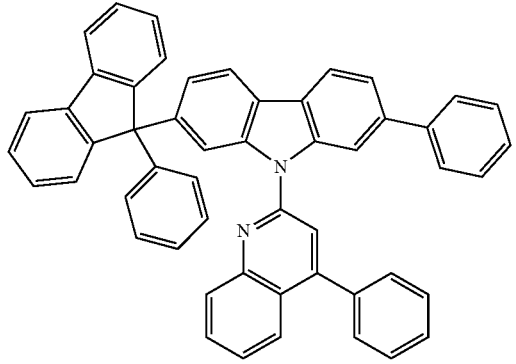
ETL-71
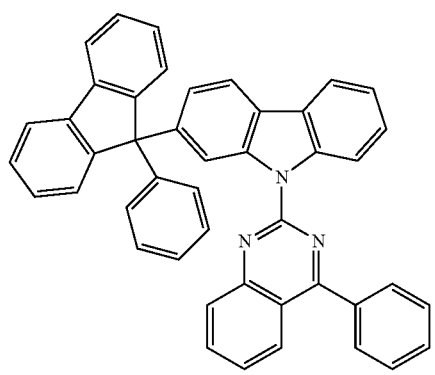
ETL-72
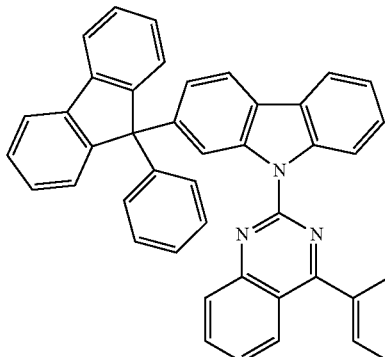
ETL-73
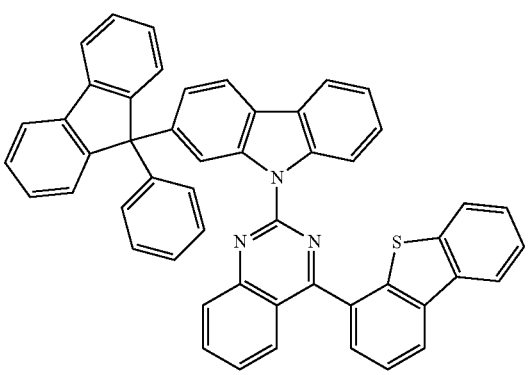

ETL-74
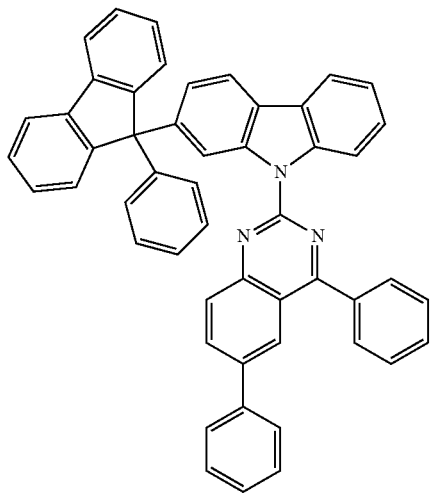
ETL-77
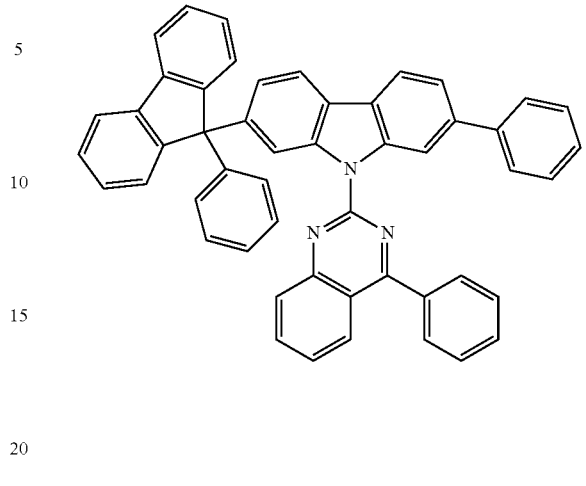
ETL-75
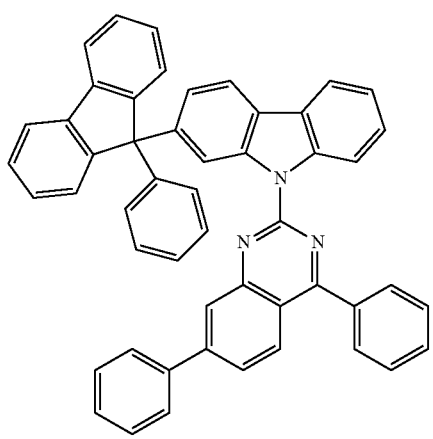
ETL-78
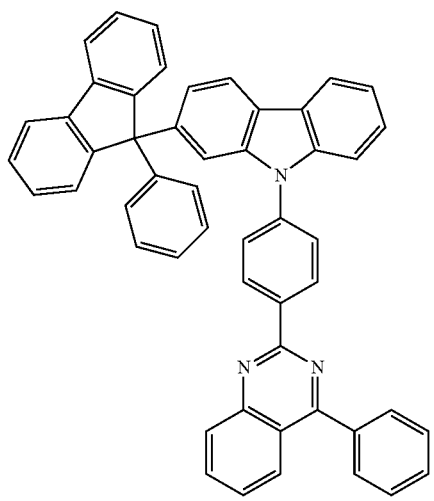
ETL-76
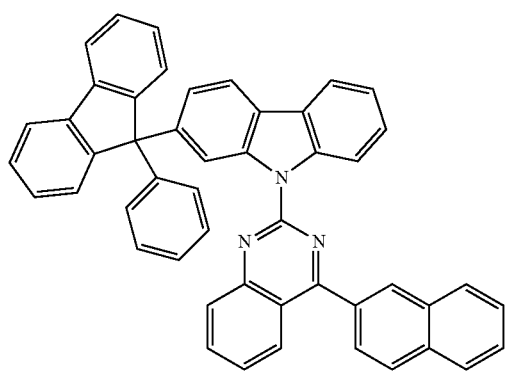
ETL-79
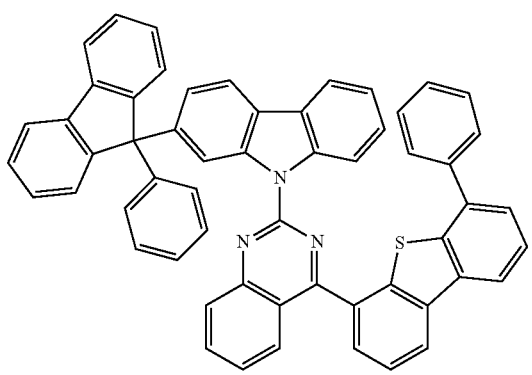

-continued
ETL-80
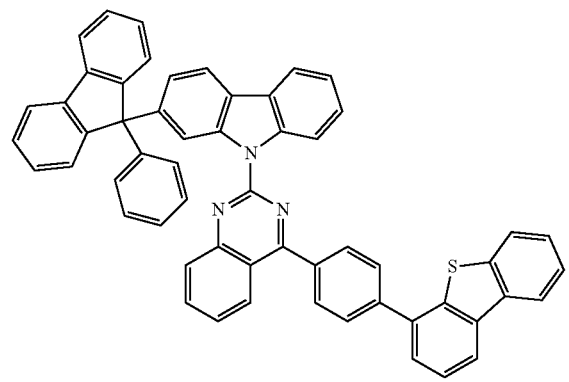
ETL-81
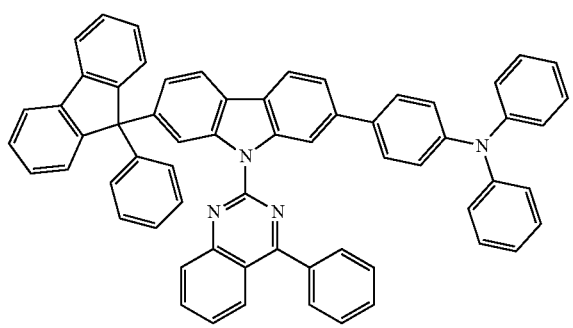
ETL-82
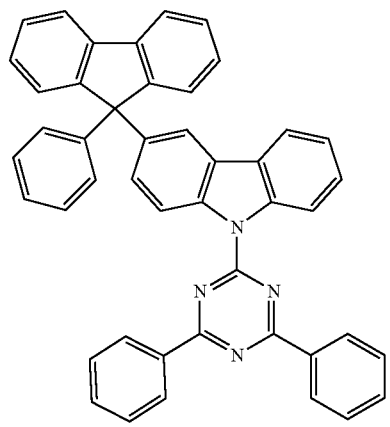
ETL-83
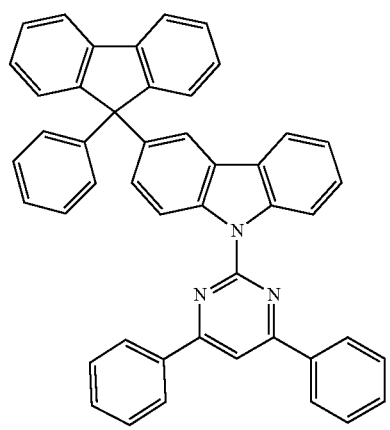
-continued
ETL-84
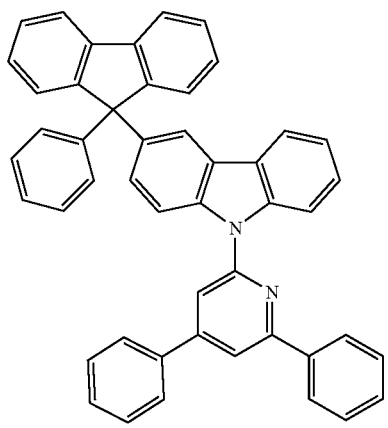
ETL-85
ETL-86

ETL-87
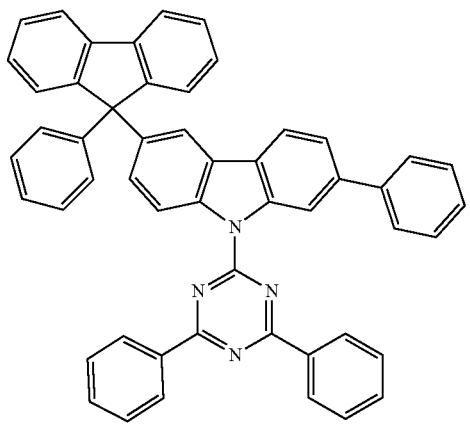
ETL-88
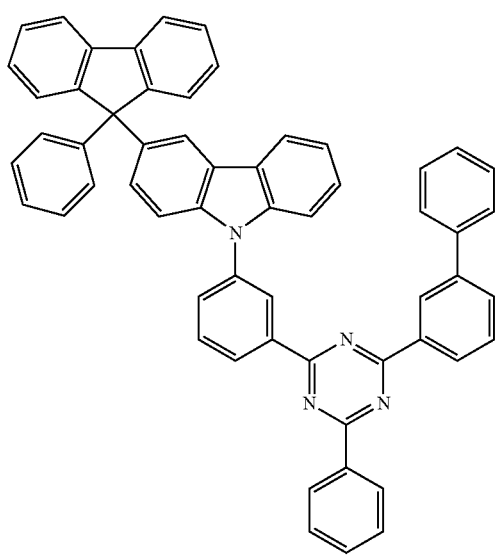
ETL-89
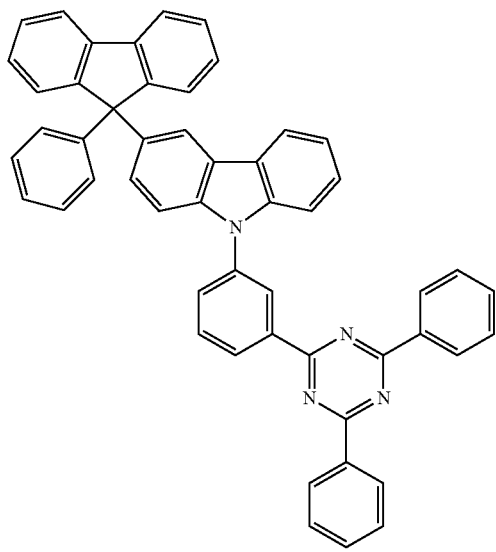
ETL-90
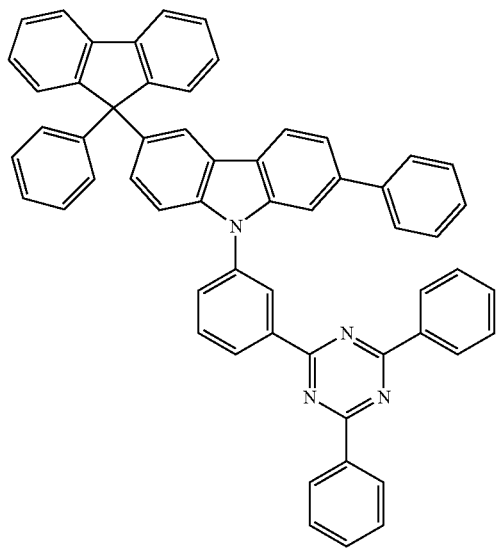
ETL-91
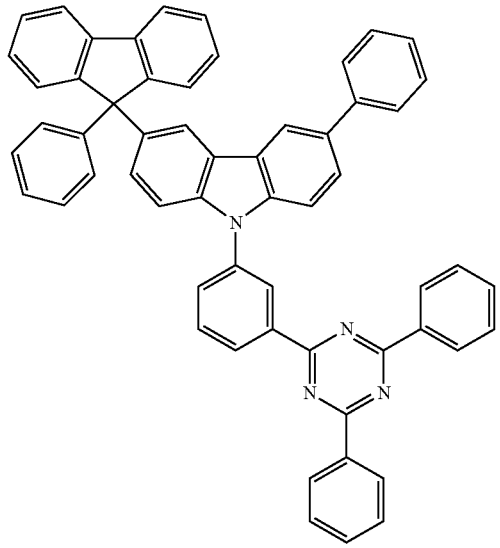
ETL-92
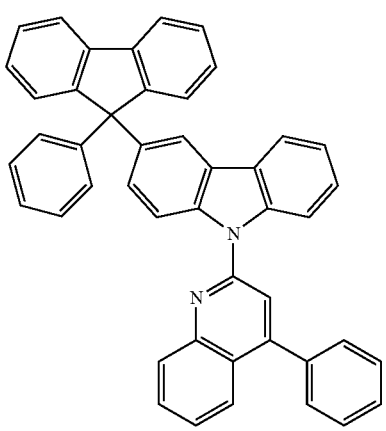

ETL-93
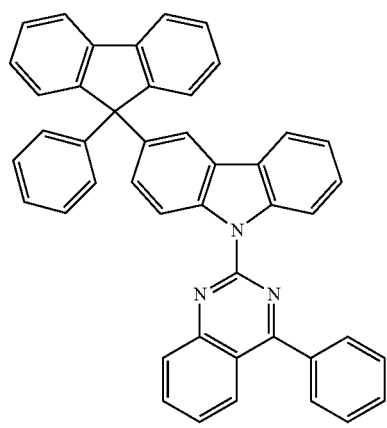
ETL-94
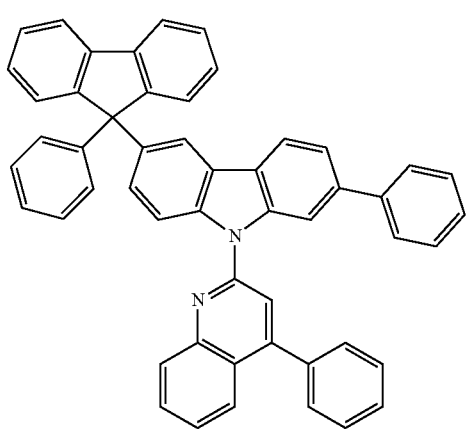
ETL-95
ETL-96
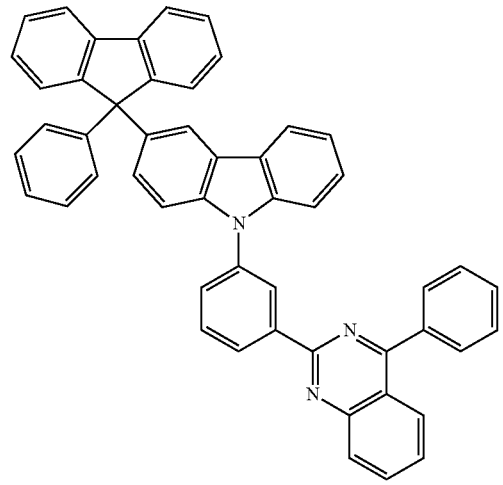
ETL-97
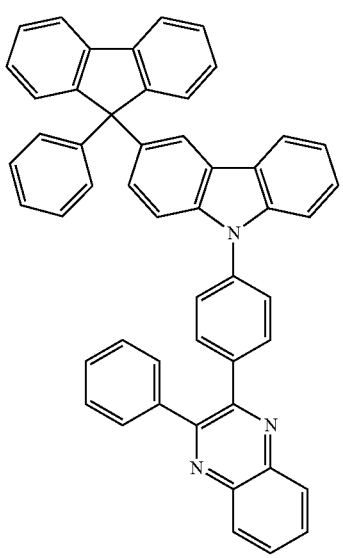
ETL-98
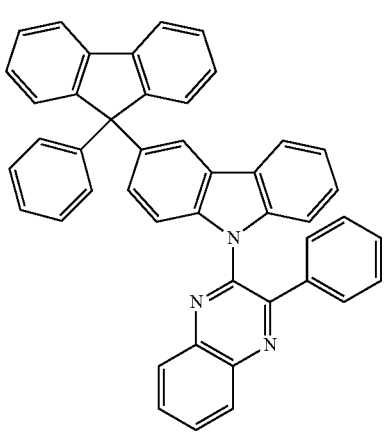

-continued
ETL-99
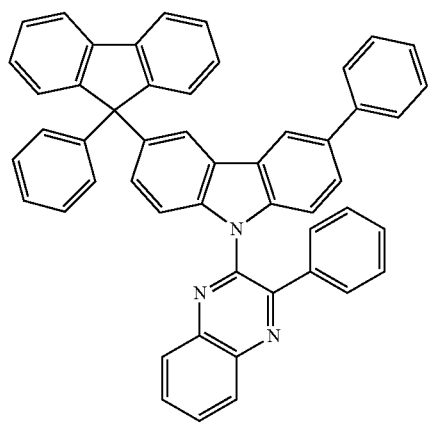
ETL-100
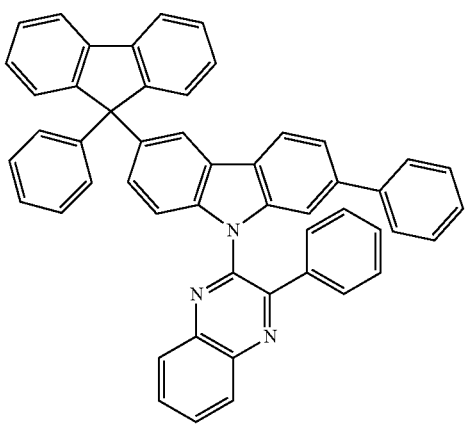
ETL-101
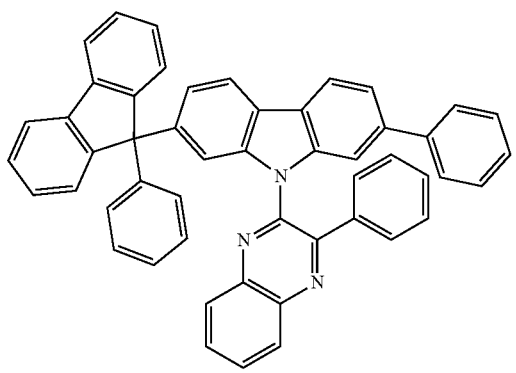
ETL-102
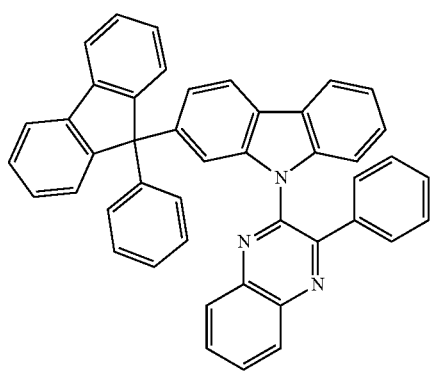
-continued
ETL-103
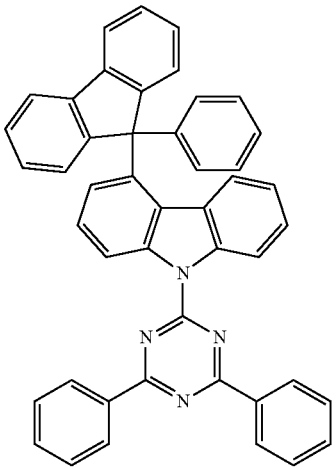
ETL-104
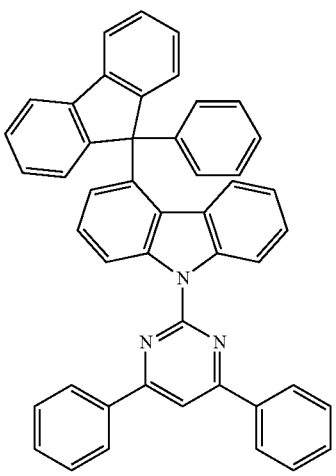
ETL-105
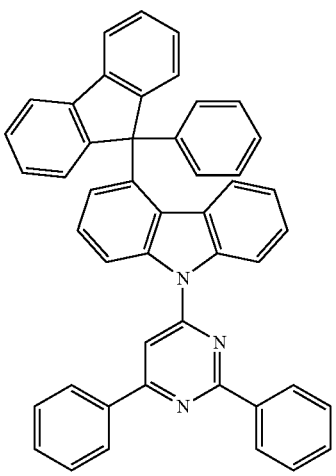

ETL-106
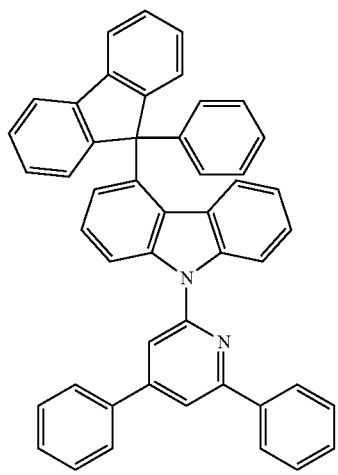
ETL-107
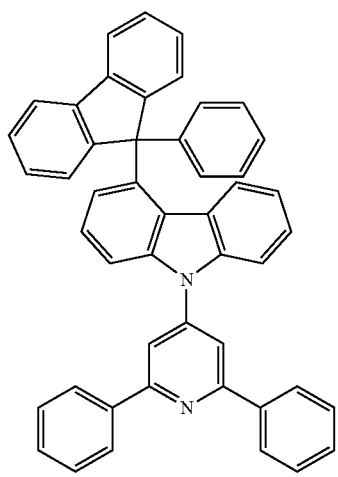
ETL-108
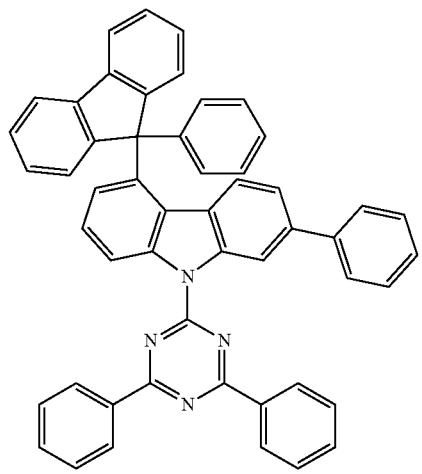
ETL-109
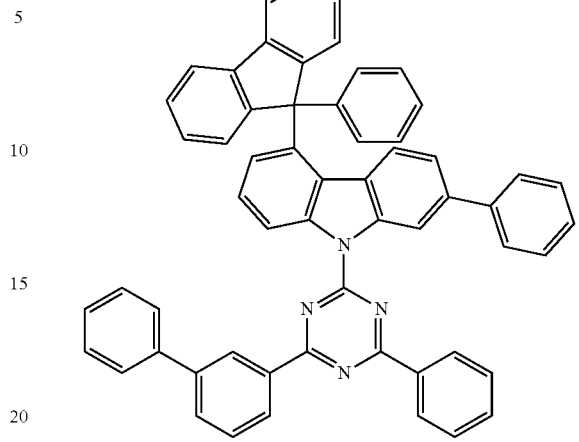
ETL-110
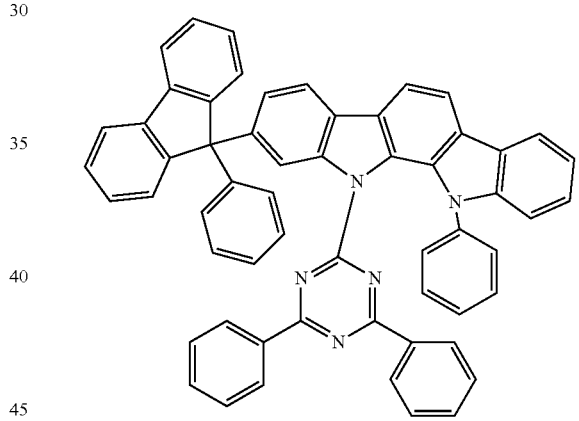
ETL-111
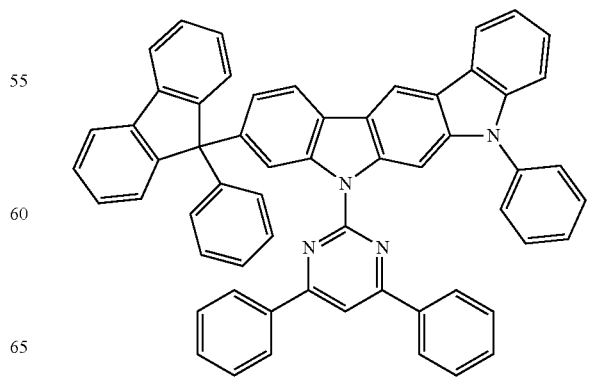

ETL-112
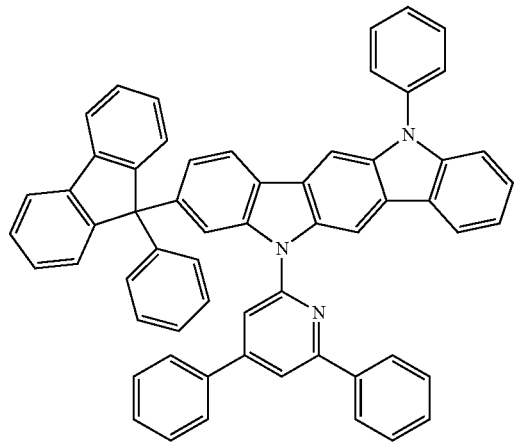
ETL-113
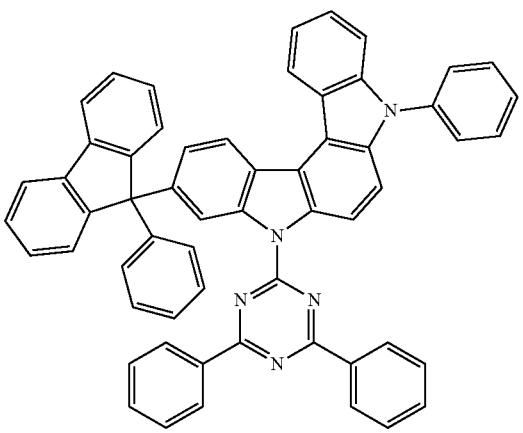
ETL-114
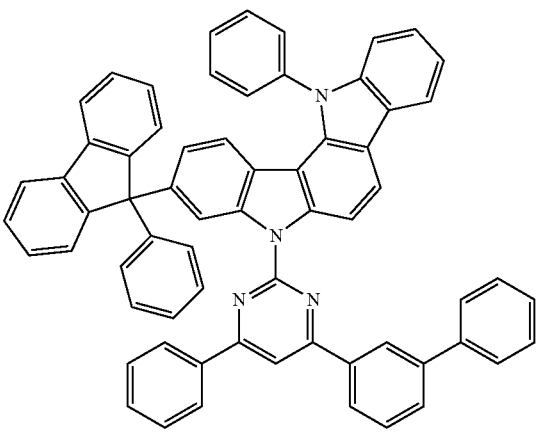
ETL-115
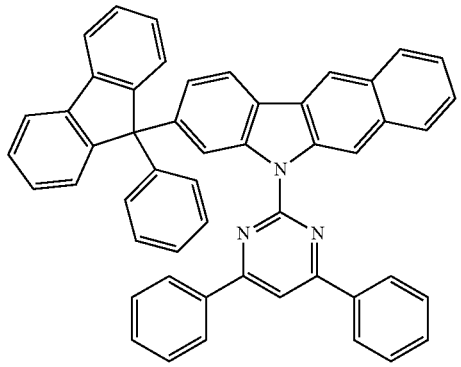
ETL-116
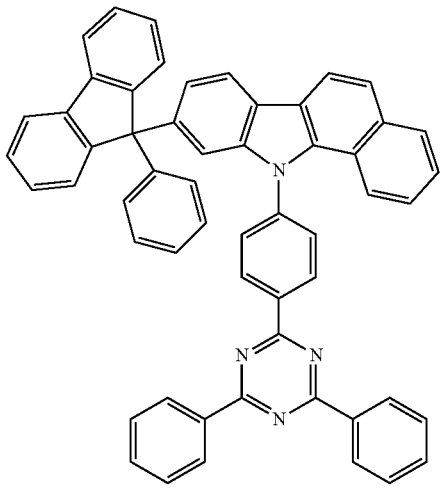
ETL-117
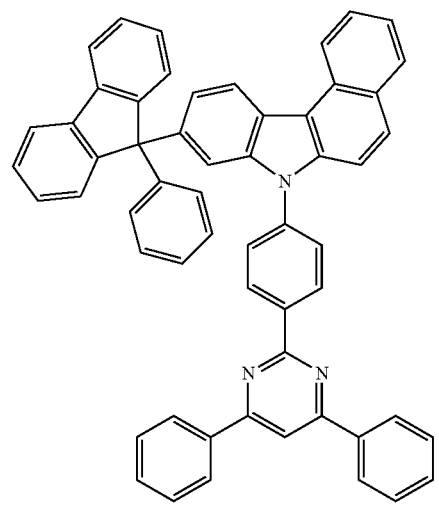

ETL-118
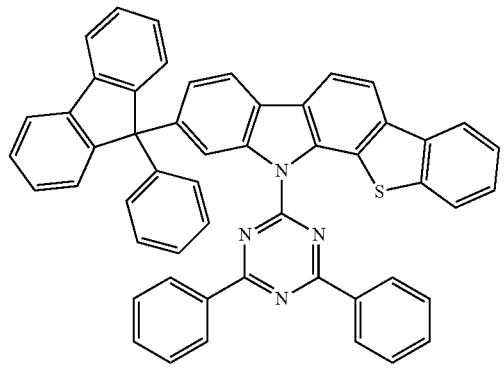
ETL-119
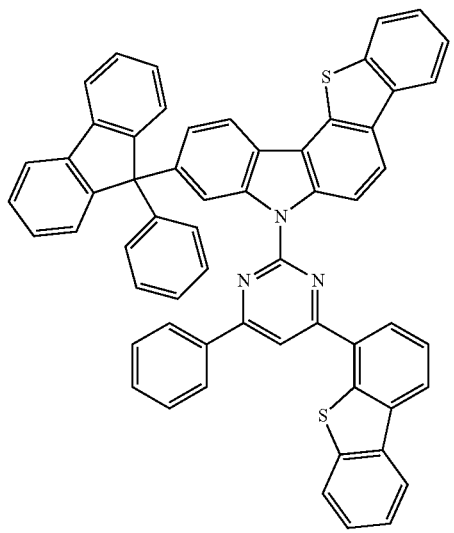
ETL-120
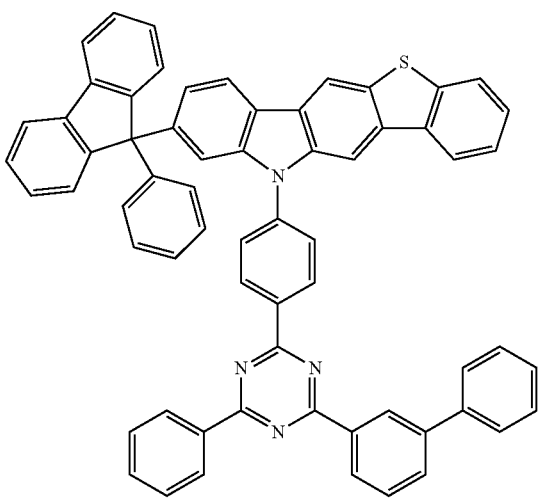
ETL-121
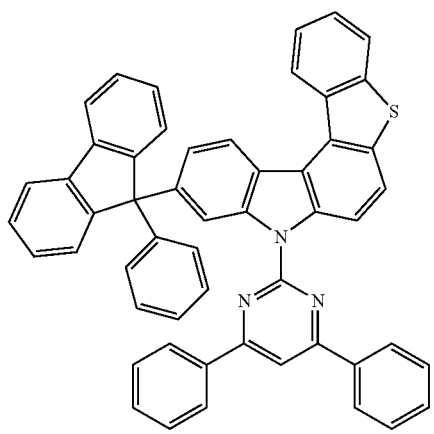
ETL-122
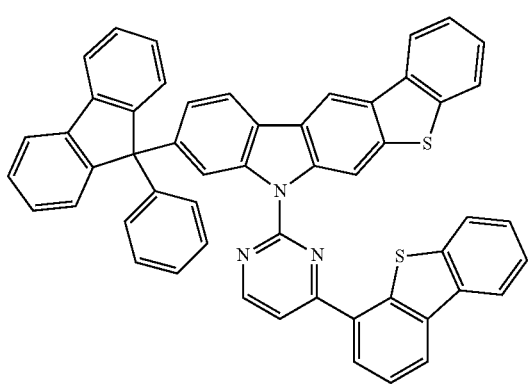
ETL-123
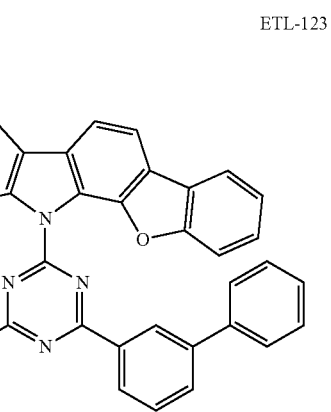

ETL-124
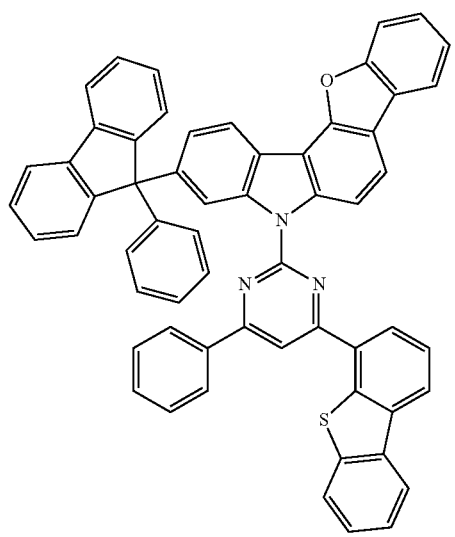
ETL-125
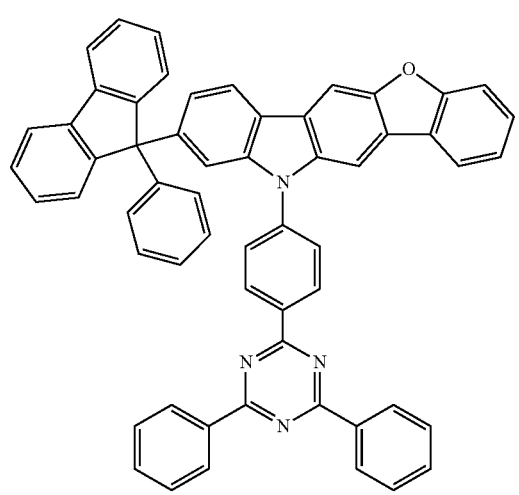
ETL-126
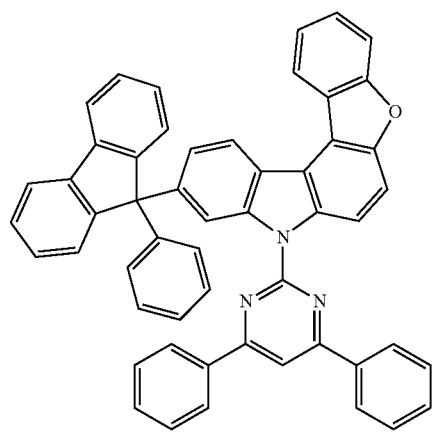
ETL-127
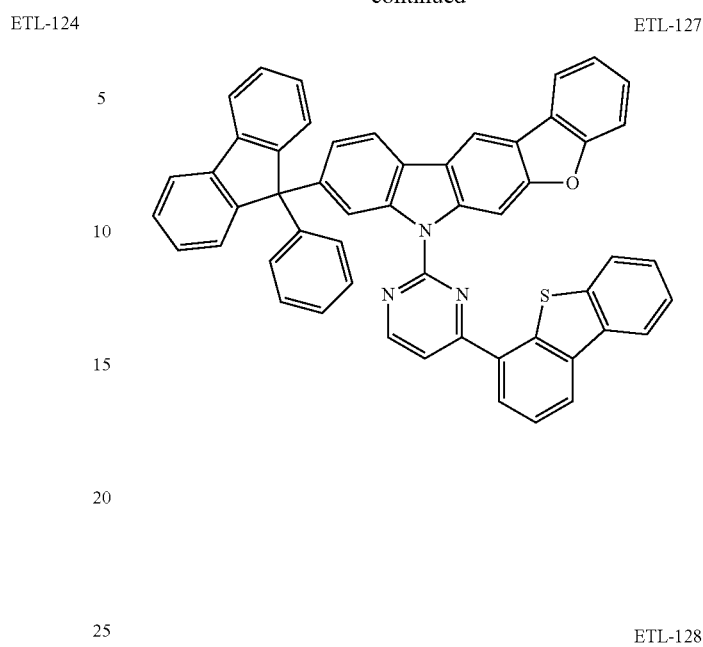
ETL-128
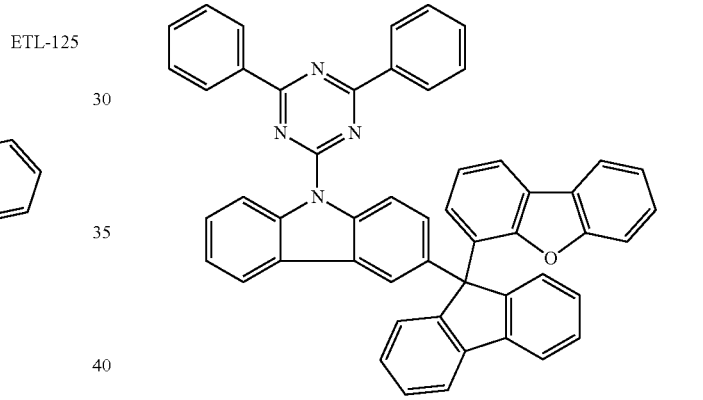
ETL-129
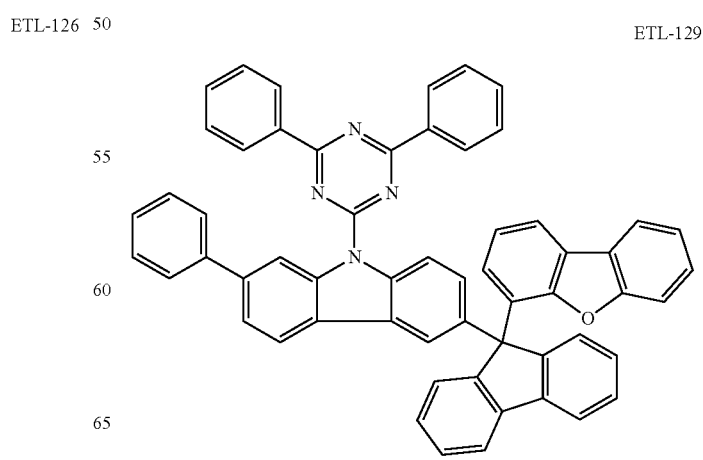

ETL-130
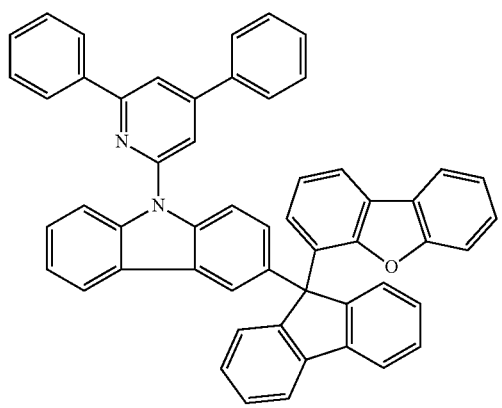
ETL-131
ETL-132
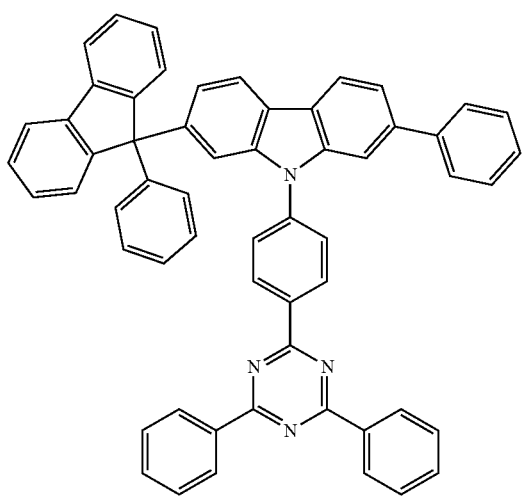
ETL-133
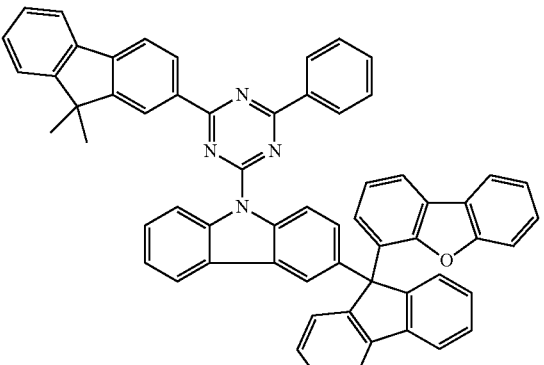
ETL-134
ETL-135
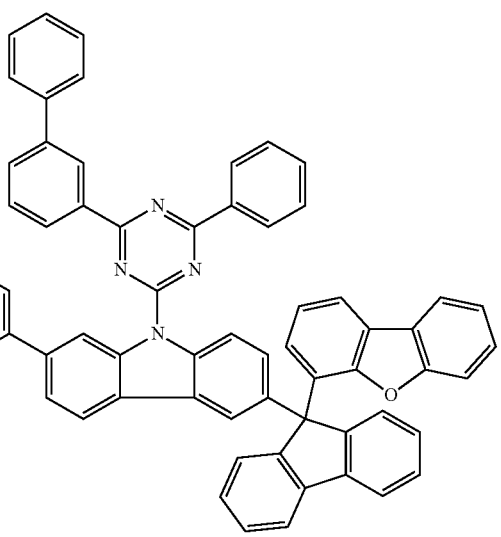

ETL-136

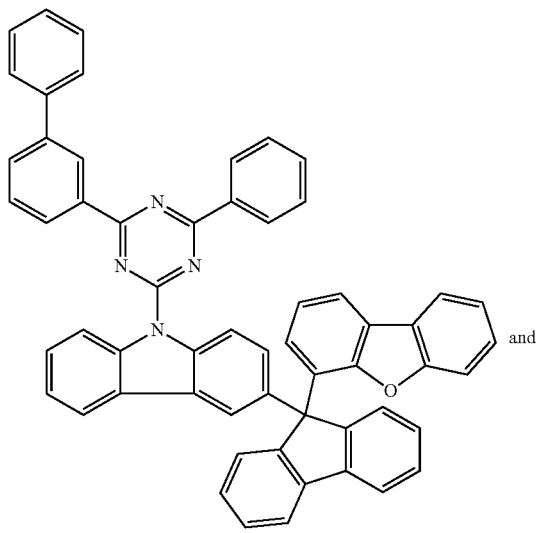

and

ETL-137

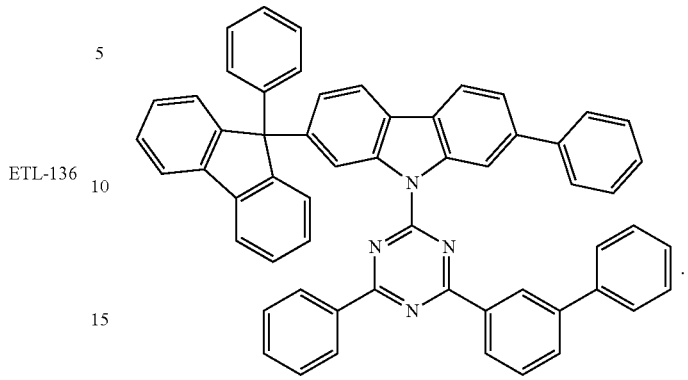

.

4. An organic electroluminescent device comprising the electron transport material containing the compound of formula 1 as defined in claim 1, and a reducing dopant.

5. The organic electroluminescent device according to claim 4, wherein the reducing dopant is one or more selected from the group consisting of an alkaline metal, an alkaline earth metal, a rare-earth metal, an oxide of an alkaline metal, a halide of an alkaline metal, an oxide of an alkaline earth metal, a halide of an alkaline earth metal, an oxide of a rare-earth metal, a halide of a rare-earth metal, an organic complex of an alkaline metal, an organic complex of an alkaline earth metal, and an organic complex of a rare-earth metal.

* * * * *